US009328148B2

(12) United States Patent
Joens et al.

(10) Patent No.: US 9,328,148 B2
(45) Date of Patent: May 3, 2016

(54) ***CAMPYLOBACTER* IMMUNOGENIC COMPOSITIONS AND USES THEREOF**

(71) Applicant: ARIZONA BOARD OF REGENTS ON BEHALF OF THE UNIVERSITY OF ARIZONA, Tucson, AZ (US)

(72) Inventors: Lynn A. Joens, Tucson, AZ (US); Bibiana Law, Tucson, AZ (US); Alexandra Armstrong, Tucson, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 14/375,365

(22) PCT Filed: Feb. 1, 2013

(86) PCT No.: PCT/US2013/024332
§ 371 (c)(1),
(2) Date: Jul. 29, 2014

(87) PCT Pub. No.: WO2013/116639
PCT Pub. Date: Aug. 8, 2013

(65) Prior Publication Data
US 2015/0030624 A1      Jan. 29, 2015

Related U.S. Application Data

(60) Provisional application No. 61/632,888, filed on Feb. 1, 2012, provisional application No. 61/689,078, filed on May 29, 2012.

(51) Int. Cl.
| | |
|---|---|
| *C07H 21/02* | (2006.01) |
| *C12N 15/00* | (2006.01) |
| *C07K 14/205* | (2006.01) |
| *A61K 39/02* | (2006.01) |
| *C12N 15/74* | (2006.01) |
| *A61K 39/00* | (2006.01) |

(52) U.S. Cl.
CPC ............ *C07K 14/205* (2013.01); *A61K 39/105* (2013.01); *C12N 15/74* (2013.01); *A61K 2039/522* (2013.01); *A61K 2039/523* (2013.01); *A61K 2039/53* (2013.01)

(58) Field of Classification Search
CPC .................................................. C07K 14/205
See application file for complete search history.

(56) References Cited

U.S. PATENT DOCUMENTS

| | | | |
|---|---|---|---|
| 5,436,146 | A | 7/1995 | Shenk et al. |
| 5,753,500 | A | 5/1998 | Shenk et al. |
| 6,040,183 | A | 3/2000 | Ferrari et al. |
| 6,093,570 | A | 7/2000 | Ferrari et al. |
| 6,548,286 | B1 | 4/2003 | Samulski et al. |
| 8,133,493 | B2 | 3/2012 | Curtiss, III |
| 2001/0038844 | A1 | 11/2001 | Nachamkin |
| 2002/0168342 | A1 | 11/2002 | Wang et al. |

FOREIGN PATENT DOCUMENTS

| | | |
|---|---|---|
| WO | 2005/049641 | 6/2005 |
| WO | 2008/008092 | 1/2008 |

OTHER PUBLICATIONS

International Search Report for PCT/US2013/024332, mailed Jul. 8, 2013.
Nielsen, et al. (2012) "Identification of immunogenic and virulence-associated Campylobacter jejuni proteins," Clinical and Vaccine Immunnology, 19(2): 113-119.
Buzby JC, Alios BM, Roberts T. The economic burden of Carnpyiobacter-associated Guilin-Barre syndrome. Journal of Infectious Diseases. 1997:176:S192-S7.
Curtiss III, R., S-Y. Wanda, B. M. Gunn, X. Zhang, S. A. Tinge, V. Ananthnarayan, H. Mo, S. Wang, and W. Kong. 2009. *Salmonella* strains with regulated delayed attenuation in vivo. Infect. Imrnurt. 77:1071-1082.
Kong, Q., Six, D.A., Roland, K.L., Liu, Q., Gu, L., Reynolds, G.M., Wang, X., Raetz, C.R., Curtiss, R., 3rd, 2011. *Salmonella* synthesizing 1-dephosphorylated [corrected] lipopolysaccharide exhibits low endotoxic activity while retaining its immunogenicity. J Immunol187, 412-423.
Li, Y., Wang, S., Scarpellini, G. Gunn, B., Xin, W., Wanda, S.Y., Roland, K.L., Curtiss, R., 3rd, 2009, Evaluation of new generation *Salmonella enterica* serovar Typhimurium vaccines with regulated delayed attenuation to induce immune responses against PspA: Proceedings of the National Academy of Sciences of the United States of America 106, 593-598.
Pope JE, Krizova A, Garg AX, Thiessen-Philbrook H. Ouirret JM. Campylobacter reactive arthritis: a systematic review. Semin Arthritis Rheum. 2007;37(1):48-55: Epub Mar. 16, 2007. doi: S0049-0 172(07)00005-4 [pii]. Ell.
Scallan E, Hoekstra RM, Angulo FJ, Tauxe RV, Widdowson MA, Roy SL, et al. Foodborne illness acquired in the United States—major pathogens. Emerging infectious diseases. 2011;17(1)7-15.
Wyszynska, A., Raczko, A., Lis, M., Jagusztyn-Krpicka, E.K., 2004. Oral immunization of chickens with av irulent *Salmonella* vaccine strain carrying C. jejuni 72Dz/92 cjaA gene elicits specific humoral immune response associated with protection against challenge with wild-type Campylobacter. Vaccine 22, 1379-1389.
Qiu et al., (2013) "Oral administration of attenuated *Salmonella typhimurium* containing a DNA vaccine against rabbit haemorrhagic disease," J. Virological Methods 188:108.
Curtiss et al, "New Technologie in Using Recombinant Attenuated *Salmonella* Vaccine Vectors," Crit Rev Immunol. 2010,30(3):255-70; 2010.
Struonell et al., (1992) "Characterization of a *Salmonella typhimurium* aro Vaccine Strain Expressing the P.69 Antigen of Borceteila pertussis," Infect. Immunol. 1992, 60.3994.
Layton et al., (2011) "Evaluation of Salmonella-Vectored Campylobacter Peptide Epitopes for Reduction of Campylobacter jejuni in Broiler Chickens," Clinical and Vaccine Immunology Mar. 2011, 449-454.
Al-Ojali et al., (2012) "Enhancement of the anti-Salmonella immune response in CD154-deficient mice by an attenuated, IFN-g-expressing, strain of *Salmonella enterica* serovar Typhimurium," Microbial Pathogenesis 52:326 (2012).

*Primary Examiner* — Albert Navarro
(74) *Attorney, Agent, or Firm* — McDonnell Boehnen Hulbert & Berghoff LLP

(57) ABSTRACT

The present invention provides immunogenic compositions against *Campylobacter* and methods for using the immunogenic composition to generate an immune response against *Campylobacter* and/or reduce intestinal colonization by *Campylobacter*.

20 Claims, 1 Drawing Sheet

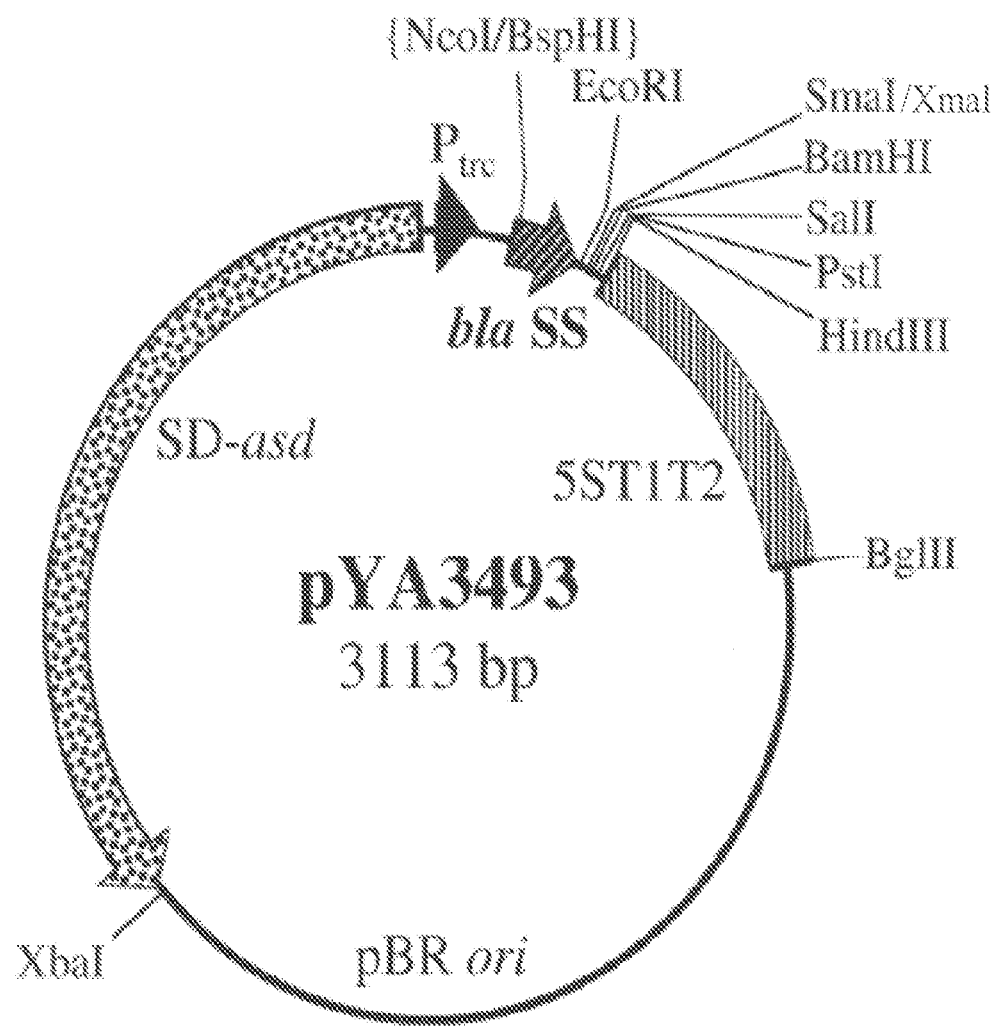

SEQUENCE LISTING

```
<160> NUMBER OF SEQ ID NOS: 142

<210> SEQ ID NO 1
<211> LENGTH: 573
<212> TYPE: DNA
<213> ORGANISM: Campylobacter jejuni

<400> SEQUENCE: 1
atgaaaaaaa ttcttgtaag tgttttaagt tcttgcttgt tagcttcggc tttaagtgct      60
gtatctttta aagaagatag tttaaagatt tcttttgaag gatataaaac taaagatatg     120
ataggaacaa aaggtgaatt taaaaatgta gaatataaat tttctaaaaa tataaaggat     180
ttggcaagtt atcttaaagg cgctaaagct accataaagc caagcaatgc ttttatgggt     240
gaaggcaatg atattataac caataatatc acaaaagtat ttttccctgc tttattggga     300
gatacggata ttaaagttgt ttttcaagat gtgattgcgg gtgaaaataa aggcgttatt     360
tcagcaaaaa ttactatgga taaaaaaagt actattgtac ctttaactta taccatcaaa     420
gataataaat ttgaagctaa aggacaactt gatttgcata cttttaaaaa tggttctaaa     480
gcattaaaag cattaagcga tgttgctgca ggacatggtg gaatttcttg gcctttagtg     540
gatatcagtt ttaatgctga tttagcagaa taa                                  573

<210> SEQ ID NO 2
<211> LENGTH: 190
<212> TYPE: PRT
<213> ORGANISM: Campylobacter jejuni

<400> SEQUENCE: 2

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Ile Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125
```

```
Lys Ser Thr Ile Val Pro Leu Thr Tyr Thr Ile Lys Asp Asn Lys Phe
            130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
            165                 170                 175

Trp Pro Leu Val Asp Ile Ser Phe Asn Ala Asp Leu Ala Glu
            180                 185                 190

<210> SEQ ID NO 3
<211> LENGTH: 762
<212> TYPE: DNA
<213> ORGANISM: Campylobacter jejuni

<400> SEQUENCE: 3
atgagatttg attttttttgt ttcaaagcgt ttaaatatca gtagaaataa agccttagag      60
cttatagaaa atgaagagat tttacttaat ggtaagagtt ttaaagcttc ttttgatgtg     120 aaaaatttt tagaaaattt aaaaaaaacg caagatttaa atcctgaaga tatacttta      180 gccaatgagt taaaattgga tcttttaagt gaaatttatg tttcaagagc agctttgaaa     240
ttaaaaaaat ttttagaaga aaatgatatt gaaataaaac ataaaaattg tcttgatata     300
ggatctagta cgggcggttt tgttcaaatt ttacttgaaa atcaggcttt aaaaatcact     360
gctcttgatg tgggtagtaa tcaactccat ccaagtttaa gagtaaatga aaaaattatc     420
ttgcatgaaa atacagatct tagagccttt aaaagtgaag aaaaatttga acttgttact     480
tgtgatgtga gttttatttc tcttattaat ttacttatt atattgataa tttagcttta     540
aaggaaatta ttttactttt taaacctcag tttgaagtgg aaaaaatat caaagagat      600 aaaaaaggtg ttttaaaaga tgataaggca atcttaaagg caagaatgga ttttgaaaaa     660
gcatgtgcta aattgggttg gcttttaaaa aatacgcaaa aatcaagcat taaaggaaag     720
gaaggtaatg ttgaatattt ttactactat atcaaaaatt aa                         762

<210> SEQ ID NO 4
<211> LENGTH: 253
<212> TYPE: PRT
<213> ORGANISM: Campylobacter jejuni

<400> SEQUENCE: 4

Met Arg Phe Asp Phe Phe Val Ser Lys Arg Leu Asn Ile Ser Arg Asn
1               5                   10                  15

Lys Ala Leu Glu Leu Ile Glu Asn Glu Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Lys Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Pro Ser Leu Arg Val Asn Glu Lys Ile Ile Leu His Glu Asn
```

```
                130                 135                 140
Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
                180                 185                 190

Val Gly Lys Asn Ile Lys Arg Asp Lys Gly Val Leu Lys Asp Asp
                195                 200                 205

Lys Ala Ile Leu Lys Ala Arg Met Asp Phe Glu Lys Ala Cys Ala Lys
                210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250

<210> SEQ ID NO 5
<211> LENGTH: 858
<212> TYPE: DNA
<213> ORGANISM: Campylobacter jejuni

<400> SEQUENCE: 5
atgattggag atatgaatga gcttttatta aaaagcgttg aagtattgcc acctttacct    60
gatactgtaa gtaagttaag aaaatatgtg agcgaggcta attcaaatat agaaactatg   120
aaagttgctg aaatcatttc aagcgatccg ttgatgacgg ctaagctttt gcaattagca   180
aattctcctt attatggttt tacaagagaa attacaacca taaatcaagt gattacttta   240
ttaggcgttg gtaatatcat caatatagtt atggctgact ccattagaga taattttaaa   300
atagacgttt caccttatgg tttaaatact caaaattttt taaaaacgtg caatgaagag   360
gcaactttta tcgcaaattg gcttaatgat gaagataaaa actttctca tcttttagtt   420 ccttgtgcaa tgcttttaag gcttggtatt gttatttttt caaattttct tatacaaaat   480
cataaggata aggatttttt agcttttta aataaaaatg aaaatcttgc tttagcggag   540
aatgaatttt taggcgtaga tcatatttct ttcttgggat ttttgttaca tcgttggaat   600
tttgatgatg ttttgattga agtatatgt tttgttcgca ctcctcatgc tgctcgcgaa   660
aaagtgaaaa atccgctta tgctttagca ataacagatc atcttttgc tccgcatgat   720 ggttcttctc catttaacgc aaaagctgca gttgctttac ttaaagaggc aaaaactcaa   780
ggaattaatt ttgatttaaa caatcttta tctaagcttc taacaaagc taaggaaaat   840 ttaaacaaag aagattaa                                                858

<210> SEQ ID NO 6
<211> LENGTH: 285
<212> TYPE: PRT
<213> ORGANISM: Campylobacter jejuni

<400> SEQUENCE: 6

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
                20                  25                  30

Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
```

```
                50                  55                  60
Tyr Gly Phe Thr Arg Glu Ile Thr Thr Ile Asn Gln Val Ile Thr Leu
 65                  70                  75                  80

Leu Gly Val Gly Asn Ile Ile Asn Ile Val Met Ala Asp Ser Ile Arg
                    85                  90                  95

Asp Asn Phe Lys Ile Asp Val Ser Pro Tyr Gly Leu Asn Thr Gln Asn
                100                 105                 110

Phe Leu Lys Thr Cys Asn Glu Glu Ala Thr Phe Ile Ala Asn Trp Leu
                115                 120                 125

Asn Asp Glu Asp Lys Lys Leu Ser His Leu Leu Val Pro Cys Ala Met
                130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
                180                 185                 190

Gly Phe Leu Leu His Arg Trp Asn Phe Asp Asp Val Leu Ile Glu Ser
                195                 200                 205

Ile Cys Phe Val Arg Thr Pro His Ala Ala Arg Glu Lys Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Lys Glu
                245                 250                 255

Ala Lys Thr Gln Gly Ile Asn Phe Asp Leu Asn Asn Leu Leu Ser Lys
                260                 265                 270

Leu Pro Asn Lys Ala Lys Glu Asn Leu Asn Lys Glu Asp
                275                 280                 285

<210> SEQ ID NO 7
<211> LENGTH: 190
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is I, V, or F
<220> FEATURE:
<221> NAME/KEY: MISC_FEATURE
<222> LOCATION: (5)..(5)
<223> OTHER INFORMATION: X is V or F
<220> FEATURE:
<221> NAME/KEY: MISC_FEATURE
<222> LOCATION: (6)..(6)
<223> OTHER INFORMATION: X is V, A, or L
<220> FEATURE:
<221> NAME/KEY: MISC_FEATURE
<222> LOCATION: (8)..(8)
<223> OTHER INFORMATION: X is V or I
<220> FEATURE:
<221> NAME/KEY: MISC_FEATURE
<222> LOCATION: (9)..(9)
<223> OTHER INFORMATION: X is L or F
<220> FEATURE:
<221> NAME/KEY: MISC_FEATURE
<222> LOCATION: (11)..(11)
<223> OTHER INFORMATION: X is S or F
<220> FEATURE:
<221> NAME/KEY: MISC_FEATURE
<222> LOCATION: (30)..(30)
<223> OTHER INFORMATION: X is I or V
```

```
<220> FEATURE:
<221> NAME/KEY: MISC_FEATURE
<222> LOCATION: (41)..(41)
<223> OTHER INFORMATION: X is I or V
<220> FEATURE:
<221> NAME/KEY: MISC_FEATURE
<222> LOCATION: (43)..(43)
<223> OTHER INFORMATION: X is T, V, I or A
<220> FEATURE:
<221> NAME/KEY: MISC_FEATURE
<222> LOCATION: (44)..(44)
<223> OTHER INFORMATION: X is K or R
<220> FEATURE:
<221> NAME/KEY: MISC_FEATURE
<222> LOCATION: (53)..(53)
<223> OTHER INFORMATION: X is K or N
<220> FEATURE:
<221> NAME/KEY: MISC_FEATURE
<222> LOCATION: (57)..(57)
<223> OTHER INFORMATION: X is N or S
<220> FEATURE:
<221> NAME/KEY: MISC_FEATURE
<222> LOCATION: (58)..(58)
<223> OTHER INFORMATION: X is I or T
<220> FEATURE:
<221> NAME/KEY: MISC_FEATURE
<222> LOCATION: (61)..(61)
<223> OTHER INFORMATION: X is L or F
<220> FEATURE:
<221> NAME/KEY: MISC_FEATURE
<222> LOCATION: (73)..(73)
<223> OTHER INFORMATION: X is K or E
<220> FEATURE:
<221> NAME/KEY: MISC_FEATURE
<222> LOCATION: (76)..(76)
<223> OTHER INFORMATION: X is N or D
<220> FEATURE:
<221> NAME/KEY: MISC_FEATURE
<222> LOCATION: (80)..(80)
<223> OTHER INFORMATION: X is G or S
<220> FEATURE:
<221> NAME/KEY: MISC_FEATURE
<222> LOCATION: (83)..(83)
<223> OTHER INFORMATION: X is N or L
<220> FEATURE:
<221> NAME/KEY: MISC_FEATURE
<222> LOCATION: (85)..(85)
<223> OTHER INFORMATION: X is I or V
<220> FEATURE:
<221> NAME/KEY: MISC_FEATURE
<222> LOCATION: (101)..(101)
<223> OTHER INFORMATION: X is D or N
<220> FEATURE:
<221> NAME/KEY: MISC_FEATURE
<222> LOCATION: (102)..(102)
<223> OTHER INFORMATION: X is T or A
<220> FEATURE:
<221> NAME/KEY: MISC_FEATURE
<222> LOCATION: (111)..(111)
<223> OTHER INFORMATION: X is V, A or M
<220> FEATURE:
<221> NAME/KEY: MISC_FEATURE
<222> LOCATION: (113)..(113)
<223> OTHER INFORMATION: X is V or  A
<220> FEATURE:
<221> NAME/KEY: MISC_FEATURE
<222> LOCATION: (116)..(123)
<223> OTHER INFORMATION: Amino Acid is optionally absent
<220> FEATURE:
<221> NAME/KEY: MISC_FEATURE
<222> LOCATION: (133)..(133)
<223> OTHER INFORMATION: X is V or I
<220> FEATURE:
<221> NAME/KEY: MISC_FEATURE
<222> LOCATION: (142)..(142)
<223> OTHER INFORMATION: X is N or D
<220> FEATURE:
<221> NAME/KEY: MISC_FEATURE
<222> LOCATION: (150)..(150)
```

```
<223> OTHER INFORMATION: X is L or F
<220> FEATURE:
<221> NAME/KEY: MISC_FEATURE
<222> LOCATION: (154)..(154)
<223> OTHER INFORMATION: X is T or A
<220> FEATURE:
<221> NAME/KEY: MISC_FEATURE
<222> LOCATION: (158)..(158)
<223> OTHER INFORMATION: X is G or A
<220> FEATURE:
<221> NAME/KEY: MISC_FEATURE
<222> LOCATION: (168)..(168)
<223> OTHER INFORMATION: X is V or A
<220> FEATURE:
<221> NAME/KEY: MISC_FEATURE
<222> LOCATION: (170)..(170)
<223> OTHER INFORMATION: X is A, T or P
<220> FEATURE:
<221> NAME/KEY: MISC_FEATURE
<222> LOCATION: (189)..(189)
<223> OTHER INFORMATION: X is A, T or V

<400> SEQUENCE: 7

Met Lys Lys Xaa Xaa Xaa Ser Xaa Xaa Ser Xaa Cys Leu Leu Ala Ser
1               5                   10                  15

Ala Leu Ser Ala Val Ser Phe Lys Glu Asp Ser Leu Lys Xaa Ser Phe
            20                  25                  30

Glu Gly Tyr Lys Thr Lys Asp Met Xaa Gly Xaa Xaa Gly Glu Phe Lys
        35                  40                  45

Asn Val Glu Tyr Xaa Phe Ser Lys Xaa Xaa Lys Asp Xaa Ala Ser Tyr
    50                  55                  60

Leu Lys Gly Ala Lys Ala Thr Ile Xaa Pro Ser Xaa Ala Phe Met Xaa
65                  70                  75                  80

Glu Gly Xaa Asp Xaa Ile Thr Asn Asn Ile Thr Lys Val Phe Phe Pro
                85                  90                  95

Ala Leu Leu Gly Xaa Xaa Asp Ile Lys Val Val Phe Gln Asp Xaa Ile
            100                 105                 110

Xaa Gly Glu Asn Lys Gly Val Ile Ser Ala Lys Ile Thr Met Asp Lys
        115                 120                 125

Lys Ser Thr Ile Xaa Pro Leu Thr Tyr Thr Ile Lys Asp Xaa Lys Phe
    130                 135                 140

Glu Ala Lys Gly Gln Xaa Asp Leu His Xaa Phe Lys Asn Xaa Ser Lys
145                 150                 155                 160

Ala Leu Lys Ala Leu Ser Asp Xaa Ala Xaa Gly His Gly Gly Ile Ser
                165                 170                 175

Trp Pro Leu Val Asp Ile Ser Phe Asn Ala Asp Leu Xaa Glu
            180                 185                 190

<210> SEQ ID NO 8
<211> LENGTH: 253
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(65)
<223> OTHER INFORMATION: Amino Acids are optionally absent
<220> FEATURE:
<221> NAME/KEY: MISC_FEATURE
<222> LOCATION: (2)..(2)
<223> OTHER INFORMATION: X is R or I
<220> FEATURE:
<221> NAME/KEY: MISC_FEATURE
<222> LOCATION: (3)..(3)
<223> OTHER INFORMATION: X is F or absent
```

```
<220> FEATURE:
<221> NAME/KEY: MISC_FEATURE
<222> LOCATION: (4)..(4)
<223> OTHER INFORMATION: X is D or absent
<220> FEATURE:
<221> NAME/KEY: MISC_FEATURE
<222> LOCATION: (7)..(7)
<223> OTHER INFORMATION: X is V or I
<220> FEATURE:
<221> NAME/KEY: MISC_FEATURE
<222> LOCATION: (12)..(12)
<223> OTHER INFORMATION: X is N or D
<220> FEATURE:
<221> NAME/KEY: MISC_FEATURE
<222> LOCATION: (24)..(24)
<223> OTHER INFORMATION: X is N or S
<220> FEATURE:
<221> NAME/KEY: MISC_FEATURE
<222> LOCATION: (27)..(27)
<223> OTHER INFORMATION: X is I or V
<220> FEATURE:
<221> NAME/KEY: MISC_FEATURE
<222> LOCATION: (33)..(33)
<223> OTHER INFORMATION: X is S or N
<220> FEATURE:
<221> NAME/KEY: MISC_FEATURE
<222> LOCATION: (38)..(38)
<223> OTHER INFORMATION: X is F or C
<220> FEATURE:
<221> NAME/KEY: MISC_FEATURE
<222> LOCATION: (43)..(43)
<223> OTHER INFORMATION: X is F or L
<220> FEATURE:
<221> NAME/KEY: MISC_FEATURE
<222> LOCATION: (50)..(50)
<223> OTHER INFORMATION: X is T, A or K
<220> FEATURE:
<221> NAME/KEY: MISC_FEATURE
<222> LOCATION: (55)..(55)
<223> OTHER INFORMATION: X is P, L or S
<220> FEATURE:
<221> NAME/KEY: MISC_FEATURE
<222> LOCATION: (57)..(57)
<223> OTHER INFORMATION: X is D or E
<220> FEATURE:
<221> NAME/KEY: MISC_FEATURE
<222> LOCATION: (58)..(58)
<223> OTHER INFORMATION: X is I or V
<220> FEATURE:
<221> NAME/KEY: MISC_FEATURE
<222> LOCATION: (59)..(59)
<223> OTHER INFORMATION: X is L or Y
<220> FEATURE:
<221> NAME/KEY: MISC_FEATURE
<222> LOCATION: (61)..(61)
<223> OTHER INFORMATION: X is A, T or S
<220> FEATURE:
<221> NAME/KEY: MISC_FEATURE
<222> LOCATION: (62)..(62)
<223> OTHER INFORMATION: X is N, D or K
<220> FEATURE:
<221> NAME/KEY: MISC_FEATURE
<222> LOCATION: (63)..(63)
<223> OTHER INFORMATION: X is E or G
<220> FEATURE:
<221> NAME/KEY: MISC_FEATURE
<222> LOCATION: (65)..(65)
<223> OTHER INFORMATION: X is K or N
<220> FEATURE:
<221> NAME/KEY: MISC_FEATURE
<222> LOCATION: (66)..(66)
<223> OTHER INFORMATION: X is L or M
<220> FEATURE:
<221> NAME/KEY: MISC_FEATURE
<222> LOCATION: (67)..(67)
<223> OTHER INFORMATION: X is D, N or E
<220> FEATURE:
<221> NAME/KEY: MISC_FEATURE
<222> LOCATION: (70)..(70)
```

```
<223> OTHER INFORMATION: X is S or R
<220> FEATURE:
<221> NAME/KEY: MISC_FEATURE
<222> LOCATION: (74)..(74)
<223> OTHER INFORMATION: X is V or I
<220> FEATURE:
<221> NAME/KEY: MISC_FEATURE
<222> LOCATION: (83)..(83)
<223> OTHER INFORMATION: X is K or N
<220> FEATURE:
<221> NAME/KEY: MISC_FEATURE
<222> LOCATION: (89)..(89)
<223> OTHER INFORMATION: X is D, G or N
<220> FEATURE:
<221> NAME/KEY: MISC_FEATURE
<222> LOCATION: (92)..(92)
<223> OTHER INFORMATION: X is I or V
<220> FEATURE:
<221> NAME/KEY: MISC_FEATURE
<222> LOCATION: (93)..(93)
<223> OTHER INFORMATION: X is K or N
<220> FEATURE:
<221> NAME/KEY: MISC_FEATURE
<222> LOCATION: (94)..(94)
<223> OTHER INFORMATION: X is H, Q or N
<220> FEATURE:
<221> NAME/KEY: MISC_FEATURE
<222> LOCATION: (115)..(115)
<223> OTHER INFORMATION: X is Q or K
<220> FEATURE:
<221> NAME/KEY: MISC_FEATURE
<222> LOCATION: (121)..(121)
<223> OTHER INFORMATION: X is A or T
<220> FEATURE:
<221> NAME/KEY: MISC_FEATURE
<222> LOCATION: (126)..(126)
<223> OTHER INFORMATION: X is S or N
<220> FEATURE:
<221> NAME/KEY: MISC_FEATURE
<222> LOCATION: (131)..(131)
<223> OTHER INFORMATION: X is P, S or L
<220> FEATURE:
<221> NAME/KEY: MISC_FEATURE
<222> LOCATION: (132)..(132)
<223> OTHER INFORMATION: X is S or N
<220> FEATURE:
<221> NAME/KEY: MISC_FEATURE
<222> LOCATION: (135)..(135)
<223> OTHER INFORMATION: X is V, A or T
<220> FEATURE:
<221> NAME/KEY: MISC_FEATURE
<222> LOCATION: (138)..(138)
<223> OTHER INFORMATION: X is K or I
<220> FEATURE:
<221> NAME/KEY: MISC_FEATURE
<222> LOCATION: (139)..(139)
<223> OTHER INFORMATION: X is V or I
<220> FEATURE:
<221> NAME/KEY: MISC_FEATURE
<222> LOCATION: (142)..(142)
<223> OTHER INFORMATION: X is H or Y
<220> FEATURE:
<221> NAME/KEY: MISC_FEATURE
<222> LOCATION: (145)..(145)
<223> OTHER INFORMATION: X is T or I
<220> FEATURE:
<221> NAME/KEY: MISC_FEATURE
<222> LOCATION: (149)..(149)
<223> OTHER INFORMATION: X is A, T or V
<220> FEATURE:
<221> NAME/KEY: MISC_FEATURE
<222> LOCATION: (158)..(158)
<223> OTHER INFORMATION: X is L or F
<220> FEATURE:
<221> NAME/KEY: MISC_FEATURE
<222> LOCATION: (159)..(159)
<223> OTHER INFORMATION: X is V or I
<220> FEATURE:
<221> NAME/KEY: MISC_FEATURE
```

```
<222> LOCATION: (169)..(169)
<223> OTHER INFORMATION: X is V or I
<220> FEATURE:
<221> NAME/KEY: MISC_FEATURE
<222> LOCATION: (175)..(175)
<223> OTHER INFORMATION: X is V or I
<220> FEATURE:
<221> NAME/KEY: MISC_FEATURE
<222> LOCATION: (176)..(176)
<223> OTHER INFORMATION: X is D or N
<220> FEATURE:
<221> NAME/KEY: MISC_FEATURE
<222> LOCATION: (181)..(181)
<223> OTHER INFORMATION: X is K or R
<220> FEATURE:
<221> NAME/KEY: MISC_FEATURE
<222> LOCATION: (197)..(197)
<223> OTHER INFORMATION: X is I or V
<220> FEATURE:
<221> NAME/KEY: MISC_FEATURE
<222> LOCATION: (208)..(208)
<223> OTHER INFORMATION: X is D or G
<220> FEATURE:
<221> NAME/KEY: MISC_FEATURE
<222> LOCATION: (209)..(209)
<223> OTHER INFORMATION: X is K or R
<220> FEATURE:
<221> NAME/KEY: MISC_FEATURE
<222> LOCATION: (210)..(210)
<223> OTHER INFORMATION: X is A or V
<220> FEATURE:
<221> NAME/KEY: MISC_FEATURE
<222> LOCATION: (215)..(215)
<223> OTHER INFORMATION: X is K or R
<220> FEATURE:
<221> NAME/KEY: MISC_FEATURE
<222> LOCATION: (221)..(221)
<223> OTHER INFORMATION: X is A or E
<220> FEATURE:
<221> NAME/KEY: MISC_FEATURE
<222> LOCATION: (226)..(226)
<223> OTHER INFORMATION: X is G or S
<220> FEATURE:
<221> NAME/KEY: MISC_FEATURE
<222> LOCATION: (228)..(228)
<223> OTHER INFORMATION: X is L, F or I
<220> FEATURE:
<221> NAME/KEY: MISC_FEATURE
<222> LOCATION: (236)..(236)
<223> OTHER INFORMATION: X is S or C

<400> SEQUENCE: 8

Met Xaa Xaa Xaa Phe Phe Xaa Ser Lys Arg Leu Xaa Ile Ser Arg Asn
1               5                   10                  15

Lys Ala Leu Glu Leu Ile Glu Xaa Glu Glu Xaa Leu Leu Asn Gly Lys
            20                  25                  30

Xaa Phe Lys Ala Ser Xaa Asp Val Lys Asn Xaa Leu Glu Asn Leu Lys
        35                  40                  45

Lys Xaa Gln Asp Leu Asn Xaa Glu Xaa Xaa Xaa Leu Xaa Xaa Xaa Leu
    50                  55                  60

Xaa Xaa Xaa Leu Leu Xaa Glu Ile Tyr Xaa Ser Arg Ala Ala Leu Lys
65                  70                  75                  80

Leu Lys Xaa Phe Leu Glu Glu Asn Xaa Ile Glu Xaa Xaa Xaa Lys Asn
                85                  90                  95

Cys Leu Asp Ile Gly Ser Ser Thr Gly Gly Phe Val Gln Ile Leu Leu
            100                 105                 110

Glu Asn Xaa Ala Leu Lys Ile Thr Xaa Leu Asp Val Gly Xaa Asn Gln
        115                 120                 125

Leu His Xaa Xaa Leu Arg Xaa Asn Glu Xaa Xaa Ile Leu Xaa Glu Asn
    130                 135                 140
```

```
Xaa Asp Leu Arg Xaa Phe Lys Ser Glu Glu Lys Phe Glu Xaa Xaa Thr
145                 150                 155                 160

Cys Asp Val Ser Phe Ile Ser Leu Xaa Asn Leu Leu Tyr Tyr Xaa Xaa
                165                 170                 175

Asn Leu Ala Leu Xaa Glu Ile Ile Leu Leu Phe Lys Pro Gln Phe Glu
            180                 185                 190

Val Gly Lys Asn Xaa Lys Arg Asp Lys Lys Gly Val Leu Lys Asp Xaa
        195                 200                 205

Xaa Xaa Ile Leu Lys Ala Xaa Met Asp Phe Glu Lys Xaa Cys Ala Lys
    210                 215                 220

Leu Xaa Trp Xaa Leu Lys Asn Thr Gln Lys Ser Xaa Ile Lys Gly Lys
225                 230                 235                 240

Glu Gly Asn Val Glu Tyr Phe Tyr Tyr Tyr Ile Lys Asn
                245                 250
```

<210> SEQ ID NO 9
<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is M or absent
<220> FEATURE:
<221> NAME/KEY: MISC_FEATURE
<222> LOCATION: (3)..(3)
<223> OTHER INFORMATION: X is G or absent
<220> FEATURE:
<221> NAME/KEY: MISC_FEATURE
<222> LOCATION: (43)..(43)
<223> OTHER INFORMATION: X is A or V
<220> FEATURE:
<221> NAME/KEY: MISC_FEATURE
<222> LOCATION: (75)..(75)
<223> OTHER INFORMATION: X is N or S
<220> FEATURE:
<221> NAME/KEY: MISC_FEATURE
<222> LOCATION: (83)..(83)
<223> OTHER INFORMATION: X is V or I
<220> FEATURE:
<221> NAME/KEY: MISC_FEATURE
<222> LOCATION: (91)..(91)
<223> OTHER INFORMATION: X is M or T
<220> FEATURE:
<221> NAME/KEY: MISC_FEATURE
<222> LOCATION: (96)..(96)
<223> OTHER INFORMATION: X is K or R
<220> FEATURE:
<221> NAME/KEY: MISC_FEATURE
<222> LOCATION: (98)..(98)
<223> OTHER INFORMATION: X is N or S
<220> FEATURE:
<221> NAME/KEY: MISC_FEATURE
<222> LOCATION: (109)..(109)
<223> OTHER INFORMATION: X is N or D
<220> FEATURE:
<221> NAME/KEY: MISC_FEATURE
<222> LOCATION: (111)..(111)
<223> OTHER INFORMATION: X is Q or K
<220> FEATURE:
<221> NAME/KEY: MISC_FEATURE
<222> LOCATION: (112)..(112)
<223> OTHER INFORMATION: X is N or V
<220> FEATURE:
<221> NAME/KEY: MISC_FEATURE
<222> LOCATION: (115)..(115)
<223> OTHER INFORMATION: X is K or R
<220> FEATURE:
<221> NAME/KEY: MISC_FEATURE

```
<222> LOCATION: (116)..(116)
<223> OTHER INFORMATION: X is T or N
<220> FEATURE:
<221> NAME/KEY: MISC_FEATURE
<222> LOCATION: (119)..(119)
<223> OTHER INFORMATION: X is E or D
<220> FEATURE:
<221> NAME/KEY: MISC_FEATURE
<222> LOCATION: (125)..(125)
<223> OTHER INFORMATION: X is A, V or T
<220> FEATURE:
<221> NAME/KEY: MISC_FEATURE
<222> LOCATION: (161)..(161)
<223> OTHER INFORMATION: X is H, Y or F
<220> FEATURE:
<221> NAME/KEY: MISC_FEATURE
<222> LOCATION: (162)..(162)
<223> OTHER INFORMATION: X is K or R
<220> FEATURE:
<221> NAME/KEY: MISC_FEATURE
<222> LOCATION: (163)..(163)
<223> OTHER INFORMATION: X is D or E
<220> FEATURE:
<221> NAME/KEY: MISC_FEATURE
<222> LOCATION: (163)..(260)
<223> OTHER INFORMATION: amino acids are optionally absent
<220> FEATURE:
<221> NAME/KEY: MISC_FEATURE
<222> LOCATION: (165)..(165)
<223> OTHER INFORMATION: X is D or E
<220> FEATURE:
<221> NAME/KEY: MISC_FEATURE
<222> LOCATION: (168)..(168)
<223> OTHER INFORMATION: X is A or T
<220> FEATURE:
<221> NAME/KEY: MISC_FEATURE
<222> LOCATION: (172)..(172)
<223> OTHER INFORMATION: X is E, K or absent
<220> FEATURE:
<221> NAME/KEY: MISC_FEATURE
<222> LOCATION: (173)..(173)
<223> OTHER INFORMATION: X is T or absent
<220> FEATURE:
<221> NAME/KEY: MISC_FEATURE
<222> LOCATION: (175)..(175)
<223> OTHER INFORMATION: X is N, S or I
<220> FEATURE:
<221> NAME/KEY: MISC_FEATURE
<222> LOCATION: (178)..(178)
<223> OTHER INFORMATION: X is L or I
<220> FEATURE:
<221> NAME/KEY: MISC_FEATURE
<222> LOCATION: (199)..(199)
<223> OTHER INFORMATION: X is H or Y
<220> FEATURE:
<221> NAME/KEY: MISC_FEATURE
<222> LOCATION: (206)..(206)
<223> OTHER INFORMATION: X is V or I
<220> FEATURE:
<221> NAME/KEY: MISC_FEATURE
<222> LOCATION: (215)..(215)
<223> OTHER INFORMATION: X is R or H
<220> FEATURE:
<221> NAME/KEY: MISC_FEATURE
<222> LOCATION: (223)..(223)
<223> OTHER INFORMATION: X is K or E
<220> FEATURE:
<221> NAME/KEY: MISC_FEATURE
<222> LOCATION: (239)..(239)
<223> OTHER INFORMATION: X is A or T
<220> FEATURE:
<221> NAME/KEY: MISC_FEATURE
<222> LOCATION: (249)..(249)
<223> OTHER INFORMATION: X is A, V or T
<220> FEATURE:
<221> NAME/KEY: MISC_FEATURE
<222> LOCATION: (257)..(257)
<223> OTHER INFORMATION: X is K or E
<220> FEATURE:
```

```
<221> NAME/KEY: MISC_FEATURE
<222> LOCATION: (261)..(287)
<223> OTHER INFORMATION: Amino acids are optionally absent
<220> FEATURE:
<221> NAME/KEY: MISC_FEATURE
<222> LOCATION: (261)..(287)
<223> OTHER INFORMATION: amino acids are optionally NSRN with the rest
      absent
<220> FEATURE:
<221> NAME/KEY: MISC_FEATURE
<222> LOCATION: (269)..(269)
<223> OTHER INFORMATION: X is N or D
<220> FEATURE:
<221> NAME/KEY: MISC_FEATURE
<222> LOCATION: (277)..(277)
<223> OTHER INFORMATION: X is N or D
<220> FEATURE:
<221> NAME/KEY: MISC_FEATURE
<222> LOCATION: (277)..(277)
<223> OTHER INFORMATION: X is N or S
<220> FEATURE:
<221> NAME/KEY: MISC_FEATURE
<222> LOCATION: (284)..(284)
<223> OTHER INFORMATION: X is N or D
<220> FEATURE:
<221> NAME/KEY: MISC_FEATURE
<222> LOCATION: (285)..(285)
<223> OTHER INFORMATION: X is K or E

<400> SEQUENCE: 9
```

Xaa Ile Xaa Asp Met Asn Glu Leu Leu Leu Lys Ser Val Glu Val Leu
 1               5                  10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Xaa Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Xaa Gln Val Ile Thr Leu
65                  70                  75                  80

Leu Gly Xaa Gly Asn Ile Ile Asn Ile Val Xaa Ala Asp Ser Ile Xaa
                85                  90                  95

Asp Xaa Phe Lys Ile Asp Val Ser Pro Tyr Gly Leu Xaa Thr Xaa Xaa
            100                 105                 110

Phe Leu Xaa Xaa Cys Asn Xaa Glu Ala Thr Phe Ile Xaa Asn Trp Leu
        115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn
145                 150                 155                 160

Xaa Xaa Xaa Lys Xaa Phe Leu Xaa Phe Leu Asn Xaa Xaa Lys Xaa Glu
                165                 170                 175

Asn Xaa Ala Leu Ala Glu Asn Glu Phe Leu Gly Val Asp His Ile Ser
            180                 185                 190

Phe Leu Gly Phe Leu Leu Xaa Arg Trp Asn Phe Asp Xaa Leu Ile
        195                 200                 205

Glu Ser Ile Cys Phe Val Xaa Thr Pro His Ala Ala Arg Glu Xaa Val
    210                 215                 220

Lys Lys Ser Ala Tyr Ala Leu Ala Ile Thr Asp His Leu Phe Xaa Pro
225                 230                 235                 240

His Asp Gly Ser Ser Pro Phe Asn Xaa Lys Ala Val Ala Leu Leu
                245                 250                 255

```
Xaa Glu Ala Lys Thr Gln Gly Ile Asn Phe Asp Leu Xaa Asn Leu Leu
            260                 265                 270

Ser Lys Leu Pro Xaa Lys Ala Lys Glu Asn Leu Xaa Xaa Glu Asp
        275                 280                 285

<210> SEQ ID NO 10
<211> LENGTH: 298
<212> TYPE: PRT
<213> ORGANISM: Campylobacter jejuni

<400> SEQUENCE: 10

Met Gln Ile Ile Ile Leu Ile Lys Asp Lys Leu Asn Met Ile Gly
1               5                   10                  15

Asp Met Asn Glu Leu Leu Leu Lys Ser Val Glu Val Leu Pro Pro Leu
            20                  25                  30

Pro Asp Thr Val Ser Lys Leu Arg Lys Tyr Val Ser Glu Ala Asn Ser
            35                  40                  45

Asn Ile Glu Thr Met Lys Val Ala Glu Ile Ile Ser Ser Asp Pro Leu
        50                  55                  60

Met Thr Ala Lys Leu Leu Gln Leu Ala Asn Ser Pro Tyr Tyr Gly Phe
65                  70                  75                  80

Thr Arg Glu Ile Thr Thr Ile Asn Gln Val Ile Thr Leu Leu Gly Val
                85                  90                  95

Gly Asn Ile Ile Asn Ile Val Met Ala Asp Ser Ile Arg Asp Asn Phe
            100                 105                 110

Lys Ile Asp Val Ser Pro Tyr Gly Leu Asn Thr Gln Asn Phe Leu Lys
        115                 120                 125

Thr Cys Asn Glu Glu Ala Thr Phe Ile Ala Asn Trp Leu Asn Asp Glu
130                 135                 140

Asp Lys Lys Leu Ser His Leu Leu Val Pro Cys Ala Met Leu Leu Arg
145                 150                 155                 160

Leu Gly Ile Val Ile Phe Ser Asn Phe Leu Ile Gln Asn His Lys Asp
                165                 170                 175

Lys Asp Phe Leu Ala Phe Leu Asn Lys Asn Glu Asn Leu Ala Leu Ala
            180                 185                 190

Glu Asn Glu Phe Leu Gly Val Asp His Ile Ser Phe Leu Gly Phe Leu
        195                 200                 205

Leu His Arg Trp Asn Phe Asp Asp Val Leu Ile Glu Ser Ile Cys Phe
210                 215                 220

Val Arg Thr Pro His Ala Ala Arg Glu Lys Val Lys Lys Ser Ala Tyr
225                 230                 235                 240

Ala Leu Ala Ile Thr Asp His Leu Phe Ala Pro His Asp Gly Ser Ser
                245                 250                 255

Pro Phe Asn Ala Lys Ala Ala Val Leu Leu Lys Glu Ala Lys Thr
            260                 265                 270

Gln Gly Ile Asn Phe Asp Leu Asn Asn Leu Leu Ser Lys Leu Pro Asn
        275                 280                 285

Lys Ala Lys Glu Asn Leu Asn Lys Glu Asp
            290                 295

<210> SEQ ID NO 11
<211> LENGTH: 285
<212> TYPE: PRT
<213> ORGANISM: Campylobacter jejuni

<400> SEQUENCE: 11
```

```
Met Ile Gly Asp Met Asn Glu Leu Leu Lys Ser Val Glu Val Leu
1               5                   10                  15

Pro Pro Leu Pro Asp Thr Val Ser Lys Leu Arg Lys Tyr Val Ser Glu
                20                  25                  30

Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Lys Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Lys Glu
                245                 250                 255

Ala Lys Thr Gln Gly Ile Asn Phe Asp Leu Asn Asn Leu Leu Ser Lys
            260                 265                 270

Leu Pro Asn Lys Ala Lys Glu Asn Leu Asn Lys Glu Asp
        275                 280                 285

<210> SEQ ID NO 12
<211> LENGTH: 285
<212> TYPE: PRT
<213> ORGANISM: Campylobacter jejuni

<400> SEQUENCE: 12

Met Ile Gly Asp Met Asn Glu Leu Leu Lys Ser Val Glu Val Leu
1               5                   10                  15

Pro Pro Leu Pro Asp Thr Val Ser Lys Leu Arg Lys Tyr Val Ser Glu
                20                  25                  30

Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95
```

-continued

```
Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Ser Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Lys Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Lys Glu
                245                 250                 255

Ala Lys Thr Gln Gly Ile Asn Phe Asp Leu Asn Asn Leu Leu Ser Lys
            260                 265                 270

Leu Pro Asn Lys Ala Lys Glu Asn Leu Asn Lys Glu Asp
        275                 280                 285

<210> SEQ ID NO 13
<211> LENGTH: 285
<212> TYPE: PRT
<213> ORGANISM: Campylobacter jejuni

<400> SEQUENCE: 13

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Asp Glu Ala Thr Phe Ile Ala Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
```

```
              180                 185                 190
Gly Phe Leu Leu His Arg Trp Asn Phe Asp Asp Val Leu Ile Glu Ser
            195                 200                 205
Ile Cys Phe Val Arg Thr Pro His Ala Ala Arg Glu Lys Val Lys Lys
        210                 215                 220
Ser Ala Tyr Ala Leu Ala Ile Thr Asp His Leu Phe Ala Pro His Asp
225                 230                 235                 240
Gly Ser Ser Pro Phe Asn Ala Lys Ala Val Ala Leu Leu Lys Glu
                245                 250                 255
Ala Lys Thr Gln Gly Ile Asn Phe Asp Leu Asn Asn Leu Leu Ser Lys
            260                 265                 270
Leu Pro Asn Lys Ala Lys Glu Asn Leu Asn Lys Glu Asp
        275                 280                 285

<210> SEQ ID NO 14
<211> LENGTH: 285
<212> TYPE: PRT
<213> ORGANISM: Campylobacter jejuni

<400> SEQUENCE: 14

Met Ile Gly Asp Met Asn Glu Leu Leu Leu Lys Ser Val Glu Val Leu
1               5                   10                  15
Pro Pro Leu Pro Asp Thr Val Ser Lys Leu Arg Lys Tyr Val Ser Glu
            20                  25                  30
Ala Asn Ser Asn Ile Glu Thr Met Lys Val Ala Glu Ile Ile Ser Ser
        35                  40                  45
Asp Pro Leu Met Thr Ala Lys Leu Leu Gln Leu Ala Asn Ser Pro Tyr
    50                  55                  60
Tyr Gly Phe Thr Arg Glu Ile Thr Thr Ile Asn Gln Val Ile Thr Leu
65                  70                  75                  80
Leu Gly Val Gly Asn Ile Ile Asn Ile Val Met Ala Asp Ser Ile Arg
                85                  90                  95
Asp Asn Phe Lys Ile Asp Val Ser Pro Tyr Gly Leu Asn Thr Gln Asn
            100                 105                 110
Phe Leu Lys Thr Cys Asn Glu Glu Ala Thr Phe Ile Ala Asn Trp Leu
        115                 120                 125
Asn Asp Glu Asp Lys Lys Leu Ser His Leu Leu Val Pro Cys Ala Met
    130                 135                 140
Leu Leu Arg Leu Gly Ile Val Ile Phe Ser Asn Phe Leu Ile Gln Asn
145                 150                 155                 160
His Lys Asp Lys Asp Phe Leu Ala Phe Leu Asn Lys Asn Glu Asn Leu
                165                 170                 175
Ala Leu Ala Glu Asn Glu Phe Leu Gly Val Asp His Ile Ser Phe Leu
            180                 185                 190
Gly Phe Leu Leu His Arg Trp Asn Phe Asp Asp Val Leu Ile Glu Ser
        195                 200                 205
Ile Cys Phe Val Arg Thr Pro His Ala Ala Arg Glu Lys Val Lys Lys
    210                 215                 220
Ser Ala Tyr Ala Leu Ala Ile Thr Asp His Leu Phe Ala Pro His Asp
225                 230                 235                 240
Gly Ser Ser Pro Phe Asn Ala Lys Ala Ala Val Ala Leu Leu Glu Glu
                245                 250                 255
Ala Lys Thr Gln Gly Ile Asn Phe Asp Leu Asn Asn Leu Leu Ser Lys
            260                 265                 270
```

```
Leu Pro Asn Lys Ala Lys Glu Asn Leu Asn Lys Glu Asp
        275                 280                 285
```

<210> SEQ ID NO 15
<211> LENGTH: 285
<212> TYPE: PRT
<213> ORGANISM: Campylobacter jejuni

<400> SEQUENCE: 15

```
Met Ile Gly Asp Met Asn Glu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
        50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Lys Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Lys Glu
                245                 250                 255

Ala Lys Thr Gln Gly Ile Asn Phe Asp Leu Asn Asn Leu Leu Ser Lys
            260                 265                 270

Leu Pro Asn Lys Ala Lys Glu Asn Leu Asn Lys Asp
        275                 280                 285
```

<210> SEQ ID NO 16
<211> LENGTH: 285
<212> TYPE: PRT
<213> ORGANISM: Campylobacter jejuni

<400> SEQUENCE: 16

```
Met Ile Gly Asp Met Asn Glu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30
```

```
Ala Asn Ser Asn Ile Glu Thr Met Lys Val Ala Glu Ile Ser Ser
             35                  40                  45

Asp Pro Leu Met Thr Ala Lys Leu Leu Gln Leu Ala Asn Ser Pro Tyr
 50                  55                  60

Tyr Gly Phe Thr Arg Glu Ile Thr Thr Ile Asn Gln Val Ile Thr Leu
 65                  70                  75                  80

Leu Gly Val Gly Asn Ile Ile Asn Ile Val Met Ala Asp Ser Ile Arg
                 85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
            115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
            195                 200                 205

Ile Cys Phe Val His Thr Pro His Ala Ala Arg Glu Lys Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Lys Glu
                245                 250                 255

Ala Lys Thr Gln Gly Ile Asn Phe Asp Leu Asn Asn Leu Leu Ser Lys
            260                 265                 270

Leu Pro Asn Lys Ala Lys Glu Asn Leu Asn Lys Glu Asp
            275                 280                 285

<210> SEQ ID NO 17
<211> LENGTH: 285
<212> TYPE: PRT
<213> ORGANISM: Campylobacter jejuni

<400> SEQUENCE: 17

Met Ile Gly Asp Met Asn Glu Leu Leu Leu Lys Ser Val Glu Val Leu
 1               5                  10                  15

Pro Pro Leu Pro Asp Thr Val Ser Lys Leu Arg Lys Tyr Val Ser Glu
                20                  25                  30

Ala Asn Ser Asn Ile Glu Thr Met Lys Val Ala Glu Ile Ser Ser
             35                  40                  45

Asp Pro Leu Met Met Ala Lys Leu Leu Gln Leu Ala Asn Ser Pro Tyr
 50                  55                  60

Tyr Gly Phe Thr Arg Glu Ile Thr Thr Ile Asn Gln Val Ile Thr Leu
 65                  70                  75                  80

Leu Gly Val Gly Asn Ile Ile Asn Ile Val Met Ala Asp Ser Ile Arg
                 85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
            115                 120                 125
```

```
Asn Asp Glu Asp Lys Lys Leu Ser His Leu Leu Val Pro Cys Ala Met
            130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Ser Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Lys Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Lys Glu
                245                 250                 255

Ala Lys Thr Gln Gly Ile Asn Phe Asp Leu Asn Asn Leu Leu Ser Lys
            260                 265                 270

Leu Pro Asn Lys Ala Lys Glu Asn Leu Asn Lys Glu Asp
        275                 280                 285

<210> SEQ ID NO 18
<211> LENGTH: 285
<212> TYPE: PRT
<213> ORGANISM: Campylobacter jejuni

<400> SEQUENCE: 18

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Met Ala Lys Leu Leu Gln Leu Ala Asn Ser Pro Tyr
50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
        115                 120                 125

Asn Asp Glu Asp Lys Lys Leu Ser His Leu Leu Val Pro Cys Ala Met
            130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Ser Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Lys Val Lys Lys
```

```
            210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Lys Glu
                245                 250                 255

Ala Lys Thr Gln Gly Ile Asn Phe Asp Leu Asn Asn Leu Leu Ser Lys
                260                 265                 270

Leu Pro Ser Lys Ala Lys Glu Asn Leu Asn Lys Glu Asp
            275                 280                 285

<210> SEQ ID NO 19
<211> LENGTH: 285
<212> TYPE: PRT
<213> ORGANISM: Campylobacter jejuni

<400> SEQUENCE: 19

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
                20                  25                  30

Ala Asn Ser Asn Ile Glu Thr Met Lys Val Ala Glu Ile Ile Ser Ser
            35                  40                  45

Asp Pro Leu Met Met Ala Lys Leu Leu Gln Leu Ala Asn Ser Pro Tyr
50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Val Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Val Leu Ile Glu Ser
        195                 200                 205

Ile Cys Phe Val Arg Thr Pro His Ala Ala Arg Glu Lys Val Lys Lys
        210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Lys Glu
                245                 250                 255

Ala Lys Thr Gln Gly Ile Asn Phe Asp Leu Asn Asn Leu Leu Ser Lys
                260                 265                 270

Leu Pro Asn Lys Ala Lys Glu Asn Leu Asn Lys Glu Asp
            275                 280                 285

<210> SEQ ID NO 20
<211> LENGTH: 285
```

```
<212> TYPE: PRT
<213> ORGANISM: Campylobacter jejuni

<400> SEQUENCE: 20

Met Ile Gly Asp Met Asn Glu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
        50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Thr Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Ser Gly Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Lys Glu
                245                 250                 255

Ala Lys Thr Gln Gly Ile Asn Phe Asp Leu Asn Leu Leu Ser Lys
            260                 265                 270

Leu Pro Asn Lys Ala Lys Glu Asn Leu Asn Lys Glu Asp
        275                 280                 285

<210> SEQ ID NO 21
<211> LENGTH: 285
<212> TYPE: PRT
<213> ORGANISM: Campylobacter jejuni

<400> SEQUENCE: 21

Met Ile Gly Asp Met Asn Glu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
        50                  55                  60
```

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Arg
            85                  90                  95

Asp Asn Phe Lys Ile Asp Val Ser Pro Tyr Gly Leu Asn Thr Gln Asn
        100                 105                 110

Phe Leu Lys Thr Cys Asn Glu Glu Ala Thr Phe Ile Thr Asn Trp Leu
    115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Glu Glu
                245                 250                 255

Ala Lys Thr Gln Gly Ile Asn Phe Asp Leu Asn Leu Leu Ser Lys
            260                 265                 270

Leu Pro Ser Lys Ala Lys Glu Asn Leu Asn Lys Glu Asp
        275                 280                 285

<210> SEQ ID NO 22
<211> LENGTH: 285
<212> TYPE: PRT
<213> ORGANISM: Campylobacter jejuni

<400> SEQUENCE: 22

Met Met Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Arg
            85                  90                  95

Asp Asn Phe Lys Ile Asp Val Ser Pro Tyr Gly Leu Asn Thr Gln Asn
        100                 105                 110

Phe Leu Lys Thr Cys Asn Glu Glu Ala Thr Phe Ile Thr Asn Trp Leu
    115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

```
His Lys Asp Lys Asp Phe Leu Ala Phe Leu Asn Lys Asn Glu Asn Leu
            165                 170                 175

Ala Leu Ala Glu Asn Glu Phe Leu Gly Val Asp His Ile Ser Phe Leu
        180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
        210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Glu Glu
            245                 250                 255

Ala Lys Thr Gln Gly Ile Asn Phe Asp Leu Asn Asn Leu Leu Ser Lys
            260                 265                 270

Leu Pro Ser Lys Ala Lys Glu Asn Leu Asn Lys Glu Asp
            275                 280                 285

<210> SEQ ID NO 23
<211> LENGTH: 285
<212> TYPE: PRT
<213> ORGANISM: Campylobacter jejuni

<400> SEQUENCE: 23

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Thr Asn Trp Leu
        115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
            165                 170                 175

Ala Leu Ala Glu Asn Glu Phe Leu Gly Val Asp His Ile Ser Phe Leu
        180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
        210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Glu Glu
```

Ala Lys Thr Gln Gly Ile Asn Phe Asp Leu Asn Asn Leu Leu Ser Lys
            260                 265                 270

Leu Pro Ser Lys Ala Lys Glu Asn Leu Asn Glu Glu Asp
        275                 280                 285

<210> SEQ ID NO 24
<211> LENGTH: 285
<212> TYPE: PRT
<213> ORGANISM: Campylobacter jejuni

<400> SEQUENCE: 24

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Leu Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
        115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
    210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Glu Glu
                245                 250                 255

Ala Lys Thr Gln Gly Ile Asn Phe Asp Leu Asn Asn Leu Leu Ser Lys
            260                 265                 270

Leu Pro Ser Lys Ala Lys Glu Asn Leu Asn Lys Glu Asp
        275                 280                 285

<210> SEQ ID NO 25
<211> LENGTH: 285
<212> TYPE: PRT
<213> ORGANISM: Campylobacter jejuni

<400> SEQUENCE: 25

Met Ile Gly Asp Met Asn Glu Leu Leu Leu Lys Ser Val Glu Val Leu

```
            1               5                   10                  15
        Pro Pro Leu Pro Asp Thr Val Ser Lys Leu Arg Lys Tyr Val Ser Glu
                        20                  25                  30

Ala Asn Leu Asn Ile Glu Thr Met Lys Val Ala Glu Ile Ile Ser Ser
                    35                  40                  45

Asp Pro Leu Met Thr Ala Lys Leu Leu Gln Leu Ala Asn Ser Pro Tyr
                50                  55                  60

Tyr Gly Phe Thr Arg Glu Ile Thr Thr Ile Asn Gln Val Ile Thr Leu
        65                  70                  75                  80

Leu Gly Val Gly Asn Ile Ile Asn Ile Val Thr Ala Asp Ser Ile Arg
                            85                  90                  95

Asp Asn Phe Lys Ile Asp Val Ser Pro Tyr Gly Leu Asn Thr Gln Asn
                        100                 105                 110

Phe Leu Lys Thr Cys Asn Glu Glu Ala Thr Phe Ile Thr Asn Trp Leu
                    115                 120                 125

Asn Asp Glu Asp Lys Lys Leu Ser His Leu Leu Val Pro Cys Ala Met
                130                 135                 140

Leu Leu Arg Leu Gly Ile Val Ile Phe Ser Asn Phe Leu Ile Gln Asn
        145                 150                 155                 160

His Lys Asp Lys Asp Phe Leu Ala Phe Leu Asn Lys Asn Glu Asn Leu
                        165                 170                 175

Ala Leu Ala Glu Asn Glu Phe Leu Gly Val Asp His Ile Ser Phe Leu
                    180                 185                 190

Gly Phe Leu Leu His Arg Trp Asn Phe Asp Asp Val Leu Ile Glu Ser
                195                 200                 205

Ile Cys Phe Val Arg Thr Pro His Ala Ala Arg Glu Glu Val Lys Lys
        210                 215                 220

Ser Ala Tyr Ala Leu Ala Ile Thr Asp His Leu Phe Ala Pro His Asp
        225                 230                 235                 240

Gly Ser Ser Pro Phe Asn Ala Lys Ala Val Ala Leu Leu Glu Glu
                        245                 250                 255

Ala Lys Thr Gln Gly Ile Asn Phe Asp Leu Asn Asn Leu Leu Ser Lys
                    260                 265                 270

Leu Pro Ser Lys Ala Lys Glu Asn Leu Asn Lys Glu Asp
                275                 280                 285

<210> SEQ ID NO 26
<211> LENGTH: 285
<212> TYPE: PRT
<213> ORGANISM: Campylobacter jejuni

<400> SEQUENCE: 26

Met Ile Gly Asp Met Asn Glu Leu Leu Leu Lys Ser Val Glu Val Leu
        1               5                   10                  15

Pro Pro Leu Pro Asp Thr Val Ser Lys Leu Arg Lys Tyr Val Ser Glu
                        20                  25                  30

Ala Asn Ser Asn Ile Glu Thr Met Lys Val Ala Glu Ile Ile Ser Ser
                    35                  40                  45

Asp Pro Leu Met Thr Ala Lys Leu Leu Gln Leu Ala Asn Ser Pro Tyr
                50                  55                  60

Tyr Gly Phe Thr Arg Glu Ile Thr Thr Ile Asn Gln Val Ile Thr Leu
        65                  70                  75                  80

Leu Gly Val Gly Asn Ile Ile Asn Ile Val Thr Ala Asp Ser Ile Arg
                            85                  90                  95
```

```
Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Thr Asn Trp Leu
            115                 120                 125

Asn Asp Glu Asp Lys Lys Leu Ser His Leu Leu Val Pro Cys Ala Met
            130                 135             140

Leu Leu Arg Leu Gly Ile Val Ile Phe Ser Asn Phe Leu Ile Gln Asn
145                     150                 155                 160

Tyr Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
            195                 200                 205

Ile Cys Phe Val Arg Thr Pro His Ala Ala Arg Glu Glu Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Glu Glu
                245                 250                 255

Ala Lys Thr Gln Gly Ile Asn Phe Asp Leu Asn Asn Leu Leu Ser Lys
            260                 265                 270

Leu Pro Ser Lys Ala Lys Glu Asn Leu Asn Glu Asp
            275                 280                 285

<210> SEQ ID NO 27
<211> LENGTH: 285
<212> TYPE: PRT
<213> ORGANISM: Campylobacter jejuni

<400> SEQUENCE: 27

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Thr Asn Trp Leu
            115                 120                 125

Asn Asp Glu Asp Lys Lys Leu Ser His Leu Leu Val Pro Cys Ala Met
            130                 135             140

Leu Leu Arg Leu Gly Ile Val Ile Phe Ser Asn Phe Leu Ile Gln Asn
145                     150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190
```

```
Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
    210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Glu Glu
                245                 250                 255

Ala Lys Thr Gln Gly Ile Asn Phe Asp Leu Asn Leu Leu Ser Lys
                260                 265                 270

Leu Pro Ser Lys Ala Lys Glu Asn Leu Asp Lys Glu Asp
        275                 280                 285

<210> SEQ ID NO 28
<211> LENGTH: 285
<212> TYPE: PRT
<213> ORGANISM: Campylobacter jejuni

<400> SEQUENCE: 28

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Ile Gly Asn Ile Ile Asn Ile Val Thr Ala Asp Ser Ile Arg
                85                  90                  95

Asp Ser Phe Lys Ile Asp Val Ser Pro Tyr Gly Leu Asp Thr Gln Asn
            100                 105                 110

Phe Leu Lys Thr Cys Asn Glu Glu Ala Thr Phe Ile Thr Asn Trp Leu
        115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
    210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Glu Glu
                245                 250                 255

Ala Lys Thr Gln Gly Ile Asn Phe Asp Leu Asn Leu Leu Ser Lys
                260                 265                 270

Leu Pro Ser Lys Ala Lys Glu Asn Leu Asn Lys Glu Asp
```

```
                  275                 280                 285

<210> SEQ ID NO 29
<211> LENGTH: 285
<212> TYPE: PRT
<213> ORGANISM: Campylobacter jejuni

<400> SEQUENCE: 29

Met Ile Gly Asp Met Asn Glu Leu Leu Lys Ser Val Glu Val Leu
1               5                   10                  15

Pro Pro Leu Pro Asp Thr Val Ser Lys Leu Arg Lys Tyr Val Ser Glu
                20                  25                  30

Ala Asn Ser Asn Ile Glu Thr Met Lys Val Ala Glu Ile Ile Ser Ser
                35                  40                  45

Asp Pro Leu Met Thr Ala Lys Leu Leu Gln Leu Ala Asn Ser Pro Tyr
            50                  55                  60

Tyr Gly Phe Thr Arg Glu Ile Thr Thr Ile Asn Gln Val Ile Thr Leu
65                  70                  75                  80

Leu Gly Ile Gly Asn Ile Ile Asn Ile Val Thr Ala Asp Ser Ile Arg
                    85                  90                  95

Asp Ser Phe Lys Ile Asp Val Ser Pro Tyr Gly Leu Asn Thr Gln Asn
                100                 105                 110

Phe Leu Lys Thr Cys Asn Glu Glu Ala Thr Phe Ile Thr Asn Trp Leu
            115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Val Lys Ala Ala Val Ala Leu Leu Glu Glu
                245                 250                 255

Ala Lys Thr Gln Gly Ile Asn Phe Asp Leu Asn Asn Leu Leu Ser Lys
            260                 265                 270

Leu Pro Ser Lys Ala Lys Glu Asn Leu Asn Lys Glu Asp
        275                 280                 285

<210> SEQ ID NO 30
<211> LENGTH: 283
<212> TYPE: PRT
<213> ORGANISM: Campylobacter jejuni

<400> SEQUENCE: 30

Met Asp Met Asn Glu Leu Leu Leu Lys Ser Val Glu Val Leu Pro Pro
1               5                   10                  15

Leu Pro Asp Thr Val Ser Lys Leu Arg Lys Tyr Val Ser Glu Ala Asn
                20                  25                  30

Ser Asn Ile Glu Thr Met Lys Val Ala Glu Ile Ile Ser Ser Asp Pro
```

```
                35                  40                  45
Leu Met Thr Ala Lys Leu Leu Gln Leu Ala Asn Ser Pro Tyr Tyr Gly
        50                  55                  60

Phe Thr Arg Glu Ile Thr Thr Ile Asn Gln Val Ile Thr Leu Leu Gly
 65                  70                  75                  80

Val Gly Asn Ile Ile Asn Ile Val Thr Ala Asp Ser Ile Arg Asp Asn
                    85                  90                  95

Phe Lys Ile Asp Val Ser Pro Tyr Gly Leu Asn Thr Gln Asn Phe Leu
                100                 105                 110

Lys Thr Cys Asn Glu Glu Ala Thr Phe Ile Thr Asn Trp Leu Asn Asp
            115                 120                 125

Glu Asp Lys Lys Leu Ser His Leu Leu Val Pro Cys Ala Met Leu Leu
        130                 135                 140

Arg Leu Gly Ile Val Ile Phe Ser Asn Phe Leu Ile Gln Asn His Lys
145                 150                 155                 160

Asp Lys Asp Phe Leu Ala Phe Leu Asn Lys Asn Glu Asn Leu Ala Leu
                165                 170                 175

Ala Glu Asn Glu Phe Leu Gly Val Asp His Ile Ser Phe Leu Gly Phe
            180                 185                 190

Leu Leu His Arg Trp Asn Phe Asp Asp Val Leu Ile Glu Ser Ile Cys
        195                 200                 205

Phe Val Arg Thr Pro His Ala Ala Arg Glu Glu Val Lys Lys Ser Ala
210                 215                 220

Tyr Ala Leu Ala Ile Thr Asp His Leu Phe Ala Pro His Asp Gly Ser
225                 230                 235                 240

Ser Pro Phe Asn Ala Lys Ala Val Ala Leu Leu Glu Glu Ala Lys
                245                 250                 255

Thr Gln Gly Ile Asn Phe Asp Leu Asn Asn Leu Leu Ser Lys Leu Pro
            260                 265                 270

Ser Lys Ala Lys Glu Asn Leu Asn Lys Glu Asp
        275                 280

<210> SEQ ID NO 31
<211> LENGTH: 297
<212> TYPE: PRT
<213> ORGANISM: Campylobacter jejuni
<220> FEATURE:
<221> NAME/KEY: MISC_FEATURE
<222> LOCATION: (1)..(1)
<223> OTHER INFORMATION: X can be any amino acid
<220> FEATURE:
<221> NAME/KEY: MISC_FEATURE
<222> LOCATION: (13)..(13)
<223> OTHER INFORMATION: X can be any amino acid
<220> FEATURE:
<221> NAME/KEY: MISC_FEATURE
<222> LOCATION: (17)..(17)
<223> OTHER INFORMATION: X can be any amino acid
<220> FEATURE:
<221> NAME/KEY: MISC_FEATURE
<222> LOCATION: (52)..(52)
<223> OTHER INFORMATION: X can be any amino acid
<220> FEATURE:
<221> NAME/KEY: MISC_FEATURE
<222> LOCATION: (64)..(64)
<223> OTHER INFORMATION: X can be any amino acid
<220> FEATURE:
<221> NAME/KEY: MISC_FEATURE
<222> LOCATION: (103)..(103)
<223> OTHER INFORMATION: X can be any amino acid
<220> FEATURE:
<221> NAME/KEY: MISC_FEATURE
<222> LOCATION: (156)..(156)
```

<223> OTHER INFORMATION: X can be any amino acid

<400> SEQUENCE: 31

```
Xaa Gly Ser Asp Lys Ile His His His His His Xaa Ile Gly Asp
1               5                   10                  15

Xaa Asn Glu Leu Leu Leu Lys Ser Val Glu Val Leu Pro Pro Leu Pro
            20                  25                  30

Asp Thr Val Ser Lys Leu Arg Lys Tyr Val Ser Glu Ala Asn Ser Asn
                35                  40                  45

Ile Glu Thr Xaa Lys Val Ala Glu Ile Ile Ser Ser Asp Pro Leu Xaa
            50                  55                  60

Thr Ala Lys Leu Leu Gln Leu Ala Asn Ser Pro Tyr Tyr Gly Phe Thr
65                  70                  75                  80

Arg Glu Ile Thr Thr Ile Asn Gln Val Ile Thr Leu Leu Gly Val Gly
                85                  90                  95

Asn Ile Ile Asn Ile Val Xaa Ala Asp Ser Ile Arg Asp Asn Phe Lys
                100                 105                 110

Ile Asp Val Ser Pro Tyr Gly Leu Asn Thr Gln Asn Phe Leu Lys Thr
            115                 120                 125

Cys Asn Glu Glu Ala Thr Phe Ile Ala Asn Trp Leu Asn Asp Glu Asp
130                 135                 140

Lys Lys Leu Ser His Leu Leu Val Pro Cys Ala Xaa Leu Leu Arg Leu
145                 150                 155                 160

Gly Ile Val Ile Phe Ser Asn Phe Leu Ile Gln Asn His Lys Asp Lys
                165                 170                 175

Asp Phe Leu Ala Phe Leu Asn Lys Asn Glu Asn Leu Ala Leu Ala Glu
            180                 185                 190

Asn Glu Phe Leu Gly Val Asp His Ile Ser Phe Leu Gly Phe Leu Leu
        195                 200                 205

His Arg Trp Asn Phe Asp Asp Val Leu Ile Glu Ser Ile Cys Phe Val
210                 215                 220

Arg Thr Pro His Ala Ala Arg Glu Lys Val Lys Lys Ser Ala Tyr Ala
225                 230                 235                 240

Leu Ala Ile Thr Asp His Leu Phe Ala Pro His Asp Gly Ser Ser Pro
                245                 250                 255

Phe Asn Ala Lys Ala Ala Val Ala Leu Leu Lys Glu Ala Lys Thr Gln
            260                 265                 270

Gly Ile Asn Phe Asp Leu Asn Asn Leu Leu Ser Lys Leu Pro Asn Lys
            275                 280                 285

Ala Lys Glu Asn Leu Asn Lys Glu Asp
            290                 295
```

<210> SEQ ID NO 32
<211> LENGTH: 285
<212> TYPE: PRT
<213> ORGANISM: Campylobacter jejuni

<400> SEQUENCE: 32

```
Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
                35                  40                  45

Asp Pro Leu Met Thr Ala Lys Leu Leu Gln Leu Ala Asn Ser Pro Tyr
```

Tyr Gly Phe Thr Arg Glu Ile Thr Thr Ile Asn Gln Val Ile Thr Leu
65                  70                  75                  80

Leu Gly Val Ser Asn Ile Ile Asn Ile Val Thr Ala Asp Ser Ile Arg
                85                  90                  95

Asp Ser Phe Lys Ile Asp Val Ser Pro Tyr Gly Leu Asp Thr Gln Val
            100                 105                 110

Phe Leu Arg Asn Cys Asn Glu Glu Ala Thr Phe Ile Thr Asn Trp Leu
        115                 120                 125

Asn Asp Glu Asp Lys Lys Leu Ser His Leu Leu Val Pro Cys Ala Met
130                 135                 140

Leu Leu Arg Phe Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
210                 215                 220

Ser Ala Tyr Ala Leu Ala Ile Thr Asp His Leu Phe Thr Pro His Asp
225                 230                 235                 240

Gly Ser Ser Pro Phe Asn Ala Lys Ala Ala Val Ala Leu Leu Glu Glu
                245                 250                 255

Ala Lys Thr Gln Gly Ile Asn Phe Asp Leu Asn Asn Leu Leu Ser Lys
            260                 265                 270

Leu Pro Ser Lys Ala Lys Glu Asn Leu Asp Lys Glu Asp
        275                 280                 285

<210> SEQ ID NO 33
<211> LENGTH: 287
<212> TYPE: PRT
<213> ORGANISM: Campylobacter jejuni

<400> SEQUENCE: 33

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Lys
                85                  90                  95

Asp Ser Phe Lys Ile Asp Val Ser Pro Tyr Gly Leu Asp Thr Gln Val
            100                 105                 110

Phe Leu Arg Asn Cys Asn Glu Glu Ala Thr Phe Ile Thr Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Arg Glu Lys Glu Phe Leu Thr Phe Leu Asn Glu Thr Lys Ile Glu
                165                 170                 175

Asn Ile Ala Leu Ala Glu Asn Glu Phe Leu Gly Val Asp His Ile Ser
            180                 185                 190

Phe Leu Gly Phe Leu Leu His Arg Trp Asn Phe Asp Asp Val Leu Ile
        195                 200                 205

Glu Ser Ile Cys Phe Val Arg Thr Pro His Ala Ala Arg Glu Glu Val
    210                 215                 220

Lys Lys Ser Ala Tyr Ala Leu Ala Ile Thr Asp His Leu Phe Ala Pro
225                 230                 235                 240

His Asp Gly Ser Ser Pro Phe Asn Ala Lys Ala Val Ala Leu Leu
                245                 250                 255

Glu Glu Ala Lys Thr Gln Gly Ile Asn Phe Asp Leu Asn Asn Leu Leu
                260                 265                 270

Ser Lys Leu Pro Ser Lys Ala Lys Glu Asn Leu Asn Lys Glu Asp
            275                 280                 285

<210> SEQ ID NO 34
<211> LENGTH: 287
<212> TYPE: PRT
<213> ORGANISM: Campylobacter jejuni

<400> SEQUENCE: 34

Met Ile Gly Asp Met Asn Glu Leu Leu Lys Ser Val Glu Val Leu
1               5                   10                  15

Pro Pro Leu Pro Asp Thr Val Ser Lys Leu Arg Lys Tyr Val Ser Glu
                20                  25                  30

Ala Asn Ser Asn Ile Glu Thr Met Lys Val Val Glu Ile Ile Ser Ser
            35                  40                  45

Asp Pro Leu Met Thr Ala Lys Leu Leu Gln Leu Ala Asn Ser Pro Tyr
50                  55                  60

Tyr Gly Phe Thr Arg Glu Ile Thr Thr Ile Ser Gln Val Ile Thr Leu
65                  70                  75                  80

Leu Gly Ile Gly Asn Ile Ile Asn Ile Val Thr Ala Asp Ser Ile Arg
                85                  90                  95

Asp Asn Phe Lys Ile Asp Val Ser Pro Tyr Gly Leu Asp Thr Lys Asn
            100                 105                 110

Phe Leu Lys Thr Cys Asn Glu Glu Ala Thr Phe Ile Thr Asn Trp Leu
        115                 120                 125

Asn Asp Glu Asp Lys Lys Leu Ser Phe Leu Val Pro Cys Ala Met
    130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Thr Lys Asn Glu
                165                 170                 175

Asn Ile Ala Leu Ala Glu Asn Glu Phe Leu Gly Val Asp His Ile Ser
            180                 185                 190

Phe Leu Gly Phe Leu Leu Tyr His Trp Asn Phe Asp Asp Ile Leu Ile
        195                 200                 205

Glu Ser Ile Cys Phe Val Arg Thr Pro His Ala Ala Arg Glu Glu Val
    210                 215                 220

Lys Lys Ser Ala Tyr Ala Leu Ala Ile Thr Asp His Leu Phe Ala Pro
225                 230                 235                 240

His Asp Gly Ser Ser Pro Phe Asn Thr Lys Ala Ala Ile Ala Leu Leu
            245                 250                 255

Glu Glu Ala Lys Thr Gln Gly Ile Asn Phe Asp Leu Asn Asn Leu Leu
        260                 265                 270

Ser Lys Leu Pro Ser Lys Ala Lys Glu Asn Leu Asp Lys Glu Asp
        275                 280                 285

<210> SEQ ID NO 35
<211> LENGTH: 264
<212> TYPE: PRT
<213> ORGANISM: Campylobacter jejuni

<400> SEQUENCE: 35

Met Ile Gly Asp Met Asn Glu Leu Leu Leu Lys Ser Val Glu Val Leu
1               5                  10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Lys
                85                  90                  95

Asp Ser Phe Lys Ile Asp Val Ser Pro Tyr Gly Leu Asp Thr Gln Val
            100                 105                 110

Phe Leu Arg Asn Cys Asn Glu Glu Ala Thr Phe Ile Thr Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Arg Glu Lys Glu Phe Leu Thr Phe Leu Asn Glu Thr Lys Ile Glu
            165                 170                 175

Asn Ile Ala Leu Ala Glu Asn Glu Phe Leu Gly Val Asp His Ile Ser
        180                 185                 190

Phe Leu Gly Phe Leu Leu His Arg Trp Asn Phe Asp Asp Val Leu Ile
    195                 200                 205

Glu Ser Ile Cys Phe Val Arg Thr Pro His Ala Ala Arg Glu Glu Val
210                 215                 220

Lys Lys Ser Ala Tyr Ala Leu Ala Ile Thr Asp His Leu Phe Ala Pro
225                 230                 235                 240

His Asp Gly Ser Ser Pro Phe Asn Ala Lys Ala Ala Val Ala Leu Leu
            245                 250                 255

Glu Glu Ala Lys Asn Ser Arg Asn
        260

<210> SEQ ID NO 36
<211> LENGTH: 162
<212> TYPE: PRT
<213> ORGANISM: Campylobacter jejuni

<400> SEQUENCE: 36

Met Ile Gly Asp Met Asn Glu Leu Leu Leu Lys Ser Val Glu Val Leu
1               5                  10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
        115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn
145                 150                 155                 160

Phe Lys

<210> SEQ ID NO 37
<211> LENGTH: 298
<212> TYPE: PRT
<213> ORGANISM: Campylobacter jejuni

<400> SEQUENCE: 37

Met Asn Asn Leu Leu Glu Lys Asn Ile Asn Glu Ile Asn Glu Met Leu
1               5                   10                  15

Ile Lys Ser Leu Asp Asp Leu Pro Pro Leu Pro Glu Thr Ile Gln Lys
            20                  25                  30

Leu Gln Glu Tyr Ile Ala Thr His Gly Ser Asn Ile Val Ile Asp Glu
        35                  40                  45

Val Ala Asp Ile Ile Ser Thr Asp Pro Leu Ile Thr Ala Asn Leu Leu
    50                  55                  60

His Leu Thr Asn Ser Ala Tyr Tyr Gly Phe Ser Lys Glu Ile Lys Thr
65                  70                  75                  80

Val Asn Gln Ala Leu Val Leu Leu Gly Val Ser Asn Val Lys Asn Met
                85                  90                  95

Ile Ile Ala Asp Tyr Ala Lys Ser Ser Phe Val Ile Asn Leu Ser Pro
            100                 105                 110

Tyr Gly Ile Glu Thr Asp Arg Phe Leu Thr Leu Ile His Glu Gln Thr
        115                 120                 125

Asn Phe Ile Ser Thr Trp Leu Ile Glu Glu Asp Arg Ile Leu Cys Tyr
    130                 135                 140

Asn Leu Ile Pro Cys Val Met Met Leu Arg Leu Gly Ile Met Val Phe
145                 150                 155                 160

Ser Asn Phe Leu Ile Gln Asn Ile Asp Lys Lys Phe Leu Leu His
                165                 170                 175

Leu Ser Lys Asn Asn Phe Asn Asn Ile Leu Arg Leu Glu Arg Glu Phe
            180                 185                 190

Leu Gly Val Asp His Ile Ser Phe Leu Ser Asn Leu Phe Lys Val Trp
        195                 200                 205

Asn Leu Asp Glu Asp Leu Ile Glu Ile Ile Ser Ser Leu Asp Tyr Leu
    210                 215                 220

```
Gly Ser Thr Ser Ala Lys Val Lys Lys Glu Thr Tyr Ala Leu Ala Ala
225                 230                 235                 240

Ile Glu Ala Leu Phe Ser Pro Glu Lys Asn Ala Tyr Asp Asp Phe Cys
                245                 250                 255

Val Gln Lys Ala Tyr Gln Ile Leu Lys Asp Gly Lys Ala Asn Gly Val
            260                 265                 270

Asp Phe Asn Leu Glu Asn Phe Leu Asn Lys Leu Pro Glu Lys Phe Ile
        275                 280                 285

Glu Ile Leu Ser Lys Ser Lys Glu Gln Leu
        290                 295
```

<210> SEQ ID NO 38
<211> LENGTH: 127
<212> TYPE: PRT
<213> ORGANISM: Campylobacter jejuni

<400> SEQUENCE: 38

```
Met Leu Phe Phe Gln Ile Phe Leu Tyr Lys Ile Leu Asn Lys Asn Glu
1               5                   10                  15

Asn Leu Ala Leu Ala Glu Asn Glu Phe Leu Gly Val Asp His Ile Ser
            20                  25                  30

Phe Leu Gly Phe Leu Leu His Arg Trp Asn Phe Asp Asp Val Leu Ile
        35                  40                  45

Glu Ser Ile Cys Phe Val Arg Thr Pro His Ala Ala Arg Glu Lys Val
    50                  55                  60

Lys Lys Ser Ala Tyr Ala Leu Ala Ile Thr Asp His Leu Phe Ala Pro
65                  70                  75                  80

His Asp Gly Ser Ser Pro Phe Asn Ala Lys Ala Val Ala Leu Leu
                85                  90                  95

Lys Glu Ala Lys Thr Gln Gly Ile Asn Phe Asp Leu Asn Asn Leu Leu
            100                 105                 110

Ser Lys Leu Pro Asn Lys Ala Lys Glu Asn Leu Asn Lys Glu Asp
        115                 120                 125
```

<210> SEQ ID NO 39
<211> LENGTH: 202
<212> TYPE: PRT
<213> ORGANISM: Campylobacter jejuni

<400> SEQUENCE: 39

```
Met Asn Asn Leu Leu Glu Lys Asn Ile Asn Glu Val Asn Glu Met Leu
1               5                   10                  15

Ile Lys Ser Leu Asp Asp Leu Pro Pro Leu Pro Glu Thr Ile Gln Lys
            20                  25                  30

Leu Gln Glu Tyr Ile Ala Thr His Gly Ser Asn Ile Ala Ile Asp Glu
        35                  40                  45

Val Ala Asp Ile Ile Ser Thr Asp Pro Leu Ile Thr Ala Asn Leu Leu
    50                  55                  60

His Leu Thr Asn Ser Ala Tyr Tyr Gly Phe Ser Lys Glu Ile Lys Thr
65                  70                  75                  80

Val Asn Gln Ala Leu Val Leu Leu Gly Val Asn Val Lys Asn Met
                85                  90                  95

Ile Ile Ala Asp Tyr Ala Lys Ser Ser Phe Val Ile Asn Leu Ser Pro
            100                 105                 110

Tyr Gly Ile Glu Thr Asp Arg Phe Leu Ala Leu Ile His Glu Gln Thr
        115                 120                 125
```

```
Asp Phe Ile Ser Thr Trp Leu Met Lys Glu Asp Lys Met Leu Cys Leu
            130                 135                 140

Asn Leu Ile Pro Cys Val Met Met Leu Arg Leu Gly Ile Met Val Phe
145                 150                 155                 160

Ser Asn Phe Leu Ile Gln Asn Lys Ile Asp Lys Lys Phe Leu Leu His
                165                 170                 175

Leu Ser Lys Asn Asn Phe Asn Asn Ile Leu Arg Leu Glu Arg Glu Phe
                180                 185                 190

Leu Gly Ile Glu Val Val Trp Ala Arg Asn
            195                 200
```

<210> SEQ ID NO 40
<211> LENGTH: 368
<212> TYPE: PRT
<213> ORGANISM: Campylobacter jejuni

<400> SEQUENCE: 40

```
Met Lys Glu Gln Ile Leu Glu Lys Leu Lys Thr Val Lys Tyr Pro Gly
1               5                   10                  15

Phe Glu Lys Asp Ile Val Ser Phe Asn Phe Val Lys Asp Ile Lys Ile
                20                  25                  30

Gln Asp Asp Gly Val Phe Ile Asp Ile Glu Ile Val Ser Ala Asn Pro
            35                  40                  45

Glu Val Val Asn Glu Ile Arg Lys Asn Val Thr Glu Ala Leu Ser Ser
    50                  55                  60

Leu Ala Leu Lys Asn Ile Glu Leu Asn Ile Ile Thr Pro Lys Ile Pro
65                  70                  75                  80

Glu Glu Lys Ser Asn Ser Arg Ser Gly Lys Asn Ile Ala Pro Gln Val
                85                  90                  95

Lys Asn Phe Ile Met Val Ser Ser Gly Lys Gly Val Gly Lys Ser
            100                 105                 110

Thr Thr Thr Val Asn Leu Ala Ile Ser Met Ala Lys Met Gly Lys Arg
            115                 120                 125

Val Gly Ile Leu Asp Ala Asp Ile Tyr Gly Pro Asn Ile Pro Arg Met
130                 135                 140

Leu Gly Glu Thr Lys Thr Gln Pro Glu Val Val Gly Gln Arg Leu Lys
145                 150                 155                 160

Pro Ile Leu Thr His Gly Val Tyr Met Met Ser Met Gly Val Leu Ile
                165                 170                 175

Glu Glu Gly Gln Gly Leu Met Trp Arg Gly Ala Met Ile Met Lys Ala
            180                 185                 190

Ile Glu Gln Leu Leu Ala Asp Val Ile Trp Pro Glu Leu Asp Val Leu
            195                 200                 205

Phe Leu Asp Met Pro Pro Gly Thr Gly Asp Ala Gln Ile Thr Ser Ala
210                 215                 220

Gln Ser Ile Pro Ile Thr Ala Gly Val Cys Val Ser Thr Pro Gln Thr
225                 230                 235                 240

Val Ser Leu Asp Asp Ser Lys Arg Ala Leu Asp Met Phe Asn Lys Leu
                245                 250                 255

His Ile Pro Ile Ala Gly Val Ile Glu Asn Met Ser Gly Phe Leu Cys
                260                 265                 270

Pro Asp Asn Gly Lys Glu Tyr Asp Ile Phe Gly Lys Gly Thr Ala Glu
            275                 280                 285

Asp Met Ala Lys Ala Tyr Lys Ser Glu Val Leu Ala Gln Ile Pro Ile
```

```
             290                 295                 300
Glu Met Ile Val Arg Glu Gly Asp Glu Gly Lys Pro Val Ser Phe
305                 310                 315                 320

Tyr His Pro Glu Ser Val Ser Ser Lys Arg Tyr Leu Thr Ala Ala Glu
                325                 330                 335

Lys Ile Trp Ser Phe Ile Glu Lys Ile Asn Asn Glu Gly Ala Asp
            340                 345                 350

Asn Ser Ala Ile Gln Pro Val Met Asn Gly Lys Ser Ala Cys Ser His
        355                 360                 365
```

<210> SEQ ID NO 41
<211> LENGTH: 368
<212> TYPE: PRT
<213> ORGANISM: Campylobacter jejuni

<400> SEQUENCE: 41

```
Met Lys Glu Gln Ile Leu Glu Lys Leu Lys Thr Val Lys Tyr Pro Gly
1               5                   10                  15

Phe Glu Lys Asp Ile Val Ser Phe Asn Phe Val Lys Asp Ile Lys Ile
                20                  25                  30

Gln Asp Asp Gly Val Phe Ile Asp Ile Glu Ile Val Ser Ala Asn Pro
            35                  40                  45

Glu Val Val Asn Glu Ile Arg Lys Asn Val Thr Glu Ala Leu Ser Ser
50                  55                  60

Leu Ala Leu Lys Asn Ile Glu Leu Asn Ile Ile Thr Pro Lys Ile Pro
65                  70                  75                  80

Glu Glu Lys Ser Asn Ser Arg Ser Gly Lys Asn Ile Ala Pro Gln Val
                85                  90                  95

Lys Asn Phe Ile Met Val Ser Ser Gly Lys Gly Gly Val Gly Lys Ser
            100                 105                 110

Thr Thr Thr Val Asn Leu Ala Ile Ser Met Ala Lys Met Gly Lys Arg
        115                 120                 125

Val Gly Ile Leu Asp Ala Asp Ile Tyr Gly Pro Asn Ile Pro Arg Met
130                 135                 140

Leu Gly Glu Thr Lys Thr Gln Pro Glu Val Val Gly Gln Arg Leu Lys
145                 150                 155                 160

Pro Ile Leu Thr His Gly Val Tyr Met Met Ser Met Gly Val Leu Ile
                165                 170                 175

Glu Glu Gly Gln Gly Leu Met Trp Arg Gly Ala Met Ile Met Lys Ala
            180                 185                 190

Ile Glu Gln Leu Leu Ala Asp Val Ile Trp Pro Glu Leu Asp Val Leu
        195                 200                 205

Phe Leu Asp Met Pro Pro Gly Thr Gly Asp Ala Gln Ile Thr Ser Ala
210                 215                 220

Gln Ser Ile Pro Ile Thr Ala Gly Val Cys Val Ser Thr Pro Gln Thr
225                 230                 235                 240

Val Ser Leu Asp Asp Ser Lys Arg Ala Leu Asp Met Phe Asn Lys Leu
                245                 250                 255

His Ile Pro Ile Ala Gly Val Ile Glu Asn Met Ser Gly Phe Leu Cys
            260                 265                 270

Pro Asp Asn Gly Lys Glu Tyr Asp Ile Phe Gly Lys Gly Thr Ala Glu
        275                 280                 285

Asp Met Ala Lys Ala Tyr Lys Ser Glu Val Leu Ala Gln Ile Pro Ile
290                 295                 300
```

```
Glu Met Ile Val Arg Glu Gly Gly Asp Glu Gly Lys Pro Val Ser Phe
305                 310                 315                 320

Tyr His Pro Glu Ser Val Ser Ser Lys Arg Tyr Leu Met Ala Ala Glu
                325                 330                 335

Lys Ile Trp Ser Phe Ile Glu Lys Ile Asn Asn Glu Gly Gly Ala Asp
            340                 345                 350

Asn Ser Ala Ile Gln Pro Val Met Asn Gly Lys Ser Ala Cys Ser His
        355                 360                 365

<210> SEQ ID NO 42
<211> LENGTH: 402
<212> TYPE: PRT
<213> ORGANISM: Campylobacter jejuni

<400> SEQUENCE: 42

Met Asn Leu Lys Gly Ile Phe Arg Lys Ser Phe Arg Glu Ser Lys Lys
1               5                   10                  15

Gly Tyr Leu His Leu Ile Leu Leu His Met Ile Leu Ile Tyr Leu Met
            20                  25                  30

Gln Lys Lys Ser Arg His Tyr Ile Phe Leu Lys Leu Cys Ser Tyr Leu
        35                  40                  45

Ser Lys Val Asn Met Lys Thr Val Phe Tyr Tyr Gln Ala Glu Phe Tyr
50                  55                  60

Phe Phe Tyr Ala Glu Tyr Lys Lys Ala Leu Asn Tyr Ile Asp Leu Phe
65                  70                  75                  80

Leu Glu Lys Tyr Pro Leu Asn Ile Asp Gly Lys Leu Leu Lys Ile Gln
                85                  90                  95

Leu Leu Tyr Leu Leu Gly Asp Lys Thr Lys Ala Leu Tyr Glu Leu Glu
            100                 105                 110

Lys Ile Gln Gln Glu Ser Asn Arg Leu Lys Ile Trp Met Leu Met Ser
        115                 120                 125

Lys Leu Val Asn Thr Lys Ile Asp Leu Lys Asn Met Glu Lys Leu Tyr
130                 135                 140

Leu Lys Tyr Ile Glu Lys Lys Arg Asn Ile Ser Thr Lys Ile Glu Ile
145                 150                 155                 160

Gln Lys Tyr Ile Ser Ser Ala Ala Ser Ile Glu Ala Tyr Asp Ile
                165                 170                 175

Ala Glu Tyr Tyr Leu Lys Asn Ser Leu Lys Leu His Glu Lys Phe Ser
            180                 185                 190

Leu Lys Asn Thr Lys Lys Tyr Phe Ser Lys Tyr Asp Ala Leu Ile
        195                 200                 205

Ala Leu Glu Asp Leu Ser Ser Val Phe Asn Ser Leu Asn Ile Lys Phe
210                 215                 220

Phe Leu Val Ser Gly Thr Phe Leu Gly Cys Ile Arg Glu Asn Asn Phe
225                 230                 235                 240

Ile Ser Asn Asp Tyr Asp Ile Asp Val Gly Val Trp Glu Glu Asp Phe
                245                 250                 255

Ser Asn Glu Leu Lys Ile Ala Leu Glu Gln Tyr Gly Thr Phe Tyr Ile
            260                 265                 270

His Asp Pro Lys Trp Lys Gly Gly Ile Lys Leu Lys His Ile Asn Gly
        275                 280                 285

Ile Leu Ile Asp Ile Phe Ile His Tyr Lys Asp Gly Cys Lys His Tyr
290                 295                 300

His Leu Gly Ser Ala Val Lys Trp Tyr Asn Ser Thr Phe Asp Leu Ile
305                 310                 315                 320
```

```
Lys Tyr Asp Phe Leu Gly Lys Glu Tyr Phe Gly Lys Glu Tyr Asp
                325                 330                 335

Arg Tyr Leu Ser Glu Asn Tyr Gly Asp Trp Arg Ile Pro Lys Lys Asn
                340                 345                 350

Phe Asp Asn Ile Leu Asp Thr Pro Asn Ala Val Ile Phe Asn Glu Asn
                355                 360                 365

Asn Phe Ile Leu His Leu Tyr Ser Leu Leu Met Lys Gln Tyr Ala Ile
    370                 375                 380

Asp Tyr Lys Asn Thr Ile Leu Asp Leu Leu Lys Lys Tyr Lys Phe Arg
385                 390                 395                 400

Glu Asp

<210> SEQ ID NO 43
<211> LENGTH: 402
<212> TYPE: PRT
<213> ORGANISM: Campylobacter jejuni

<400> SEQUENCE: 43

Met Asn Leu Lys Gly Ile Phe Arg Lys Ser Phe Arg Glu Thr Lys Lys
1               5                   10                  15

Trp Tyr Leu His Met Ile Leu Leu His Met Ile Leu Ile Tyr Leu Met
                20                  25                  30

Gln Lys Lys Ser Arg His Tyr Ile Phe Leu Lys Leu Cys Ile Tyr Leu
            35                  40                  45

Ser Lys Val Asn Met Lys Thr Val Phe Tyr Gln Ala Glu Phe Tyr
        50                  55                  60

Phe Phe Tyr Ala Glu Tyr Lys Lys Ala Leu Asn Tyr Ile Asp Leu Phe
65                  70                  75                  80

Leu Glu Lys Tyr Pro Leu Asn Ile Asp Gly Lys Leu Leu Lys Ile Gln
                85                  90                  95

Leu Leu Tyr Leu Leu Gly Asp Lys Thr Lys Ala Leu Tyr Glu Leu Glu
            100                 105                 110

Lys Ile Gln Gln Glu Ser Asn Arg Leu Lys Ile Trp Met Leu Met Ser
        115                 120                 125

Lys Leu Val Asn Thr Lys Ile Asp Leu Lys Asn Met Glu Lys Leu Tyr
    130                 135                 140

Leu Lys Tyr Ile Glu Lys Lys Arg Asn Ile Ser Thr Lys Ile Glu Ile
145                 150                 155                 160

Gln Lys Tyr Ile Ser Ser Ala Ala Ala Ser Ile Glu Ala Tyr Asp Ile
                165                 170                 175

Ala Glu Tyr Tyr Leu Lys Asn Ser Leu Lys Leu His Glu Lys Phe Ser
            180                 185                 190

Leu Lys Asn Thr Lys Lys Lys Tyr Phe Ser Lys Tyr Asp Ala Leu Ile
        195                 200                 205

Ala Leu Glu Asp Leu Ser Ser Val Phe Asn Ser Leu Asn Ile Lys Phe
    210                 215                 220

Phe Leu Val Ser Gly Thr Phe Leu Gly Cys Ile Arg Glu Asn Asn Phe
225                 230                 235                 240

Ile Ser Asn Asp Tyr Asp Ile Asp Val Gly Val Trp Glu Glu Asp Phe
                245                 250                 255

Ser Asn Glu Leu Lys Ile Ala Leu Glu Gln Tyr Gly Thr Phe Tyr Ile
            260                 265                 270

His Asp Pro Lys Trp Lys Gly Gly Ile Lys Leu Lys His Ile Asn Gly
        275                 280                 285
```

```
Ile Leu Ile Asp Ile Phe Ile His Tyr Lys Asp Gly Cys Lys His Tyr
    290                 295                 300

His Leu Gly Ser Ala Val Lys Trp Tyr Asn Ser Thr Phe Asp Leu Ile
305                 310                 315                 320

Lys Tyr Asp Phe Leu Gly Lys Glu Tyr Phe Gly Phe Lys Glu Tyr Asp
                325                 330                 335

Arg Tyr Leu Ser Glu Asn Tyr Gly Asp Trp Arg Ile Pro Lys Lys Asn
                340                 345                 350

Phe Asp Asn Ile Leu Asp Thr Pro Asn Ala Val Ile Phe Asn Lys Asn
                355                 360                 365

Asn Phe Ile Leu His Leu Tyr Ser Leu Leu Met Lys Gln Tyr Ala Ile
                370                 375                 380

Asp Tyr Lys Asn Thr Ile Leu Asp Leu Leu Lys Lys Tyr Lys Phe Arg
385                 390                 395                 400

Glu Asp

<210> SEQ ID NO 44
<211> LENGTH: 190
<212> TYPE: PRT
<213> ORGANISM: Campylobacter jejuni

<400> SEQUENCE: 44

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Ile Ser Phe
                20                  25                  30

Glu Gly Tyr Lys Thr Lys Asp Met Ile Gly Thr Lys Gly Glu Phe Lys
            35                  40                  45

Asn Val Glu Tyr Lys Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
                100                 105                 110

Ala Gly Glu Asn Lys Gly Val Ile Ser Ala Lys Ile Thr Met Asp Lys
            115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
                180                 185                 190

<210> SEQ ID NO 45
<211> LENGTH: 190
<212> TYPE: PRT
<213> ORGANISM: Campylobacter jejuni

<400> SEQUENCE: 45

Met Lys Lys Ile Leu Val Ser Val Leu Ser Ser Cys Leu Leu Ala Ser
1               5                   10                  15
```

```
Ala Leu Ser Ala Val Ser Phe Lys Glu Asp Ser Leu Lys Val Ser Phe
             20                  25                  30

Glu Gly Tyr Lys Thr Lys Asp Met Ile Gly Thr Lys Gly Glu Phe Lys
         35                  40                  45

Asn Val Glu Tyr Lys Phe Ser Lys Asn Ile Lys Asp Leu Ala Ser Tyr
     50                  55                  60

Leu Lys Gly Ala Lys Ala Thr Ile Lys Pro Ser Asn Ala Phe Met Gly
 65                  70                  75                  80

Glu Gly Asn Asp Ile Ile Thr Asn Asn Ile Thr Lys Val Phe Phe Pro
                 85                  90                  95

Ala Leu Leu Gly Asp Thr Asp Ile Lys Val Val Phe Gln Asp Val Ile
                100                 105                 110

Ala Gly Glu Asn Lys Gly Val Ile Ser Ala Lys Ile Thr Met Asp Lys
            115                 120                 125

Lys Ser Thr Ile Val Pro Leu Thr Tyr Thr Ile Lys Asp Asn Lys Phe
130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
            180                 185                 190

<210> SEQ ID NO 46
<211> LENGTH: 190
<212> TYPE: PRT
<213> ORGANISM: Campylobacter jejuni

<400> SEQUENCE: 46

Met Lys Lys Ile Leu Val Ser Val Leu Ser Ser Cys Leu Leu Ala Ser
 1               5                  10                  15

Ala Leu Ser Ala Val Ser Phe Lys Glu Asp Ser Leu Lys Val Ser Phe
             20                  25                  30

Glu Gly Tyr Lys Thr Lys Asp Met Ile Gly Thr Arg Gly Glu Phe Lys
         35                  40                  45

Asn Val Glu Tyr Lys Phe Ser Lys Asn Ile Lys Asp Leu Ala Ser Tyr
     50                  55                  60

Leu Lys Gly Ala Lys Ala Thr Ile Lys Pro Ser Asn Ala Phe Met Gly
 65                  70                  75                  80

Glu Gly Asn Asp Ile Ile Thr Asn Asn Ile Thr Lys Val Phe Phe Pro
                 85                  90                  95

Ala Leu Leu Gly Asp Thr Asp Ile Lys Val Val Phe Gln Asp Val Ile
                100                 105                 110

Ala Gly Glu Asn Lys Gly Val Ile Ser Ala Lys Ile Thr Met Asp Lys
            115                 120                 125

Lys Ser Thr Ile Val Pro Leu Thr Tyr Thr Ile Lys Asp Asn Lys Phe
130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
            180                 185                 190

<210> SEQ ID NO 47
```

```
<211> LENGTH: 190
<212> TYPE: PRT
<213> ORGANISM: Campylobacter jejuni

<400> SEQUENCE: 47

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Thr Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
            180                 185                 190

<210> SEQ ID NO 48
<211> LENGTH: 190
<212> TYPE: PRT
<213> ORGANISM: Campylobacter jejuni

<400> SEQUENCE: 48

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys
145                 150                 155                 160
```

Ala Leu Lys Ala Leu Ser Asp Val Ala Ala Gly His Gly Gly Ile Ser
            165                 170                 175

Trp Pro Leu Val Asp Ile Ser Phe Asn Ala Asn Leu Ala Glu
            180                 185                 190

<210> SEQ ID NO 49
<211> LENGTH: 190
<212> TYPE: PRT
<213> ORGANISM: Campylobacter jejuni

<400> SEQUENCE: 49

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

Glu Ala Lys Gly Gln Phe Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
            180                 185                 190

<210> SEQ ID NO 50
<211> LENGTH: 190
<212> TYPE: PRT
<213> ORGANISM: Campylobacter jejuni

<400> SEQUENCE: 50

Met Lys Lys Ile Leu Ala Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

```
Ala Gly Glu Asn Lys Gly Val Ile Ser Ala Lys Ile Thr Met Asp Lys
            115                 120                 125

Lys Ser Thr Ile Val Pro Leu Thr Tyr Thr Ile Lys Asp Asn Lys Phe
130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
            165                 170                 175

Trp Pro Leu Val Asp Ile Ser Phe Asn Ala Asp Leu Ala Glu
            180                 185                 190

<210> SEQ ID NO 51
<211> LENGTH: 190
<212> TYPE: PRT
<213> ORGANISM: Campylobacter jejuni

<400> SEQUENCE: 51

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Ser Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
            115                 120                 125

Lys Ser Thr Ile Val Pro Leu Thr Tyr Thr Ile Lys Asp Asn Lys Phe
130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
            165                 170                 175

Trp Pro Leu Val Asp Ile Ser Phe Asn Ala Asp Leu Ala Glu
            180                 185                 190

<210> SEQ ID NO 52
<211> LENGTH: 190
<212> TYPE: PRT
<213> ORGANISM: Campylobacter jejuni

<400> SEQUENCE: 52

Met Lys Lys Val Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Ile Lys Asp Leu Ala Ser Tyr
    50                  55                  60
```

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
130                 135                 140

Glu Ala Lys Gly Gln Phe Asp Leu His Thr Phe Lys Asn Gly Ser Lys
145                 150                 155                 160

Ala Leu Lys Ala Leu Ser Asp Val Ala Ala Gly His Gly Gly Ile Ser
            165                 170                 175

Trp Pro Leu Val Asp Ile Ser Phe Asn Ala Asp Leu Ala Glu
            180                 185                 190

<210> SEQ ID NO 53
<211> LENGTH: 190
<212> TYPE: PRT
<213> ORGANISM: Campylobacter jejuni

<400> SEQUENCE: 53

Met Lys Lys Ile Leu Ala Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Ile Lys Asp Leu Ala Ser Tyr
50                  55                  60

Leu Lys Gly Ala Lys Ala Thr Ile Glu Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
            165                 170                 175

Trp Pro Leu Val Asp Ile Ser Phe Asn Ala Asp Leu Ala Glu
            180                 185                 190

<210> SEQ ID NO 54
<211> LENGTH: 190
<212> TYPE: PRT
<213> ORGANISM: Campylobacter jejuni

<400> SEQUENCE: 54

Met Lys Lys Ile Leu Ala Ser Val Leu Ser Ser Cys Leu Leu Ala Ser
1               5                   10                  15

```
Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Ile Lys Asp Leu Ala Ser Tyr
 50                  55                  60

Leu Lys Gly Ala Lys Ala Thr Ile Lys Pro Ser Asn Ala Phe Met Gly
 65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Ala Ile
               100                 105                 110

Ala Gly Glu Asn Lys Gly Val Ile Ser Ala Lys Ile Thr Met Asp Lys
             115                 120                 125

Lys Ser Thr Ile Val Pro Leu Thr Tyr Thr Ile Lys Asp Asn Lys Phe
130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
               165                 170                 175

Trp Pro Leu Val Asp Ile Ser Phe Asn Ala Asp Leu Ala Glu
               180                 185                 190

<210> SEQ ID NO 55
<211> LENGTH: 190
<212> TYPE: PRT
<213> ORGANISM: Campylobacter jejuni

<400> SEQUENCE: 55

Met Lys Lys Ile Leu Val Ser Val Leu Ser Cys Leu Leu Ala Ser
 1               5                  10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
        35                  40                  45

Asn Val Glu Tyr Asn Phe Ser Lys Asn Ile Lys Asp Leu Ala Ser Tyr
 50                  55                  60

Leu Lys Gly Ala Lys Ala Thr Ile Lys Pro Ser Asn Ala Phe Met Gly
 65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
               100                 105                 110

Ala Gly Glu Asn Lys Gly Val Ile Ser Ala Lys Ile Thr Met Asp Lys
             115                 120                 125

Lys Ser Thr Ile Val Pro Leu Thr Tyr Thr Ile Lys Asp Asn Lys Phe
130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
               165                 170                 175

Trp Pro Leu Val Asp Ile Ser Phe Asn Ala Asn Leu Ala Glu
               180                 185                 190
```

-continued

```
<210> SEQ ID NO 56
<211> LENGTH: 190
<212> TYPE: PRT
<213> ORGANISM: Campylobacter jejuni

<400> SEQUENCE: 56
```

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Ile Lys Gly Glu Phe Lys
        35                  40                  45

Asn Val Glu Tyr Lys Phe Ser Lys Asn Thr Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
            180                 185                 190

```
<210> SEQ ID NO 57
<211> LENGTH: 190
<212> TYPE: PRT
<213> ORGANISM: Campylobacter jejuni

<400> SEQUENCE: 57
```

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Val Lys Gly Glu Phe Lys
        35                  40                  45

Asn Val Glu Tyr Lys Phe Ser Lys Asn Ile Lys Asp Leu Ala Ser Tyr
    50                  55                  60

Leu Lys Gly Ala Lys Ala Ile Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Met Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys

```
                145                 150                 155                 160
Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
                180                 185                 190

<210> SEQ ID NO 58
<211> LENGTH: 190
<212> TYPE: PRT
<213> ORGANISM: Campylobacter jejuni

<400> SEQUENCE: 58

Met Lys Lys Ile Leu Val Ser Val Leu Ser Ser Cys Leu Leu Val Ser
1               5                   10                  15

Ala Leu Ser Ala Val Ser Phe Lys Glu Asp Ser Leu Lys Val Ser Phe
                20                  25                  30

Glu Gly Tyr Lys Thr Lys Asp Met Ile Gly Ala Lys Gly Glu Phe Lys
                35                  40                  45

Asn Val Glu Tyr Lys Phe Ser Lys Asn Thr Lys Asp Leu Ala Ser Tyr
            50                  55                  60

Leu Lys Gly Ala Lys Ala Thr Ile Lys Pro Ser Asn Ala Phe Met Ser
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
                100                 105                 110

Ala Gly Glu Asn Lys Gly Val Ile Ser Ala Lys Ile Thr Met Asp Lys
                115                 120                 125

Lys Ser Thr Ile Val Pro Leu Thr Tyr Thr Ile Lys Asp Asn Lys Phe
            130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
                180                 185                 190

<210> SEQ ID NO 59
<211> LENGTH: 190
<212> TYPE: PRT
<213> ORGANISM: Campylobacter jejuni

<400> SEQUENCE: 59

Met Lys Lys Ile Leu Ala Ser Val Leu Ser Ser Cys Leu Leu Ala Ser
1               5                   10                  15

Ala Leu Ser Ala Val Ser Phe Lys Glu Asp Ser Leu Lys Val Ser Phe
                20                  25                  30

Glu Gly Tyr Lys Thr Lys Asp Met Ile Gly Thr Lys Gly Glu Phe Lys
                35                  40                  45

Asn Val Glu Tyr Lys Phe Ser Lys Asn Thr Lys Asp Leu Ala Ser Tyr
            50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
```

```
            100                 105                 110
Val Gly Glu Asn Lys Gly Val Ile Ser Ala Lys Ile Thr Met Asp Lys
                115                 120                 125

Lys Ser Thr Ile Val Pro Leu Thr Tyr Thr Ile Lys Asp Asn Lys Phe
        130                 135                 140

Glu Ala Lys Gly Gln Phe Asp Leu His Ala Phe Lys Asn Gly Ser Lys
145                 150                 155                 160

Ala Leu Lys Ala Leu Ser Asp Val Ala Thr Gly His Gly Gly Ile Ser
                165                 170                 175

Trp Pro Leu Val Asp Ile Ser Phe Asn Ala Asp Leu Thr Glu
            180                 185                 190

<210> SEQ ID NO 60
<211> LENGTH: 190
<212> TYPE: PRT
<213> ORGANISM: Campylobacter jejuni

<400> SEQUENCE: 60

Met Lys Lys Ile Val Leu Ser Ile Leu Ser Ser Cys Leu Leu Ala Ser
1               5                   10                  15

Ala Leu Ser Ala Val Ser Phe Lys Glu Asp Ser Leu Lys Ile Ser Phe
                20                  25                  30

Glu Gly Tyr Lys Thr Lys Asp Met Val Gly Val Glu Gly Glu Phe Lys
            35                  40                  45

Asn Val Glu Tyr Lys Phe Ser Lys Asn Thr Lys Asp Phe Ala Ser Tyr
        50                  55                  60

Leu Lys Gly Ala Lys Ala Thr Ile Lys Pro Ser Asn Ala Phe Met Gly
65                  70                  75                  80

Glu Gly Asn Asp Val Ile Thr Asn Asn Ile Thr Lys Val Phe Phe Pro
                85                  90                  95

Ala Leu Leu Gly Asn Ala Asp Ile Lys Val Val Phe Gln Asp Val Ile
            100                 105                 110

Val Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys
145                 150                 155                 160

Ala Leu Lys Ala Leu Ser Ala Ala Pro Gly His Gly Gly Ile Ser
                165                 170                 175

Trp Pro Leu Val Asp Ile Ser Phe Asn Ala Asp Leu Ala Glu
            180                 185                 190

<210> SEQ ID NO 61
<211> LENGTH: 190
<212> TYPE: PRT
<213> ORGANISM: Campylobacter jejuni

<400> SEQUENCE: 61

Met Lys Lys Ile Val Leu Ser Ile Leu Ser Ser Cys Leu Leu Ala Ser
1               5                   10                  15

Ala Leu Ser Ala Val Ser Phe Lys Glu Asp Ser Leu Lys Ile Ser Phe
                20                  25                  30

Glu Gly Tyr Lys Thr Lys Asp Met Val Gly Val Glu Gly Glu Phe Lys
            35                  40                  45

Asn Val Glu Tyr Lys Phe Ser Lys Asn Thr Lys Asp Phe Ala Ser Tyr
```

Leu Lys Gly Ala Lys Ala Thr Ile Lys Pro Ser Asn Ala Phe Met Gly
65                  70                  75                  80

Glu Gly Asn Asp Val Ile Thr Asn Asn Ile Thr Lys Val Phe Phe Pro
                85                  90                  95

Ala Leu Leu Gly Asn Ala Asp Ile Lys Val Val Phe Gln Asp Val Ile
                100                 105                 110

Val Gly Glu Asn Lys Gly Val Ile Ser Ala Lys Ile Thr Met Asp Lys
                115                 120                 125

Lys Ser Thr Ile Ile Pro Leu Thr Tyr Thr Ile Lys Asp Asn Lys Phe
130                 135                 140

Glu Ala Lys Gly Gln Leu Asp Leu His Thr Phe Lys Asn Gly Ser Lys
145                 150                 155                 160

Ala Leu Lys Ala Leu Ser Asp Ala Ala Pro Gly His Gly Gly Ile Ser
                165                 170                 175

Trp Pro Leu Val Asp Ile Ser Phe Asn Ala Asp Leu Ala Glu
                180                 185                 190

<210> SEQ ID NO 62
<211> LENGTH: 190
<212> TYPE: PRT
<213> ORGANISM: Campylobacter jejuni

<400> SEQUENCE: 62

Met Lys Lys Phe Leu Val Ser Val Phe Ser Phe Cys Leu Leu Ala Ser
1                   5                   10                  15

Ala Leu Ser Ala Val Ser Phe Lys Glu Asp Ser Leu Lys Ile Ser Phe
                20                  25                  30

Glu Gly Tyr Lys Thr Lys Asp Met Ile Gly Thr Lys Gly Glu Phe Lys
            35                  40                  45

Asn Val Glu Tyr Lys Phe Ser Lys Asn Thr Lys Asp Leu Ala Ser Tyr
50                  55                  60

Leu Lys Gly Ala Lys Ala Thr Ile Lys Pro Ser Asp Ala Phe Met Gly
65                  70                  75                  80

Glu Gly Leu Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
                100                 105                 110

Val Gly Glu Asn Lys Gly Val Ile Ser Ala Lys Ile Thr Met Asp Lys
                115                 120                 125

Lys Ser Thr Ile Val Pro Leu Thr Tyr Thr Ile Lys Asp Asp Lys Phe
130                 135                 140

Glu Ala Lys Gly Gln Leu Asp Leu His Thr Phe Lys Asn Ala Ser Lys
145                 150                 155                 160

Ala Leu Lys Ala Leu Ser Asp Val Ala Pro Gly His Gly Gly Ile Ser
                165                 170                 175

Trp Pro Leu Val Asp Ile Ser Phe Asn Ala Asp Leu Val Glu
                180                 185                 190

<210> SEQ ID NO 63
<211> LENGTH: 719
<212> TYPE: PRT
<213> ORGANISM: Campylobacter jejuni

<400> SEQUENCE: 63

Met Ile Asn Thr Gln Leu Ala Ser Gln Ile Ala Asn Thr Gln Lys Asn

```
              1               5                    10                        15
            Asp Leu Lys Val Asp Asn Ser Ala Ser Lys Asp Lys Thr Asn Leu Lys
                           20                  25                  30
            Asp Asn Pro Lys Glu Ala Leu Ala Gln Ala Leu Lys Gln Asn Leu Gly
                           35                  40                  45
            Leu Ser Lys Asp Ala Ser Ser Glu Glu Ile Leu Ala Lys Phe Val Gln
                           50                  55                  60
            Asn Glu Thr Gly Thr Lys Leu Lys Glu Leu Val Asn Lys Leu Leu Asp
             65                  70                  75                  80
            Gln Ile Asn Ala Gln Lys Asn Pro Asp Ser Pro Val Leu Lys Gln Gly
                           85                  90                  95
            Lys Asn Leu Asn Leu Ala Pro Asn Phe Ala Asn Glu Leu Lys Ile Leu
                          100                 105                 110
            Ser Thr Glu Leu Ala Lys Ser Asp Thr Phe Thr Gln Val Leu Asp Arg
                          115                 120                 125
            Leu Asn Gln Ile Leu Lys Pro Ala Ser Glu Ile Lys Asn Asn Asn Leu
                          130                 135                 140
            Ala Pro Leu Phe Lys Asn Ser Gly Val Phe Leu Glu Ala Lys Leu Lys
            145                 150                 155                 160
            Asp Ala Leu Asn Glu Glu Leu Leu Pro Lys Ser Phe His Ser Leu Leu
                          165                 170                 175
            Ser Thr Ile Lys Gly Leu Ser Ser Glu Lys Leu Ser Val Gln Ile Ala
                          180                 185                 190
            Gln Leu Ala Asn Thr Asn Leu Ser Pro Lys Asp Thr Leu Lys Glu Leu
                          195                 200                 205
            Lys Asn Ile Ile Asn Ser Ser Lys Asn Glu Asn Lys Gln Ile Leu Asn
                          210                 215                 220
            Gln Ser Ser Phe Lys Ala Leu Leu Asn Leu Ser Ser Lys Leu Glu Asn
            225                 230                 235                 240
            Phe Lys Asn Tyr Ile Ser Lys Asn Pro Ser His Ala Gln Glu Lys Ile
                          245                 250                 255
            Thr Pro Ile Ala Asn Lys Ile Leu Lys Glu Leu Asn Ser Ile Lys Asn
                          260                 265                 270
            Asp Phe Phe Lys Ala Leu Asn Lys Pro Glu Asn Leu Met Ile Lys Asp
                          275                 280                 285
            Pro Asn Ile Leu Lys Gln Thr Ala Thr Ala Phe Glu Lys Leu Glu Asn
                          290                 295                 300
            Thr Leu Lys Asn Ile Leu Gly Asn Gln Ala Ser Lys Ile Gln Asp Lys
            305                 310                 315                 320
            Glu Asn Ile Leu Glu Asn Leu Leu Ser Asn Lys Glu Asn Met Lys Glu
                          325                 330                 335
            Glu Lys Leu Asn His Asn Thr Lys Asn Gln Asp Glu Glu Lys His Ile
                          340                 345                 350
            Lys Ala Ser Lys Glu Asp Glu Asn Leu Asp Ser Gly Ile Lys Thr His
                          355                 360                 365
            Glu Glu Asp Thr Gln Asp Thr Lys Asn Asp Ile Gln Asn Asn Glu Thr
                          370                 375                 380
            Glu Asn Lys Pro Asp Asn Asp Ile Lys Asn Ser Thr Pro Asn Gln Glu
            385                 390                 395                 400
            Lys Ile Lys Asp Glu Lys Gln Glu Lys Ser Lys Glu Asn Ile Lys Glu
                          405                 410                 415
            Asn Pro Lys Phe Tyr Glu Thr Lys Thr Glu Asn Lys Thr Ser Ile Asn
                          420                 425                 430
```

```
Thr Asn Thr Asn Thr Ser Asn Pro Asn Thr Asn Asn Thr Gln Asn Leu
            435                 440                 445

Asn Asn Thr Gln Asn Ile Gln Ser Asn Asn Gln Thr Met Gln Asn
    450                 455                 460

Ile Phe Lys Asn Gln Glu Phe Ile Lys Gln Asn Ile Val Lys Asn Leu
465                 470                 475                 480

Ala Phe Asn Val Glu Asn Leu Asp Leu Glu Gln Val Gln Asp Leu Ser
                485                 490                 495

Lys Asn Leu Ser Asn Leu Ser Arg Arg Leu Asn Glu Ser Leu Lys Glu
            500                 505                 510

Leu Glu Pro Tyr Thr Gln Asn Ala Lys Leu Asn Gln Ala Glu Leu Lys
            515                 520                 525

Asn Leu Glu His Lys Leu Asn Leu Ser Ile Lys Asp Leu Ala Gln Ile
            530                 535                 540

Lys Pro Lys Thr Glu Gln Asp Ile Ala Glu Ser Leu His His Asp Ala
545                 550                 555                 560

Lys Ser Thr Leu Leu Gln Ile Ser Asn Leu Ala Lys Asn Glu Gly Asn
                565                 570                 575

Glu Ala Val Tyr Asn Gln Ala Asn Arg Leu Leu Ala Gln Ile Glu Ile
            580                 585                 590

Asn Gln Leu Met Ser Leu Ala Asn Asp Ser Ile Asn Thr Tyr Leu Pro
            595                 600                 605

Phe Ser Trp Asp Asp Leu Asn Asp Ser Lys Ile Met Phe Arg Arg Gly
            610                 615                 620

Lys Lys Asp Lys Phe Phe Ala Gln Ile Lys Leu Glu Phe Ala Lys Leu
625                 630                 635                 640

Gly Asp Leu Glu Ile Leu Ile Ser Leu Asn Asn Glu Lys Tyr Ile Asp
                645                 650                 655

Ile Asn Ile Met Ala Glu Asn Ile Glu Phe Arg Lys Thr Ile Tyr Glu
            660                 665                 670

Asn Ala His Glu Leu Lys Arg Asn Ile Asn Lys Ala Gly Leu Leu Ser
            675                 680                 685

Ala Asn Phe Phe Val Gly Asp Ile Ile Arg Ser Lys Phe Asp Thr Arg
            690                 695                 700

Asn Met Lys Asn Leu Asp Leu Glu Met Gly Met Asp Lys Lys Val
705                 710                 715

<210> SEQ ID NO 64
<211> LENGTH: 703
<212> TYPE: PRT
<213> ORGANISM: Campylobacter jejuni

<400> SEQUENCE: 64

Met Ile Asn Thr Gln Leu Ala Ser Gln Ile Ala Asn Thr Gln Lys Asn
1               5                   10                  15

Asp Leu Lys Val Asp Asn Ser Thr Ser Lys Asp Lys Thr Asn Leu Lys
            20                  25                  30

Asp Asn Pro Lys Glu Ala Leu Ala Gln Ala Leu Lys Gln Asn Leu Gly
        35                  40                  45

Leu Ser Lys Asp Ala Ser Ser Glu Glu Ile Leu Ala Lys Phe Val Gln
    50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
```

```
            85              90              95
Lys Asn Leu Asn Leu Ala Pro Asn Phe Ala Asn Glu Leu Lys Thr Leu
            100             105             110

Ser Thr Glu Leu Ala Lys Ser Asp Thr Phe Thr Gln Val Leu Asp Arg
            115             120             125

Leu Asn Gln Ile Leu Lys Pro Ala Ser Glu Ile Lys Asn Asn Asn Leu
130             135             140

Ala Pro Leu Phe Lys Asn Ser Gly Val Phe Leu Glu Ala Lys Leu Lys
145             150             155             160

Asp Ala Leu Asn Glu Glu Leu Leu Pro Lys Ser Phe His Ser Leu Leu
                165             170             175

Ser Thr Ile Lys Gly Leu Ser Ser Glu Lys Leu Ser Val Gln Ile Ala
                180             185             190

Gln Leu Ala Asn Thr Asn Leu Asn Pro Lys Asn Thr Leu Lys Glu Leu
            195             200             205

Lys Asn Ile Ile Asn Ser Ser Lys Asn Glu Asn Lys Gln Ile Leu Asn
            210             215             220

Gln Ser Ser Phe Lys Ala Leu Leu Asn Leu Ser Ser Lys Leu Glu Asn
225             230             235             240

Phe Lys Asn Tyr Ile Ser Lys Asn Pro Ser His Ala Gln Glu Lys Ile
                245             250             255

Thr Pro Ile Ala Asn Lys Ile Leu Lys Glu Leu Asn Ser Ile Lys Asn
                260             265             270

Asp Phe Phe Lys Ala Leu Asn Lys Pro Glu Asn Leu Met Ile Lys Asp
            275             280             285

Pro Asn Ile Leu Lys Gln Thr Ala Thr Ala Phe Glu Lys Leu Glu Asn
290             295             300

Thr Leu Lys Asn Ile Leu Gly Asn Gln Ala Ser Lys Ile Gln Asp Lys
305             310             315             320

Glu Asn Ile Leu Glu Asn Leu Leu Ser Asn Lys Glu Asn Ile Lys Glu
                325             330             335

Glu Gln Leu Asn His Asn Thr Lys Asn Gln Asp Glu Lys His Ile
            340             345             350

Lys Val Ser Lys Glu Glu Thr Leu Ala Asp Asp Ala Lys Thr Asp Ile
            355             360             365

Lys Gln Asp Val Lys Asn Glu Glu Asn Leu Pro Lys Lys Glu Val Asn
            370             375             380

Ala Asn Leu Asp Ser Ser Thr Lys Thr His Glu Glu Asn Ile Lys Glu
385             390             395             400

Asn Pro Lys Phe Tyr Glu Thr Lys Thr Glu Asn Lys Thr Ser Ile Asn
                405             410             415

Thr Asn Thr Asn Thr Ser Asn Pro Thr Asn Thr Gln Asn Leu
            420             425             430

Asn Asn Thr Gln Asn Ile Gln Ser Asn Asn Gln Thr Met Gln Asn
            435             440             445

Ile Phe Lys Asn Gln Glu Phe Ile Lys Gln Asn Ile Val Lys Asn Leu
            450             455             460

Ala Phe Asn Val Glu Asn Leu Asp Leu Glu Gln Val Gln Asp Leu Ser
465             470             475             480

Lys Asn Leu Ser Asn Leu Ser Arg Arg Leu Asn Glu Ser Leu Lys Glu
                485             490             495

Leu Glu Pro Tyr Thr Gln Asn Ala Lys Leu Asn Gln Ala Glu Leu Lys
            500             505             510
```

-continued

```
Asn Leu Glu His Lys Leu Asn Leu Ser Ile Lys Asp Leu Ala Gln Ile
            515                 520                 525

Lys Pro Lys Thr Glu Gln Asp Ile Ala Glu Ser Leu His His Asp Val
        530                 535                 540

Lys Ser Thr Leu Leu Gln Ile Ser Asn Leu Ala Lys Asn Glu Gly Asn
545                 550                 555                 560

Glu Ala Val Tyr Asn Gln Ala Asn Arg Leu Leu Ala Gln Ile Glu Ile
                565                 570                 575

Asn Gln Leu Met Ser Leu Ala Asn Asp Ser Ile Asn Thr Tyr Leu Pro
            580                 585                 590

Phe Ser Trp Asp Leu Asn Asp Ser Lys Ile Met Phe Arg Arg Gly
        595                 600                 605

Lys Lys Asp Lys Phe Ala Gln Ile Lys Leu Glu Phe Ala Lys Leu
        610                 615                 620

Gly Asp Leu Glu Ile Leu Ile Ser Leu Asn Asn Glu Lys Tyr Ile Asp
625                 630                 635                 640

Ile Asn Ile Met Ala Glu Asn Ile Glu Phe Arg Lys Thr Ile Tyr Glu
                645                 650                 655

Asn Ala His Glu Leu Lys Arg Asn Ile Asn Lys Ala Gly Leu Leu Ser
            660                 665                 670

Ala Asn Phe Phe Val Gly Asp Ile Ile Arg Ser Lys Phe Asp Thr Arg
        675                 680                 685

Asn Met Lys Asn Leu Asp Leu Glu Met Gly Met Asp Lys Lys Val
        690                 695                 700

<210> SEQ ID NO 65
<211> LENGTH: 720
<212> TYPE: PRT
<213> ORGANISM: Campylobacter jejuni

<400> SEQUENCE: 65

Met Met Ile Asn Thr Gln Leu Ala Ser Gln Ile Ala Asn Thr Gln Lys
1               5                   10                  15

Asn Asp Leu Lys Val Asp Asn Ser Ala Ser Lys Asp Lys Thr Asn Leu
            20                  25                  30

Lys Asp Asn Pro Lys Glu Ala Leu Ala Gln Ala Leu Lys Gln Asn Leu
        35                  40                  45

Gly Leu Ser Lys Asp Ala Ser Ser Glu Glu Ile Leu Ala Lys Phe Val
    50                  55                  60

Gln Asn Glu Thr Gly Thr Lys Leu Lys Glu Leu Val Asn Lys Leu Leu
65                  70                  75                  80

Asp Gln Ile Asn Ala Gln Lys Asn Pro Asp Ser Pro Val Leu Lys Gln
                85                  90                  95

Gly Lys Asn Leu Asn Leu Ala Pro Asn Phe Ala Asn Glu Leu Lys Ile
            100                 105                 110

Leu Ser Thr Glu Leu Ala Lys Ser Asp Thr Phe Thr Gln Val Leu Asp
        115                 120                 125

Arg Leu Asn Gln Ile Leu Lys Pro Ala Ser Glu Ile Lys Asn Asn Asn
    130                 135                 140

Leu Ala Pro Leu Phe Lys Asn Ser Gly Val Phe Leu Glu Ala Lys Leu
145                 150                 155                 160

Lys Asp Ala Leu Asn Glu Glu Leu Leu Pro Lys Ser Phe His Ser Leu
                165                 170                 175

Leu Ser Thr Ile Lys Gly Leu Ser Ser Glu Lys Leu Ser Val Gln Ile
```

```
            180                 185                 190
Ala Gln Leu Ala Asn Thr Asn Leu Ser Pro Lys Asp Thr Leu Lys Glu
                195                 200                 205
Leu Lys Asn Ile Ile Asn Ser Ser Lys Asn Glu Asn Lys Gln Ile Leu
            210                 215                 220
Asn Gln Ser Ser Phe Lys Ala Leu Leu Asn Leu Ser Ser Lys Leu Glu
225                 230                 235                 240
Asn Phe Lys Asn Tyr Ile Ser Lys Asn Pro Ser His Ala Gln Glu Lys
                245                 250                 255
Ile Thr Pro Ile Ala Asn Lys Ile Leu Lys Glu Leu Asn Ser Ile Lys
            260                 265                 270
Asn Asp Phe Phe Lys Ala Leu Asn Lys Pro Glu Asn Leu Met Ile Lys
            275                 280                 285
Asp Pro Asn Ile Leu Lys Gln Thr Ala Thr Ala Phe Glu Lys Leu Glu
            290                 295                 300
Asn Thr Leu Lys Asn Ile Leu Gly Asn Gln Ala Ser Lys Ile Gln Asp
305                 310                 315                 320
Lys Glu Asn Ile Leu Glu Asn Leu Leu Ser Asn Lys Glu Asn Ile Lys
                325                 330                 335
Glu Glu Lys Leu Asn His Asn Thr Lys Asn Gln Asp Glu Glu Lys His
            340                 345                 350
Ile Lys Ala Ser Lys Glu Asp Glu Asn Leu Asp Ser Gly Ile Lys Thr
            355                 360                 365
His Glu Glu Asp Thr Gln Asp Thr Lys Asn Asp Ile Gln Asn Asn Glu
            370                 375                 380
Thr Glu Asn Lys Pro Asp Asn Asp Ile Lys Asn Ser Thr Pro Asn Gln
385                 390                 395                 400
Glu Lys Ile Lys Asp Glu Lys Gln Glu Lys Ser Lys Glu Asn Ile Lys
                405                 410                 415
Glu Asn Pro Lys Phe Tyr Glu Thr Lys Thr Glu Asn Lys Thr Ser Ile
            420                 425                 430
Asn Thr Asn Thr Asn Thr Ser Asn Pro Asn Thr Asn Asn Thr Gln Asn
            435                 440                 445
Leu Asn Asn Thr Gln Asn Ile Gln Ser Asn Asn Gln Thr Met Gln
450                 455                 460
Asn Ile Phe Lys Asn Gln Glu Phe Ile Lys Gln Asn Ile Val Lys Asn
465                 470                 475                 480
Leu Ala Phe Asn Val Glu Asn Leu Asp Leu Glu Gln Val Gln Asp Leu
                485                 490                 495
Ser Lys Lys Leu Ser Asn Leu Ser Arg Arg Leu Asn Glu Ser Leu Lys
            500                 505                 510
Glu Leu Glu Pro Tyr Thr Gln Asn Ala Lys Leu Asn Gln Ala Glu Leu
            515                 520                 525
Lys Asn Leu Glu His Lys Leu Asn Leu Ser Ile Lys Asp Leu Ala Gln
            530                 535                 540
Ile Lys Pro Lys Thr Glu Gln Asp Ile Ala Glu Ser Leu His His Asp
545                 550                 555                 560
Val Lys Ser Thr Leu Leu Gln Ile Ser Asn Leu Ala Lys Asn Glu Gly
                565                 570                 575
Asn Glu Ala Val Tyr Asn Gln Ala Asn Arg Leu Leu Ala Gln Ile Glu
            580                 585                 590
Ile Asn Gln Leu Met Ser Leu Ala Asn Asp Ser Ile Asn Thr Tyr Leu
            595                 600                 605
```

```
Pro Phe Ser Trp Asp Asp Leu Asn Asp Ser Lys Ile Met Phe Arg Arg
            610                 615                 620

Gly Lys Lys Asp Lys Phe Phe Ala Gln Ile Lys Leu Glu Phe Ala Lys
625                 630                 635                 640

Leu Gly Asp Leu Glu Ile Leu Ile Ser Leu Asn Asn Glu Lys Tyr Ile
                645                 650                 655

Asp Ile Asn Ile Met Ala Glu Asn Ile Glu Phe Arg Lys Thr Ile Tyr
                660                 665                 670

Glu Asn Ala His Glu Leu Lys Arg Asn Ile Asn Lys Ala Gly Leu Leu
            675                 680                 685

Ser Ala Asn Phe Phe Val Gly Asp Ile Ile Arg Ser Lys Phe Asp Thr
            690                 695                 700

Arg Asn Met Lys Asn Leu Asp Leu Glu Met Gly Met Asp Lys Val
705                 710                 715                 720

<210> SEQ ID NO 66
<211> LENGTH: 703
<212> TYPE: PRT
<213> ORGANISM: Campylobacter jejuni

<400> SEQUENCE: 66

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
                20                  25                  30

Asp Asn Pro Lys Glu Ala Leu Ala Gln Ala Leu Lys Gln Asn Leu Gly
            35                  40                  45

Leu Ser Lys Asp Ala Ser Ser Glu Ile Leu Ala Lys Phe Val Gln
50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Thr Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Asn Pro Lys Thr Leu Lys Glu Leu
        195                 200                 205

Lys Asn Ile Ile Asn Ser Ser Lys Glu Asn Lys Gln Ile Leu Asn
    210                 215                 220

Gln Ser Ser Phe Lys Ala Leu Leu Asn Leu Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
```

-continued

```
                260                 265                 270
Asp Phe Phe Lys Ala Leu Asn Lys Pro Glu Asn Leu Met Ile Lys Asp
            275                 280                 285
Pro Asn Ile Leu Lys Gln Thr Ala Thr Ala Phe Glu Lys Leu Glu Asn
        290                 295                 300
Thr Leu Lys Asn Ile Leu Gly Asn Gln Ala Ser Lys Ile Gln Asp Lys
305                 310                 315                 320
Glu Asn Ile Leu Glu Asn Leu Leu Ser Asn Lys Glu Asn Ile Lys Glu
                325                 330                 335
Glu Gln Leu Asn His Asn Thr Lys Asn Gln Asp Glu Glu Lys His Ile
            340                 345                 350
Lys Val Ser Lys Glu Glu Thr Leu Ala Asp Asp Ala Lys Thr Asp Ile
        355                 360                 365
Lys Gln Asp Val Lys Asn Glu Glu Asn Leu Pro Lys Lys Glu Val Asn
    370                 375                 380
Ala Asn Leu Asp Ser Ser Thr Lys Thr His Glu Glu Asn Ile Lys Glu
385                 390                 395                 400
Asn Pro Lys Phe Tyr Glu Thr Lys Thr Glu Asn Lys Thr Ser Ile Asn
                405                 410                 415
Thr Asn Thr Asn Thr Ser Asn Pro Asn Thr Asn Asn Thr Gln Asn Leu
            420                 425                 430
Asn Asn Thr Gln Asn Ile Gln Ser Asn Asn Gln Thr Met Gln Asn
        435                 440                 445
Ile Phe Lys Asn Gln Glu Phe Ile Lys Gln Asn Ile Val Lys Asn Leu
    450                 455                 460
Ala Phe Asn Val Glu Asn Leu Asp Leu Glu Gln Val Gln Asp Leu Ser
465                 470                 475                 480
Lys Asn Leu Ser Asn Leu Ser Arg Arg Leu Asn Glu Ser Leu Lys Glu
                485                 490                 495
Leu Glu Pro Tyr Thr Gln Asn Ala Lys Leu Asn Gln Ala Glu Leu Lys
            500                 505                 510
Asn Leu Glu His Lys Leu Asn Leu Ser Ile Lys Asp Leu Ala Gln Ile
        515                 520                 525
Lys Pro Lys Thr Glu Gln Asp Ile Ala Glu Ser Leu His His Asp Val
    530                 535                 540
Lys Ser Thr Leu Leu Gln Ile Ser Asn Leu Ala Lys Asn Glu Gly Asn
545                 550                 555                 560
Glu Ala Val Tyr Asn Gln Ala Asn Arg Leu Leu Ala Gln Ile Glu Ile
                565                 570                 575
Asn Gln Leu Met Ser Leu Ala Asn Asp Ser Ile Asn Thr Tyr Leu Pro
            580                 585                 590
Phe Ser Trp Asp Asp Leu Asn Asp Ser Lys Ile Met Phe Arg Arg Gly
        595                 600                 605
Lys Lys Asp Lys Phe Phe Ala Gln Ile Lys Leu Glu Phe Ala Lys Leu
    610                 615                 620
Gly Asp Leu Glu Ile Leu Ile Ser Leu Asn Asn Glu Lys Tyr Ile Asp
625                 630                 635                 640
Ile Asn Ile Met Ala Glu Asn Ile Glu Phe Arg Lys Thr Ile Tyr Glu
                645                 650                 655
Asn Ala His Glu Leu Lys Arg Asn Ile Asn Lys Ala Gly Leu Leu Ser
            660                 665                 670
Ala Asn Phe Phe Val Gly Asp Ile Ile Arg Ser Lys Phe Asp Thr Arg
        675                 680                 685
```

```
Asn Met Lys Asn Leu Asp Leu Glu Met Gly Met Asp Lys Lys Val
            690                 695                 700

<210> SEQ ID NO 67
<211> LENGTH: 703
<212> TYPE: PRT
<213> ORGANISM: Campylobacter jejuni

<400> SEQUENCE: 67

Met Ile Asn Thr Gln Leu Ala Ser Gln Ile Ala Asn Thr Gln Lys Asn
  1               5                  10                  15

Asp Leu Lys Val Asp Asn Ser Ala Ser Lys Asp Lys Thr Asn Leu Lys
                 20                  25                  30

Asp Asn Pro Lys Glu Ala Leu Ala Gln Ala Leu Lys Gln Asn Leu Gly
             35                  40                  45

Leu Ser Lys Asp Ala Ser Ser Glu Glu Ile Leu Ala Lys Phe Val Gln
         50                  55                  60

Asn Glu Thr Gly Thr Lys Leu Lys Glu Leu Val Asn Lys Leu Leu Asp
 65                  70                  75                  80

Gln Ile Asn Ala Gln Lys Asn Pro Asp Ser Pro Val Leu Lys Gln Gly
                 85                  90                  95

Lys Asn Leu Asn Leu Ala Pro Asn Phe Ala Asn Glu Leu Lys Ile Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
        195                 200                 205

Lys Asn Ile Ile Asn Ser Ser Lys Asn Glu Asn Lys Gln Ile Leu Asn
210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
            260                 265                 270

Asp Phe Phe Lys Ala Leu Asn Lys Pro Glu Asn Leu Met Ile Lys Asp
        275                 280                 285

Pro Asn Ile Leu Lys Gln Thr Ala Thr Ala Phe Glu Lys Leu Glu Asn
290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Ile Lys Glu
                325                 330                 335

Glu Lys Leu Asn His Asn Thr Lys Asn Gln Asp Glu Glu Lys Tyr Ile
            340                 345                 350

Lys Val Ser Lys Glu Glu Thr Leu Ala Asp Asp Ala Lys Thr Asp Ile
```

```
                355                 360                 365
Lys Gln Asp Val Lys Asn Glu Glu Asn Leu Pro Lys Lys Glu Val Asn
        370                 375                 380

Ala Asn Leu Asp Ser Ser Thr Lys Thr His Glu Gly Asn Ile Lys Glu
385                 390                 395                 400

Asn Pro Lys Phe Tyr Glu Thr Lys Thr Glu Asn Lys Thr Ser Ile Asn
                405                 410                 415

Thr Asn Thr Asn Thr Ser Asn Pro Asn Thr Asn Thr Gln Asn Leu
        420                 425                 430

Asn Asn Thr Gln Asn Ile Gln Ser Asn Asn Gln Thr Met Gln Asn
        435                 440                 445

Ile Phe Lys Asn Gln Glu Phe Ile Lys Gln Asn Ile Val Lys Asn Leu
        450                 455                 460

Ala Phe Asn Val Glu Asn Leu Asp Leu Gln Val Gln Asp Leu Ser
465                 470                 475                 480

Lys Asn Leu Ser Asn Leu Ser Arg Arg Leu Asn Glu Ser Leu Lys Glu
                485                 490                 495

Leu Glu Pro Tyr Thr Gln Asn Ala Lys Leu Asn Gln Ala Glu Leu Lys
                500                 505                 510

Asn Leu Glu His Lys Leu Asn Leu Ser Ile Lys Asp Leu Ala Gln Ile
        515                 520                 525

Lys Pro Lys Thr Glu Gln Asp Ile Ala Glu Ser Leu His His Asp Val
        530                 535                 540

Lys Ser Thr Leu Leu Gln Ile Ser Asn Leu Ala Lys Asn Glu Gly Asn
545                 550                 555                 560

Glu Ala Val Tyr Asn Gln Ala Asn Arg Leu Leu Ala Gln Ile Glu Ile
                565                 570                 575

Asn Gln Leu Met Ser Leu Ala Asn Asp Ser Ile Asn Thr Tyr Leu Pro
        580                 585                 590

Phe Ser Trp Asp Asp Leu Asn Asp Ser Lys Ile Met Phe Arg Arg Gly
        595                 600                 605

Lys Lys Asp Lys Phe Phe Ala Gln Ile Lys Leu Glu Phe Ala Lys Leu
        610                 615                 620

Gly Asp Leu Glu Ile Leu Ile Ser Leu Asn Asn Glu Lys Tyr Ile Asp
625                 630                 635                 640

Ile Asn Ile Met Ala Glu Asn Ile Glu Phe Arg Lys Thr Ile Tyr Glu
                645                 650                 655

Asn Ala His Glu Leu Lys Arg Asn Ile Asn Lys Ala Gly Leu Leu Ser
                660                 665                 670

Ala Asn Phe Phe Val Gly Asp Ile Ile Arg Ser Lys Phe Asp Thr Arg
        675                 680                 685

Asn Met Lys Asn Leu Asp Leu Glu Met Gly Met Asp Lys Lys Val
        690                 695                 700

<210> SEQ ID NO 68
<211> LENGTH: 719
<212> TYPE: PRT
<213> ORGANISM: Campylobacter jejuni

<400> SEQUENCE: 68

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
            20                  25                  30
```

Asp Asn Pro Lys Glu Ala Leu Ala Gln Ala Leu Lys Gln Asn Leu Gly
         35                  40                  45

Leu Ser Lys Asp Ala Ser Ser Glu Glu Ile Leu Ala Lys Phe Val Gln
 50                  55                  60

Asn Glu Thr Gly Thr Lys Leu Lys Glu Leu Val Asn Lys Leu Leu Asp
 65                  70                  75                  80

Gln Ile Asn Ala Gln Lys Asn Pro Asp Ser Pro Val Leu Lys Gln Gly
                 85                  90                  95

Lys Asn Leu Asn Leu Ala Pro Asn Phe Ala Asn Glu Leu Lys Ile Leu
                100                 105                 110

Ser Thr Glu Leu Ala Lys Ser Asp Thr Phe Thr Gln Val Leu Asp Arg
         115                 120                 125

Leu Asn Gln Ile Leu Lys Pro Ala Ser Glu Ile Lys Asn Asn Asn Leu
        130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
                180                 185                 190

Gln Leu Ala Asn Thr Asn Leu Ser Pro Lys Asp Thr Leu Lys Glu Leu
        195                 200                 205

Lys Asn Ile Ile Asn Ser Ser Lys Asn Glu Asn Lys Gln Ile Leu Asn
        210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
                260                 265                 270

Asp Phe Phe Lys Ala Leu Asn Lys Pro Glu Asn Leu Met Ile Lys Asp
                275                 280                 285

Pro Asn Ile Leu Lys Gln Thr Ala Thr Ala Phe Glu Lys Leu Glu Asn
        290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Ile Lys Glu
                325                 330                 335

Glu Lys Leu Asn His Asn Thr Lys Asn Gln Asp Glu Lys His Ile
                340                 345                 350

Lys Ala Ser Lys Glu Asp Glu Asn Leu Asn Ser Gly Ile Lys Thr His
        355                 360                 365

Glu Glu Asp Thr Gln Asp Thr Lys Asn Asp Ile Gln Asn Asn Glu Thr
        370                 375                 380

Glu Asn Lys Pro Asp Asn Asp Ile Lys Asn Ser Thr Pro Asn Gln Glu
385                 390                 395                 400

Lys Ile Lys Asp Glu Lys Gln Glu Lys Ser Lys Glu Asn Ile Lys Glu
                405                 410                 415

Asn Pro Lys Phe Tyr Glu Thr Lys Thr Glu Asn Lys Thr Ser Ile Asn
                420                 425                 430

Thr Asn Thr Asn Thr Ser Asn Pro Asn Thr Asn Asn Thr Gln Asn Leu
        435                 440                 445

Asn Asn Thr Gln Asn Ile Gln Ser Asn Asn Asn Gln Thr Met Gln Asn

```
                450             455             460
Ile Phe Lys Asn Gln Glu Phe Ile Lys Gln Asn Ile Val Lys Asn Leu
465                 470                 475                 480

Ala Phe Asn Val Glu Asn Leu Asp Leu Glu Gln Val Gln Asp Leu Ser
                485                 490                 495

Lys Asn Leu Ser Asn Leu Ser Arg Arg Leu Asn Glu Ser Leu Lys Glu
                500                 505                 510

Leu Glu Pro Tyr Thr Gln Asn Ala Lys Leu Asn Gln Ala Glu Leu Lys
            515                 520                 525

Asn Leu Glu His Lys Leu Asn Leu Ser Ile Lys Asp Leu Ala Gln Ile
            530                 535                 540

Lys Pro Lys Thr Glu Gln Asp Ile Ala Glu Ser Leu His His Asp Val
545                 550                 555                 560

Lys Ser Thr Leu Leu Gln Ile Ser Asn Leu Ala Lys Asn Glu Gly Asn
                565                 570                 575

Glu Ala Val Tyr Asn Gln Ala Asn Arg Leu Leu Ala Gln Ile Glu Ile
                580                 585                 590

Asn Gln Leu Met Ser Leu Ala Asn Asp Ser Ile Asn Thr Tyr Leu Pro
            595                 600                 605

Phe Ser Trp Asp Asp Leu Asn Asp Ser Lys Ile Met Phe Arg Arg Gly
            610                 615                 620

Lys Lys Asp Lys Phe Phe Ala Gln Ile Lys Leu Glu Phe Ala Lys Leu
625                 630                 635                 640

Gly Asp Leu Glu Ile Leu Ile Ser Leu Asn Asn Glu Lys Tyr Ile Asp
                645                 650                 655

Ile Asn Ile Met Ala Glu Asn Ile Glu Phe Arg Lys Thr Ile Tyr Glu
                660                 665                 670

Asn Ala His Glu Leu Lys Arg Asn Ile Asn Lys Ala Gly Leu Leu Ser
            675                 680                 685

Ala Asn Phe Phe Val Gly Asp Ile Ile Arg Ser Lys Phe Asp Thr Arg
            690                 695                 700

Asn Met Lys Asn Leu Asp Leu Glu Met Gly Met Asp Lys Lys Val
705                 710                 715

<210> SEQ ID NO 69
<211> LENGTH: 719
<212> TYPE: PRT
<213> ORGANISM: Campylobacter jejuni

<400> SEQUENCE: 69

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
                20                  25                  30

Asp Asn Pro Lys Glu Ala Leu Ala Gln Ala Leu Lys Gln Asn Leu Gly
            35                  40                  45

Leu Ser Lys Asp Ala Ser Ser Glu Glu Ile Leu Ala Lys Phe Val Gln
        50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Ile Leu
            100                 105                 110
```

```
Ser Thr Glu Leu Ala Lys Ser Asp Thr Phe Thr Gln Val Leu Asp Arg
            115                 120                 125

Leu Asn Gln Ile Leu Lys Pro Ala Ser Glu Ile Lys Asn Asn Asn Leu
        130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
        195                 200                 205

Lys Asn Ile Ile Asn Ser Ser Lys Asn Glu Asn Lys Gln Ile Leu Asn
210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
            260                 265                 270

Asp Phe Phe Lys Ala Leu Asn Lys Pro Glu Asn Leu Met Ile Lys Asp
        275                 280                 285

Pro Asn Ile Leu Lys Gln Thr Ala Thr Ala Phe Glu Lys Leu Glu Asn
        290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Ile Lys Glu
                325                 330                 335

Glu Lys Leu Asn His Asn Thr Lys Asn Gln Asp Glu Lys His Ile
                340                 345                 350

Lys Ala Ser Lys Glu Asp Glu Asn Leu Asp Ser Gly Ile Lys Thr His
            355                 360                 365

Glu Glu Asp Thr Gln Asp Thr Lys Asn Asp Ile Gln Asn Asn Glu Thr
        370                 375                 380

Glu Asn Lys Pro Asp Asn Asp Ile Lys Asn Ser Thr Pro Asn Gln Glu
385                 390                 395                 400

Lys Ile Lys Asp Glu Lys Gln Glu Lys Ser Lys Glu Asn Ile Lys Glu
                405                 410                 415

Asn Pro Lys Phe Tyr Glu Thr Lys Thr Glu Asn Lys Thr Ser Ile Asn
            420                 425                 430

Thr Asn Thr Asn Thr Ser Asn Pro Asn Thr Asn Asn Thr Gln Asn Leu
        435                 440                 445

Asn Asn Thr Gln Asn Ile Gln Ser Asn Asn Gln Thr Met Gln Asn
        450                 455                 460

Ile Phe Lys Asn Gln Glu Phe Ile Lys Gln Asn Ile Val Lys Asn Leu
465                 470                 475                 480

Ala Phe Asn Val Glu Asn Leu Asp Leu Glu Gln Val Gln Asp Leu Ser
                485                 490                 495

Lys Asn Leu Ser Asn Leu Ser Arg Arg Leu Asn Glu Ser Leu Lys Glu
            500                 505                 510

Leu Glu Pro Tyr Thr Gln Asn Ala Lys Leu Asn Gln Ala Glu Leu Lys
        515                 520                 525

Asn Leu Glu His Lys Leu Asn Leu Ser Ile Lys Asp Leu Ala Gln Ile
```

```
                530             535             540
Lys Pro Lys Thr Glu Gln Asp Ile Ala Glu Ser Leu His His Asp Val
545             550             555             560

Lys Ser Thr Leu Leu Gln Ile Ser Asn Leu Ala Lys Asn Glu Gly Asn
                565             570             575

Glu Ala Val Tyr Asn Gln Ala Asn Arg Leu Leu Ala Gln Ile Glu Ile
            580             585             590

Asn Gln Leu Met Ser Leu Ala Asn Asp Ser Ile Asn Thr Tyr Leu Pro
            595             600             605

Phe Ser Trp Asp Asp Leu Asn Asp Ser Lys Ile Met Phe Arg Arg Gly
        610             615             620

Lys Lys Asp Lys Phe Phe Ala Gln Ile Lys Leu Glu Phe Ala Lys Leu
625             630             635             640

Gly Asp Leu Glu Ile Leu Ile Ser Leu Asn Asn Glu Lys Tyr Ile Asp
                645             650             655

Ile Asn Ile Met Ala Glu Asn Ile Glu Phe Arg Lys Thr Ile Tyr Glu
            660             665             670

Asn Ala His Glu Leu Lys Arg Asn Ile Asn Lys Ala Gly Leu Leu Ser
            675             680             685

Ala Asn Phe Phe Val Gly Asp Ile Ile Arg Ser Lys Phe Asp Thr Arg
            690             695             700

Asn Met Lys Asn Leu Asp Leu Glu Met Gly Met Asp Lys Lys Val
705             710             715

<210> SEQ ID NO 70
<211> LENGTH: 719
<212> TYPE: PRT
<213> ORGANISM: Campylobacter jejuni

<400> SEQUENCE: 70

Met Ile Asn Thr Gln Leu Ala Ser Gln Ile Ala Asn Thr Gln Lys Asn
1               5               10              15

Asp Leu Lys Val Asp Asn Ser Ala Ser Lys Asp Lys Thr Asn Leu Lys
            20              25              30

Asp Asn Pro Lys Glu Ala Leu Ala Gln Ala Leu Lys Gln Asn Leu Gly
        35              40              45

Leu Ser Lys Asp Ala Ser Ser Glu Glu Ile Leu Ala Lys Phe Val Gln
    50              55              60

Asn Glu Thr Gly Thr Lys Leu Lys Glu Leu Val Asn Lys Leu Leu Asp
65              70              75              80

Gln Ile Asn Ala Gln Lys Asn Pro Asp Ser Pro Val Leu Lys Gln Gly
            85              90              95

Lys Asn Leu Asn Leu Ala Pro Asn Phe Ala Asn Glu Leu Lys Ile Leu
            100             105             110

Ser Thr Glu Leu Ala Lys Ser Asp Thr Phe Thr Gln Val Leu Asp Arg
        115             120             125

Leu Asn Gln Ile Leu Lys Pro Ala Ser Glu Ile Lys Asn Asn Asn Leu
    130             135             140

Ala Pro Leu Phe Lys Asn Ser Gly Val Phe Leu Glu Ala Lys Leu Lys
145             150             155             160

Asp Ala Leu Asn Glu Glu Leu Leu Pro Lys Ser Phe His Ser Leu Leu
            165             170             175

Ser Thr Ile Lys Gly Leu Ser Ser Glu Lys Leu Ser Val Gln Ile Ala
            180             185             190
```

-continued

```
Gln Leu Ala Asn Thr Asn Leu Ser Pro Lys Asp Thr Leu Lys Glu Leu
            195                 200                 205
Lys Asn Ile Ile Asn Ser Ser Lys Asn Glu Asn Lys Gln Ile Leu Asn
210                 215                 220
Gln Ser Ser Phe Lys Ala Leu Leu Asn Leu Ser Ser Lys Leu Glu Asn
225                 230                 235                 240
Phe Lys Asn Tyr Ile Ser Lys Asn Pro Ser His Ala Gln Glu Lys Ile
                245                 250                 255
Thr Pro Ile Ala Asn Lys Ile Leu Lys Glu Leu Asn Ser Ile Lys Asn
            260                 265                 270
Asp Phe Phe Lys Ala Leu Asn Lys Pro Glu Asn Leu Met Ile Lys Asp
        275                 280                 285
Pro Asn Ile Leu Lys Gln Thr Ala Thr Ala Phe Glu Lys Leu Glu Asn
    290                 295                 300
Thr Leu Lys Asn Ile Leu Gly Asn Gln Ala Ser Lys Ile Gln Asp Lys
305                 310                 315                 320
Glu Asn Ile Leu Glu Asn Leu Leu Ser Asn Lys Glu Asn Met Lys Glu
                325                 330                 335
Glu Lys Leu Asn His Asn Thr Lys Asn Gln Asp Glu Glu Lys His Ile
            340                 345                 350
Lys Ala Ser Lys Glu Asp Glu Asn Leu Asp Ser Gly Ile Lys Thr His
        355                 360                 365
Glu Glu Asp Thr Gln Asp Thr Lys Asn Asp Ile Gln Asn Asn Glu Thr
    370                 375                 380
Glu Asn Lys Pro Asp Asn Asp Ile Lys Asn Ser Thr Pro Asn Gln Glu
385                 390                 395                 400
Lys Ile Lys Asp Glu Lys Gln Glu Lys Ser Lys Glu Asn Ile Lys Glu
                405                 410                 415
Asn Pro Lys Phe Tyr Glu Thr Lys Thr Glu Asn Lys Thr Ser Ile Asn
            420                 425                 430
Thr Asn Thr Asn Thr Ser Asn Pro Asn Thr Asn Thr Gln Asn Leu
        435                 440                 445
Asn Asn Thr Gln Asn Ile Gln Ser Asn Asn Gln Thr Met Gln Asn
    450                 455                 460
Ile Phe Lys Asn Gln Glu Phe Ile Lys Gln Asn Ile Val Lys Asn Leu
465                 470                 475                 480
Ala Phe Asn Val Glu Asn Leu Asp Leu Glu Gln Val Gln Asp Leu Ser
                485                 490                 495
Lys Asn Leu Ser Asn Leu Ser Arg Arg Leu Asn Glu Ser Leu Lys Glu
            500                 505                 510
Leu Glu Pro Tyr Thr Gln Asn Ala Lys Leu Asn Gln Ala Glu Leu Lys
        515                 520                 525
Asn Leu Glu His Lys Leu Asn Leu Ser Ile Lys Asp Leu Ala Gln Ile
    530                 535                 540
Lys Pro Lys Thr Glu Gln Asp Ile Ala Glu Ser Leu His His Asp Val
545                 550                 555                 560
Lys Ser Thr Leu Leu Gln Ile Ser Asn Leu Ala Lys Asn Glu Gly Asn
                565                 570                 575
Glu Ala Val Tyr Asn Gln Ala Asn Arg Leu Leu Ala Gln Ile Glu Ile
            580                 585                 590
Asn Gln Leu Met Ser Leu Ala Asn Asp Ser Ile Asn Thr Tyr Leu Pro
        595                 600                 605
Phe Ser Trp Asp Asp Leu Asn Asp Ser Lys Ile Met Phe Arg Arg Gly
```

-continued

```
            610                 615                 620
Lys Lys Asp Lys Phe Phe Ala Gln Ile Lys Leu Glu Phe Ala Lys Leu
625                 630                 635                 640

Gly Asp Leu Glu Ile Leu Ile Ser Leu Asn Asn Glu Lys Tyr Ile Asp
                    645                 650                 655

Ile Asn Ile Met Ala Glu Asn Ile Glu Phe Arg Lys Thr Ile Tyr Glu
                660                 665                 670

Asn Ala His Glu Leu Lys Arg Asn Ile Asn Lys Ala Gly Leu Leu Ser
            675                 680                 685

Ala Asn Phe Phe Val Gly Asp Ile Ile Arg Ser Lys Phe Asp Thr Arg
        690                 695                 700

Asn Met Lys Asn Leu Asp Leu Glu Met Gly Met Asp Lys Lys Val
705                 710                 715

<210> SEQ ID NO 71
<211> LENGTH: 749
<212> TYPE: PRT
<213> ORGANISM: Campylobacter jejuni

<400> SEQUENCE: 71

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
                20                  25                  30

Asp Asn Pro Lys Glu Ala Leu Ala Gln Ala Leu Lys Gln Asn Leu Gly
            35                  40                  45

Leu Ser Lys Asp Ala Ser Ser Glu Glu Ile Leu Ala Lys Phe Val Gln
50                  55                  60

Asn Glu Thr Gly Val Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Thr Leu
                100                 105                 110

Ser Thr Glu Leu Ala Lys Ser Asp Thr Phe Thr Gln Val Leu Asp Arg
            115                 120                 125

Leu Asn Gln Ile Leu Lys Pro Ala Ser Glu Ile Lys Asn Asn Asn Leu
130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
        195                 200                 205

Lys Asn Ile Ile Asn Ser Ser Lys Asn Glu Asn Lys Gln Ile Leu Asn
210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
            260                 265                 270
```

```
Asp Phe Phe Lys Ala Leu Asn Lys Pro Glu Asn Leu Met Ile Lys Asp
            275                 280                 285

Pro Asn Ile Leu Lys Gln Thr Ala Thr Ala Phe Glu Lys Leu Glu Asn
        290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Met Lys Glu
                325                 330                 335

Glu Lys Leu Asn His Asn Thr Lys Asn Gln Asp Glu Glu Lys His Ile
            340                 345                 350

Lys Ala Ser Lys Glu Glu Thr Leu Thr Asp Asp Thr Lys Thr Asp Ile
        355                 360                 365

Lys Gln Asp Ser Lys Asn Glu Glu Asn Ser His Ala Lys Glu Thr Asp
370                 375                 380

Ile Lys Glu Asp Glu Asn Leu Asp Ser Asp Ile Lys Thr His Glu Glu
385                 390                 395                 400

Asp Thr Gln Asp Thr Lys Asn Asp Ile Gln Asn Asn Glu Thr Glu Asn
                405                 410                 415

Lys Pro Asp Asn Asp Ile Lys Asn Ser Thr Pro Asn Gln Glu Lys Ile
            420                 425                 430

Lys Asp Glu Lys Gln Glu Lys Ser Lys Glu Asn Ile Lys Glu Asn Pro
        435                 440                 445

Lys Phe Tyr Glu Thr Lys Thr Glu Asn Lys Thr Ser Val Asn Thr Asn
        450                 455                 460

Thr Asn Thr Ser Asn Pro Asn Thr Asn Asn Thr Gln Asn Leu Asn Asn
465                 470                 475                 480

Ser Gln Asn Ile Gln Ser Asn Asn Asn Gln Thr Met Gln Asn Ile Phe
                485                 490                 495

Lys Asn Gln Glu Phe Ile Lys Gln Asn Ile Val Lys Asn Leu Ala Phe
            500                 505                 510

Asn Val Glu Asn Leu Asp Leu Glu Gln Val Gln Asp Leu Ser Lys Asn
        515                 520                 525

Leu Ser Asn Leu Ser Arg Arg Leu Asn Glu Ser Leu Lys Glu Leu Glu
530                 535                 540

Pro Tyr Thr Gln Asn Ala Lys Leu Asn Gln Ala Glu Leu Lys Asn Leu
545                 550                 555                 560

Glu His Lys Leu Asn Leu Ser Ile Lys Asp Leu Ala Gln Ile Lys Pro
                565                 570                 575

Lys Thr Glu Gln Asp Ile Ala Glu Ser Leu His His Asp Val Lys Ser
            580                 585                 590

Thr Leu Leu Gln Ile Ser Asn Leu Ala Lys Asn Glu Gly Asn Glu Ala
        595                 600                 605

Val Tyr Asn Gln Ala Asn Arg Leu Leu Ala Gln Ile Glu Ile Asn Gln
610                 615                 620

Leu Met Ser Leu Ala Asn Asp Ser Ile Asn Thr Tyr Leu Pro Phe Ser
625                 630                 635                 640

Trp Asp Asp Leu Asn Asp Ser Lys Ile Met Phe Arg Arg Gly Lys Lys
                645                 650                 655

Asp Lys Phe Phe Ala Gln Ile Lys Leu Glu Phe Ala Lys Leu Gly Asp
            660                 665                 670

Leu Glu Ile Leu Ile Ser Leu Asn Asn Glu Lys Tyr Ile Asp Ile Asn
        675                 680                 685

Ile Met Ala Glu Asn Ile Glu Phe Arg Lys Thr Ile Tyr Glu Asn Ala
```

```
                        690                 695                 700
His Glu Leu Lys Arg Asn Ile Asn Lys Ala Gly Leu Leu Ser Ala Asn
705                 710                 715                 720

Phe Phe Val Gly Asp Ile Ile Arg Ser Lys Phe Asp Thr Arg Asn Met
                    725                 730                 735

Lys Asn Leu Asp Leu Glu Met Gly Met Asp Lys Lys Val
                740                 745

<210> SEQ ID NO 72
<211> LENGTH: 719
<212> TYPE: PRT
<213> ORGANISM: Campylobacter jejuni

<400> SEQUENCE: 72

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
                20                  25                  30

Asp Asn Pro Lys Glu Ala Leu Ala Gln Ala Leu Lys Gln Asn Leu Gly
            35                  40                  45

Leu Ser Lys Asp Ala Ser Ser Glu Glu Ile Leu Ala Lys Phe Val Gln
50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Val Phe Lys Gln Gly
                85                  90                  95

Lys Asn Leu Asn Leu Ala Pro Asn Phe Ala Asn Glu Leu Lys Ile Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
        195                 200                 205

Lys Asn Ile Ile Asn Ser Ser Lys Asn Glu Asn Lys Gln Ile Leu Asn
210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Glu Leu Asn Ser Ile Lys Asn
            260                 265                 270

Asp Phe Phe Lys Ala Leu Asn Lys Pro Glu Asn Leu Met Ile Lys Asp
        275                 280                 285

Pro Asn Ile Leu Lys Gln Thr Ala Thr Ala Phe Glu Lys Leu Glu Asn
290                 295                 300

Thr Leu Lys Asn Ile Leu Gly Asn Gln Ala Ser Lys Ile Gln Asp Lys
305                 310                 315                 320
```

```
Glu Asn Ile Leu Glu Asn Leu Leu Ser Asn Lys Glu Asn Met Lys Glu
            325                 330                 335

Glu Lys Leu Asn His Asn Thr Lys Asn Gln Asp Glu Glu Lys His Ile
        340                 345                 350

Lys Ala Ser Lys Glu Asp Glu Asn Leu Asp Ser Gly Ile Lys Thr His
            355                 360                 365

Glu Glu Asp Thr Gln Asp Thr Lys Asn Asp Ile Gln Asn Asn Glu Thr
        370                 375                 380

Glu Asn Lys Pro Asp Asn Asp Ile Lys Asn Ser Thr Pro Asn Gln Glu
385                 390                 395                 400

Lys Ile Lys Asp Glu Lys Gln Glu Lys Ser Lys Glu Asn Ile Lys Glu
            405                 410                 415

Asn Pro Lys Phe Tyr Glu Thr Lys Thr Glu Asn Lys Thr Ser Ile Asn
            420                 425                 430

Thr Asn Thr Asn Thr Ser Asn Pro Asn Thr Asn Asn Thr Gln Asn Leu
            435                 440                 445

Asn Asn Thr Gln Asn Ile Gln Ser Asn Asn Gln Thr Met Gln Asn
450                 455                 460

Ile Phe Lys Asn Gln Glu Phe Ile Lys Gln Asn Ile Val Lys Asn Leu
465                 470                 475                 480

Ala Phe Asn Val Glu Asn Leu Asp Leu Glu Gln Val Gln Asp Leu Ser
            485                 490                 495

Lys Asn Leu Ser Asn Leu Ser Arg Arg Leu Asn Glu Ser Leu Lys Glu
            500                 505                 510

Leu Glu Pro Tyr Thr Gln Asn Ala Lys Leu Asn Gln Ala Glu Leu Lys
            515                 520                 525

Asn Leu Glu His Lys Leu Asn Leu Ser Ile Lys Asp Leu Ala Gln Ile
530                 535                 540

Lys Pro Lys Thr Glu Gln Asp Ile Ala Glu Ser Leu His His Asp Val
545                 550                 555                 560

Lys Ser Thr Leu Leu Gln Ile Ser Asn Leu Ala Lys Asn Glu Gly Asn
            565                 570                 575

Glu Ala Val Tyr Asn Gln Ala Asn Arg Leu Leu Ala Gln Ile Glu Ile
            580                 585                 590

Asn Gln Leu Met Ser Leu Ala Asn Asp Ser Ile Asn Thr Tyr Leu Pro
            595                 600                 605

Phe Ser Trp Asp Asp Leu Asn Asp Ser Lys Ile Met Phe Arg Arg Gly
            610                 615                 620

Lys Lys Asp Lys Phe Phe Ala Gln Ile Lys Leu Glu Phe Ala Lys Leu
625                 630                 635                 640

Gly Asp Leu Glu Ile Leu Ile Ser Leu Asn Asn Glu Lys Tyr Ile Asp
            645                 650                 655

Ile Asn Ile Met Ala Glu Asn Ile Glu Phe Arg Lys Thr Ile Tyr Glu
            660                 665                 670

Asn Ala His Glu Leu Lys Arg Asn Ile Asn Lys Ala Gly Leu Leu Ser
            675                 680                 685

Ala Asn Phe Phe Val Gly Asp Ile Ile Arg Ser Lys Phe Asp Thr Arg
            690                 695                 700

Asn Met Lys Asn Leu Asp Leu Glu Met Gly Met Asp Lys Lys Val
705                 710                 715

<210> SEQ ID NO 73
<211> LENGTH: 719
<212> TYPE: PRT
```

-continued

<213> ORGANISM: Campylobacter jejuni

<400> SEQUENCE: 73

```
Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
            20                  25                  30

Asp Asn Pro Lys Glu Ala Leu Ala Gln Ala Leu Lys Gln Asn Leu Gly
        35                  40                  45

Leu Ser Lys Asp Ala Ser Ser Glu Glu Ile Leu Ala Lys Phe Val Gln
    50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Ile Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
        195                 200                 205

Lys Asn Ile Ile Asn Ser Ser Lys Asn Glu Lys Gln Ile Leu Asn
    210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser Tyr Ala Gln Glu Lys Ile
                245                 250                 255

Thr Pro Ile Ala Asn Lys Ile Leu Lys Glu Leu Asn Ser Ile Lys Asn
            260                 265                 270

Asp Phe Phe Lys Ala Leu Asn Lys Pro Glu Asn Leu Met Thr Lys Asp
        275                 280                 285

Pro Asn Ile Leu Lys Gln Thr Ala Thr Ala Phe Glu Lys Leu Glu Asn
    290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Ile Lys Glu
                325                 330                 335

Glu Lys Leu Asn His Asn Thr Lys Asn Gln Asp Glu Glu Lys His Ile
            340                 345                 350

Lys Ala Ser Lys Glu Asp Glu Asn Leu Asp Ser Gly Ile Lys Thr His
        355                 360                 365

Glu Glu Asp Thr Gln Asp Thr Lys Asn Asp Ile Gln Asn Asn Glu Thr
    370                 375                 380

Glu Asn Lys Pro Asp Asn Asp Ile Lys Asn Ser Thr Pro Asn Gln Glu
385                 390                 395                 400
```

```
Lys Ile Lys Asp Glu Lys Gln Glu Lys Ser Lys Glu Asn Ile Lys Glu
                405                 410                 415
Asn Pro Lys Phe Tyr Glu Thr Lys Thr Glu Asn Lys Thr Ser Ile Asn
            420                 425                 430
Thr Asn Thr Asn Thr Ser Asn Pro Asn Thr Asn Asn Thr Gln Asn Leu
        435                 440                 445
Asn Asn Thr Gln Asn Ile Gln Ser Asn Asn Gln Thr Met Gln Asn
450                 455                 460
Ile Phe Lys Asn Gln Glu Phe Ile Lys Gln Asn Ile Val Lys Asn Leu
465                 470                 475                 480
Ala Phe Asn Val Glu Asn Leu Asp Leu Glu Gln Val Gln Asp Leu Ser
                485                 490                 495
Lys Asn Leu Ser Asn Leu Ser Arg Arg Leu Asn Glu Ser Leu Lys Glu
            500                 505                 510
Leu Glu Pro Tyr Thr Gln Asn Ala Lys Leu Asn Gln Ala Glu Leu Lys
        515                 520                 525
Asn Leu Glu His Lys Leu Asn Leu Ser Ile Lys Asp Leu Ala Gln Ile
530                 535                 540
Lys Pro Lys Thr Glu Gln Asp Ile Ala Glu Ser Leu His His Asp Val
545                 550                 555                 560
Lys Ser Thr Leu Leu Gln Ile Ser Asn Leu Ala Lys Asn Glu Gly Asn
                565                 570                 575
Glu Ala Val Tyr Asn Gln Ala Asn Arg Leu Leu Ala Gln Ile Glu Ile
            580                 585                 590
Asn Gln Leu Met Ser Leu Ala Asn Asp Ser Ile Asn Thr Tyr Leu Pro
        595                 600                 605
Phe Ser Trp Asp Asp Leu Asn Asp Ser Lys Ile Met Phe Arg Arg Gly
610                 615                 620
Lys Lys Asp Lys Phe Phe Ala Gln Ile Lys Leu Glu Phe Ala Lys Leu
625                 630                 635                 640
Gly Asp Leu Glu Ile Leu Ile Ser Leu Asn Asn Glu Lys Tyr Ile Asp
                645                 650                 655
Ile Asn Ile Met Ala Glu Asn Ile Glu Phe Arg Lys Thr Ile Tyr Glu
            660                 665                 670
Asn Ala His Glu Leu Lys Arg Asn Ile Asn Lys Ala Gly Leu Leu Ser
        675                 680                 685
Ala Asn Phe Phe Val Gly Asp Ile Ile Arg Ser Lys Phe Asp Thr Arg
690                 695                 700
Asn Met Lys Asn Leu Asp Leu Glu Met Gly Met Asp Lys Lys Val
705                 710                 715
```

<210> SEQ ID NO 74
<211> LENGTH: 323
<212> TYPE: PRT
<213> ORGANISM: Campylobacter jejuni

<400> SEQUENCE: 74

```
Met Lys Lys Tyr Ile Ser Ser Cys Leu Ala Ile Cys Cys Leu Ser Ser
1               5                   10                  15
Ala Ile Tyr Ala Asn Asp Val Lys Tyr Asp Ala Gln Lys Ile Ala Asp
            20                  25                  30
Ile Phe Tyr Gln Leu Asn Ala Asp Pro Lys Asn Pro Lys Val Lys Val
        35                  40                  45
Asn His Ala Lys Gly Phe Cys Ala Met Gly Thr Phe Glu Pro Ala Gln
50                  55                  60
```

Ser Ile Asn Lys Glu Ile Asp Val Pro Leu Leu Thr Tyr Lys Ser Leu
65                  70                  75                  80

Pro Ile Gln Val Arg Tyr Ser Leu Gly Gly Ala Phe Lys Asp Asp Lys
            85                  90                  95

Ser Lys Thr Arg Gly Met Ala Ile Arg Ile Thr Asp Pro Gln Asp Ser
        100                 105                 110

Ala Ser Trp Thr Met Val Met Leu Asn Thr Glu Ile Asn Phe Ala Lys
    115                 120                 125

Asn Leu Lys Glu Phe Gly Gln Phe Phe Glu Met Arg Leu Pro Val Asn
130                 135                 140

Gly Lys Val Asp Gln Glu Lys Ile Ser Lys Met Met Gln Glu Val Asp
145                 150                 155                 160

Ser Tyr Arg Asn Phe Ala Ala Tyr Thr Asp Lys Ile Gly Ile Ser Lys
                165                 170                 175

Ser Val Ala Asn Thr Pro Phe Phe Ser Ile His Thr Phe Tyr Phe Lys
            180                 185                 190

Gln Thr Gly Ser Glu Asn Tyr Leu Pro Ala Arg Trp Lys Leu Val Pro
        195                 200                 205

Ser Glu Gly Val Ala Tyr Leu Asn Glu Ala Gln Met Lys Ser Ala Ser
    210                 215                 220

Ser Asp Phe Leu Lys Glu Asp Phe Glu Asp Arg Val Lys Thr Asn Lys
225                 230                 235                 240

Pro Val Glu Tyr Lys Met Tyr Leu Val Tyr Ala Asn Lys Asn Asp Ile
                245                 250                 255

Ile Asn Glu Thr Thr Ala Leu Trp Glu Gly Lys His Lys Glu Ser Leu
            260                 265                 270

Val Gly Thr Phe Lys Val Asn Ala Leu Ser Glu Glu Asp Cys Asn Phe
        275                 280                 285

Asn Val Tyr Phe Pro Ser Asp Ile Pro Gln Gly Val Asn Pro Pro Gln
    290                 295                 300

Asp Pro Leu Phe Asp Val Arg Asn Glu Thr Tyr Ala Ile Thr Phe Gly
305                 310                 315                 320

Met Arg Gln

<210> SEQ ID NO 75
<211> LENGTH: 495
<212> TYPE: PRT
<213> ORGANISM: Campylobacter jejuni

<400> SEQUENCE: 75

Gln Ser Ser Phe Lys Ala Leu Leu Asn Leu Ser Ser Lys Leu Glu Asn
1               5                   10                  15

Phe Lys Asn Tyr Ile Ser Lys Asn Pro Ser His Ala Gln Glu Lys Ile
            20                  25                  30

Thr Pro Ile Ala Asn Lys Ile Leu Lys Glu Leu Asn Ser Ile Lys Asn
        35                  40                  45

Asp Phe Phe Lys Ala Leu Asn Lys Pro Glu Asn Leu Met Ile Lys Asp
    50                  55                  60

Pro Asn Ile Leu Lys Gln Thr Thr Ala Phe Glu Lys Leu Glu Asn
65                  70                  75                  80

Thr Leu Lys Asn Ile Leu Gly Asn Gln Ala Ser Lys Ile Gln Asp Lys
            85                  90                  95

Glu Asn Ile Leu Glu Asn Leu Leu Ser Asn Lys Glu Asn Met Lys Glu
        100                 105                 110

Glu Lys Leu Asn His Asn Thr Lys Asn Gln Asp Glu Lys His Ile
            115                 120                 125

Lys Ala Ser Lys Glu Asp Glu Asn Leu Asp Ser Gly Ile Lys Thr His
            130                 135                 140

Glu Glu Asp Thr Gln Asp Thr Lys Asn Asp Ile Gln Asn Asn Glu Thr
145                 150                 155                 160

Glu Asn Lys Pro Asp Asn Asp Ile Lys Asn Ser Thr Pro Asn Gln Glu
                165                 170                 175

Lys Ile Lys Asp Glu Lys Gln Glu Lys Ser Lys Glu Asn Ile Lys Glu
            180                 185                 190

Asn Pro Lys Phe Tyr Glu Thr Lys Thr Glu Asn Lys Thr Ser Ile Asn
            195                 200                 205

Thr Asn Thr Asn Thr Ser Asn Pro Asn Thr Asn Thr Gln Asn Leu
210                 215                 220

Asn Asn Thr Gln Asn Ile Gln Ser Asn Asn Gln Thr Met Gln Asn
225                 230                 235                 240

Ile Phe Lys Asn Gln Glu Phe Ile Lys Gln Asn Ile Val Lys Asn Leu
                245                 250                 255

Ala Phe Asn Val Glu Asn Leu Asp Leu Glu Gln Val Gln Asp Leu Ser
            260                 265                 270

Lys Asn Leu Ser Asn Leu Ser Arg Arg Leu Asn Glu Ser Leu Lys Glu
            275                 280                 285

Leu Glu Pro Tyr Thr Gln Asn Ala Lys Leu Asn Gln Ala Glu Leu Lys
            290                 295                 300

Asn Leu Glu His Lys Leu Asn Leu Ser Ile Lys Asp Leu Ala Gln Ile
305                 310                 315                 320

Lys Pro Lys Thr Glu Gln Asp Ile Ala Glu Ser Leu His His Asp Val
            325                 330                 335

Lys Ser Thr Leu Leu Gln Ile Ser Asn Leu Ala Lys Asn Glu Gly Asn
            340                 345                 350

Glu Ala Val Tyr Asn Gln Ala Asn Arg Leu Leu Ala Gln Ile Glu Ile
            355                 360                 365

Asn Gln Leu Met Ser Leu Ala Asn Asp Ser Ile Asn Thr Tyr Leu Pro
            370                 375                 380

Phe Ser Trp Asp Asp Leu Asn Asp Ser Lys Ile Met Phe Arg Arg Gly
385                 390                 395                 400

Lys Lys Asp Lys Phe Phe Ala Gln Ile Lys Leu Glu Phe Ala Lys Leu
                405                 410                 415

Gly Asp Leu Glu Ile Leu Ile Ser Leu Asn Asn Gly Lys Tyr Ile Asp
            420                 425                 430

Ile Asn Ile Met Ala Glu Asn Ile Glu Phe Arg Lys Thr Ile Tyr Glu
            435                 440                 445

Asn Ala His Glu Leu Lys Arg Asn Ile Asn Lys Ala Gly Leu Leu Ser
            450                 455                 460

Ala Asn Phe Phe Val Gly Asp Ile Ile Arg Ser Lys Phe Asp Thr Arg
465                 470                 475                 480

Asn Met Lys Asn Leu Asp Leu Glu Met Gly Met Asp Lys Lys Val
                485                 490                 495

<210> SEQ ID NO 76
<211> LENGTH: 749
<212> TYPE: PRT
<213> ORGANISM: Campylobacter jejuni

<400> SEQUENCE: 76

```
Met Ile Asn Thr Gln Leu Ala Ser Gln Ile Ala Asn Thr Gln Lys Asn
1               5                   10                  15

Asp Leu Lys Val Asp Asn Ser Thr Ser Lys Asp Lys Thr Asn Leu Lys
            20                  25                  30

Asp Asn Pro Lys Glu Ala Leu Ala Gln Ala Leu Lys Gln Asn Leu Gly
        35                  40                  45

Leu Ser Lys Asp Ala Ser Ser Glu Glu Ile Leu Ala Lys Phe Val Gln
    50                  55                  60

Asn Glu Thr Gly Ile Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Ile Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
    195                 200                 205

Lys Asn Ile Ile Asn Ser Lys Ile Glu Asn Lys Gln Ile Leu Asn
210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
            260                 265                 270

Asp Phe Phe Lys Ala Leu Asn Lys Pro Glu Asn Leu Met Ile Lys Asp
    275                 280                 285

Pro Asn Ile Leu Lys Gln Thr Ala Thr Ala Phe Glu Lys Leu Glu Asn
290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Met Lys Glu
                325                 330                 335

Glu Lys Leu Asn His Asn Thr Lys Asn Gln Asp Glu Lys His Ile
            340                 345                 350

Lys Ala Ser Lys Glu Glu Thr Leu Thr Asp Asp Thr Lys Thr Asp Ile
355                 360                 365

Lys Gln Asp Ser Lys Asn Glu Glu Asn Ser His Ala Lys Glu Thr Asp
    370                 375                 380

Ile Lys Glu Asp Glu Asn Leu Asp Ser Asp Ile Lys Thr His Glu Glu
385                 390                 395                 400

Asp Thr Gln Asp Thr Lys Asn Asp Ile Gln Asn Asn Glu Thr Glu Asn
                405                 410                 415
```

-continued

```
Lys Pro Asp Asn Asp Ile Lys Asn Ser Thr Pro Asn Gln Glu Lys Ile
                420                 425                 430

Lys Asp Gly Lys Gln Glu Lys Ser Lys Glu Asn Ile Lys Glu Asn Pro
            435                 440                 445

Lys Phe Tyr Glu Thr Lys Thr Glu Asn Lys Thr Ser Ile Asn Thr Asn
        450                 455                 460

Thr Asn Thr Ser Asn Pro Asn Thr Asn Thr Gln Asn Leu Asn Asn
465                 470                 475                 480

Ser Gln Asn Ile Gln Ser Asn Asn Gln Thr Met Gln Asn Ile Phe
                485                 490                 495

Lys Asn Gln Glu Phe Ile Lys Gln Asn Ile Val Lys Asn Leu Ala Phe
            500                 505                 510

Asn Val Glu Asn Leu Asp Leu Glu Gln Val Gln Asp Leu Ser Lys Asn
        515                 520                 525

Leu Ser Asn Leu Ser Arg Arg Leu Asn Glu Ser Leu Lys Glu Leu Glu
530                 535                 540

Pro Tyr Thr Gln Asn Ala Lys Leu Asn Gln Ala Glu Leu Lys Asn Leu
545                 550                 555                 560

Glu His Lys Leu Asn Leu Ser Thr Lys Asp Leu Ala Gln Ile Lys Pro
                565                 570                 575

Lys Thr Glu Gln Asp Ile Ala Glu Ser Leu His His Asp Val Lys Ser
            580                 585                 590

Thr Leu Leu Gln Ile Ser Asn Leu Ala Lys Asn Glu Gly Asn Glu Ala
        595                 600                 605

Ile Tyr Asn Gln Ala Asn Arg Leu Leu Ala Gln Ile Glu Ile Asn Gln
    610                 615                 620

Leu Met Ser Leu Ala Asn Asp Ser Ile Asn Thr Tyr Leu Pro Phe Ser
625                 630                 635                 640

Trp Asp Asp Leu Asn Asp Ser Lys Ile Met Phe Arg Arg Gly Lys Lys
                645                 650                 655

Asp Lys Phe Phe Ala Gln Ile Lys Leu Glu Phe Ala Lys Leu Gly Asp
            660                 665                 670

Leu Glu Ile Leu Ile Ser Leu Asn Asn Glu Lys Tyr Ile Asp Ile Asn
        675                 680                 685

Ile Met Ala Glu Asn Ile Glu Phe Arg Lys Thr Ile Tyr Glu Asn Ala
    690                 695                 700

His Glu Leu Lys Arg Asn Ile Asn Lys Ala Gly Leu Leu Ser Ala Asn
705                 710                 715                 720

Phe Phe Val Gly Asp Ile Ile Arg Ser Lys Phe Asp Thr Arg Asn Met
                725                 730                 735

Lys Asn Leu Asp Leu Glu Met Gly Met Asp Lys Lys Val
            740                 745
```

<210> SEQ ID NO 77
<211> LENGTH: 749
<212> TYPE: PRT
<213> ORGANISM: Campylobacter jejuni

<400> SEQUENCE: 77

```
Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
            20                  25                  30

Asp Asn Pro Lys Glu Ala Leu Ala Gln Ala Leu Lys Gln Asn Leu Gly
```

-continued

```
                35                  40                  45
Leu Ser Lys Asp Ala Ser Ser Glu Glu Ile Leu Ala Lys Phe Val Gln
 50                  55                  60
Asn Glu Thr Gly Thr Lys Leu Lys Glu Leu Val Asn Lys Leu Leu Asp
 65                  70                  75                  80
Gln Ile Asn Ala Gln Lys Asn Pro Asp Ser Pro Val Leu Lys Gln Gly
                 85                  90                  95
Lys Asn Leu Asn Leu Ala Pro Asn Phe Ala Asn Glu Leu Lys Thr Leu
                100                 105                 110
Ser Thr Glu Leu Ala Lys Ser Asp Thr Phe Thr Gln Val Leu Asp Arg
                115                 120                 125
Leu Asn Gln Ile Leu Lys Pro Ala Ser Glu Ile Lys Asn Asn Asn Leu
130                 135                 140
Ala Pro Leu Phe Lys Asn Ser Gly Val Phe Leu Glu Ala Lys Leu Lys
145                 150                 155                 160
Asp Ala Leu Asn Glu Glu Leu Leu Pro Lys Ser Phe His Ser Leu Leu
                165                 170                 175
Ser Thr Ile Lys Gly Leu Ser Ser Glu Lys Leu Ser Val Gln Ile Ala
                180                 185                 190
Gln Leu Ala Asn Thr Asn Leu Ser Pro Lys Asp Thr Leu Lys Glu Leu
                195                 200                 205
Lys Asn Ile Ile Asn Ser Ser Lys Ile Glu Asn Lys Gln Ile Leu Asn
210                 215                 220
Gln Ser Ser Phe Lys Ala Leu Leu Asn Leu Ser Ser Lys Leu Glu Asn
225                 230                 235                 240
Phe Lys Asn Tyr Ile Ser Lys Asn Pro Ser His Ala Gln Glu Lys Ile
                245                 250                 255
Thr Pro Ile Ala Asn Lys Ile Leu Lys Glu Leu Asn Ser Ile Lys Asn
                260                 265                 270
Asp Phe Phe Lys Ala Leu Asn Lys Pro Glu Asn Leu Met Ile Lys Asp
                275                 280                 285
Pro Asn Ile Leu Lys Gln Thr Ala Thr Ala Phe Glu Lys Leu Glu Asn
290                 295                 300
Thr Leu Lys Asn Ile Leu Gly Asn Gln Ala Ser Lys Ile Gln Asp Lys
305                 310                 315                 320
Glu Asn Ile Leu Glu Asn Leu Leu Ser Asn Lys Glu Asn Met Lys Glu
                325                 330                 335
Glu Lys Leu Asn His Asn Thr Lys Asn Gln Asp Glu Lys His Ile
                340                 345                 350
Lys Ala Ser Lys Glu Glu Thr Leu Thr Asp Asp Thr Lys Thr Asp Ile
                355                 360                 365
Lys Gln Asp Leu Lys Asn Glu Asn Ser His Ala Lys Glu Thr Asp
                370                 375                 380
Ile Lys Glu Asp Glu Asn Leu Asp Ser Asp Ile Lys Thr His Glu Glu
385                 390                 395                 400
Asp Thr Gln Asp Thr Lys Asn Asp Ile Gln Asn Asn Glu Thr Glu Asn
                405                 410                 415
Lys Pro Asp Asn Asp Ile Lys Asn Phe Thr Pro Asn Gln Glu Lys Ile
                420                 425                 430
Lys Asp Glu Lys Gln Glu Lys Ser Lys Glu Asn Ile Lys Glu Asn Pro
                435                 440                 445
Lys Phe Tyr Glu Thr Lys Thr Glu Asn Lys Thr Ser Ile Asn Thr Asn
450                 455                 460
```

-continued

```
Thr Asn Thr Ser Asn Pro Asn Thr Asn Thr Gln Asn Leu Asn Asn
465                 470                 475                 480

Ser Gln Asn Ile Gln Ser Asn Asn Gln Thr Met Gln Asn Ile Phe
            485                 490                 495

Lys Asn Gln Glu Phe Ile Lys Gln Asn Ile Ile Lys Asn Leu Ala Phe
                500                 505                 510

Asn Val Glu Asn Leu Asp Leu Glu Gln Val Gln Asp Leu Ser Lys Asn
            515                 520                 525

Leu Ser Asn Leu Ser Arg Arg Leu Asn Glu Ser Leu Lys Glu Leu Glu
530                 535                 540

Pro Tyr Thr Gln Asn Ala Lys Leu Asn Gln Ala Glu Leu Lys Asn Leu
545                 550                 555                 560

Glu His Lys Leu Asn Leu Ser Thr Lys Asp Leu Ala Gln Ile Lys Pro
                565                 570                 575

Lys Thr Glu Gln Asp Ile Ala Glu Ser Leu His His Asp Val Lys Ser
                580                 585                 590

Thr Leu Leu Gln Ile Ser Asn Leu Ala Lys Asn Glu Gly Asn Glu Ala
            595                 600                 605

Ile Tyr Asn Gln Ala Asn Arg Leu Leu Ala Gln Ile Glu Ile Asn Gln
610                 615                 620

Leu Met Ser Leu Ala Asn Asp Ser Ile Asn Thr Tyr Leu Pro Phe Ser
625                 630                 635                 640

Trp Asp Asp Leu Asn Asp Ser Lys Ile Met Phe Arg Arg Gly Lys Lys
                645                 650                 655

Asp Lys Phe Phe Ala Gln Ile Lys Leu Glu Phe Ala Lys Leu Gly Asp
                660                 665                 670

Leu Glu Ile Leu Ile Ser Leu Asn Asn Glu Lys Tyr Val Asp Ile Asn
            675                 680                 685

Ile Met Ala Glu Asn Ile Glu Phe Arg Lys Thr Ile Tyr Glu Asn Ala
690                 695                 700

His Glu Leu Lys Arg Asn Ile Asn Lys Ala Gly Leu Leu Ser Ala Asn
705                 710                 715                 720

Phe Phe Val Gly Asp Ile Ile Arg Ser Lys Phe Asp Thr Arg Asn Met
                725                 730                 735

Lys Asn Leu Asp Leu Glu Met Gly Met Asp Lys Lys Val
                740                 745
```

<210> SEQ ID NO 78
<211> LENGTH: 749
<212> TYPE: PRT
<213> ORGANISM: Campylobacter jejuni

<400> SEQUENCE: 78

```
Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
            20                  25                  30

Asp Asn Pro Lys Glu Ala Leu Ala Gln Ala Leu Lys Gln Asn Leu Gly
        35                  40                  45

Leu Ser Lys Asp Ala Ser Ser Glu Glu Ile Leu Ala Lys Phe Val Gln
    50                  55                  60

Asn Glu Thr Gly Thr Lys Leu Lys Glu Leu Val Asn Lys Leu Leu Asp
65              70                  75                  80

Gln Ile Asn Ala Gln Lys Asn Pro Asp Ser Pro Val Leu Lys Gln Gly
```

```
                        85                      90                      95
Lys Asn Leu Asn Leu Ala Pro Asn Phe Ala Asn Glu Leu Lys Thr Leu
                100                     105                     110

Ser Thr Glu Leu Ala Lys Ser Asp Thr Phe Thr Gln Val Leu Asp Arg
            115                     120                     125

Leu Asn Gln Ile Leu Lys Pro Ala Ser Glu Ile Lys Asn Asn Asn Leu
        130                     135                     140

Ala Pro Leu Phe Lys Asn Ser Gly Val Phe Leu Glu Ala Lys Leu Lys
145                     150                     155                 160

Asp Ala Leu Asn Glu Glu Leu Leu Pro Lys Ser Phe His Ser Leu Leu
                165                     170                     175

Ser Thr Ile Lys Gly Leu Ser Ser Glu Lys Leu Ser Val Gln Ile Ala
            180                     185                     190

Gln Leu Ala Asn Thr Asn Leu Ser Pro Lys Asp Thr Leu Lys Glu Leu
        195                     200                     205

Lys Asn Ile Ile Asn Ser Ser Lys Ile Glu Asn Lys Gln Ile Leu Asn
    210                     215                     220

Gln Ser Ser Phe Lys Ala Leu Leu Asn Leu Ser Ser Lys Leu Glu Asn
225                     230                     235                 240

Phe Lys Asn Tyr Ile Ser Lys Asn Pro Ser His Ala Gln Glu Lys Ile
                245                     250                     255

Thr Pro Ile Ala Asn Lys Ile Leu Lys Glu Leu Asn Ser Ile Lys Asn
            260                     265                     270

Asp Phe Phe Lys Ala Leu Asn Lys Pro Glu Asn Leu Met Ile Lys Asp
        275                     280                     285

Pro Asn Ile Leu Lys Gln Thr Ala Thr Ala Phe Glu Lys Leu Glu Asn
    290                     295                     300

Thr Leu Lys Asn Ile Leu Gly Asn Gln Ala Ser Lys Ile Gln Asp Lys
305                     310                     315                 320

Glu Asn Ile Leu Glu Asn Leu Leu Ser Asn Lys Glu Asn Met Lys Glu
                325                     330                     335

Glu Lys Leu Asn His Asn Thr Lys Asn Gln Asp Glu Lys His Ile
            340                     345                     350

Lys Ala Ser Lys Glu Glu Thr Leu Thr Asp Asp Thr Lys Thr Asp Ile
        355                     360                     365

Lys Gln Asp Leu Lys Asn Glu Glu Asn Ser His Ala Lys Glu Thr Asp
    370                     375                     380

Ile Lys Glu Asp Glu Asn Leu Asp Ser Asp Ile Lys Thr His Glu Glu
385                     390                     395                 400

Asp Thr Gln Asp Thr Lys Asn Asp Ile Gln Asn Asn Glu Thr Glu Asn
                405                     410                     415

Lys Pro Asp Asn Asp Ile Lys Asn Phe Ala Pro Asn Gln Glu Lys Ile
            420                     425                     430

Lys Asp Glu Lys Gln Glu Lys Ser Lys Glu Asn Ile Lys Glu Asn Pro
        435                     440                     445

Lys Phe Tyr Glu Thr Lys Thr Glu Asn Lys Thr Ser Ile Asn Thr Asn
    450                     455                     460

Thr Asn Thr Ser Asn Pro Asn Thr Asn Asn Thr Gln Asn Leu Asn Asn
465                     470                     475                 480

Ser Gln Asn Ile Gln Ser Asn Asn Gln Thr Met Gln Asn Ile Phe
                485                     490                     495

Lys Asn Gln Glu Phe Ile Lys Gln Asn Ile Ile Lys Asn Leu Ala Phe
            500                     505                     510
```

Asn Val Glu Asn Leu Asp Leu Glu Gln Val Gln Asp Leu Ser Lys Asn
              515                 520                 525

Leu Ser Asn Leu Ser Arg Arg Leu Asn Glu Ser Leu Lys Glu Leu Glu
            530                 535                 540

Pro Tyr Thr Gln Asn Ala Lys Leu Asn Gln Ala Glu Leu Lys Asn Leu
545                 550                 555                 560

Glu His Lys Leu Asn Leu Ser Thr Lys Asp Leu Ala Gln Ile Lys Pro
                565                 570                 575

Lys Thr Glu Gln Asp Ile Ala Glu Ser Leu His His Asp Val Lys Ser
            580                 585                 590

Thr Leu Leu Gln Ile Ser Asn Leu Ala Lys Asn Glu Gly Asn Glu Ala
        595                 600                 605

Ile Tyr Asn Gln Ala Asn Arg Leu Leu Ala Gln Ile Glu Ile Asn Gln
    610                 615                 620

Leu Met Ser Leu Ala Asn Asp Ser Ile Asn Thr Tyr Leu Pro Phe Ser
625                 630                 635                 640

Trp Asp Asp Leu Asn Asp Ser Lys Ile Met Phe Arg Arg Gly Lys Lys
                645                 650                 655

Asp Lys Phe Phe Ala Gln Ile Lys Leu Glu Phe Ala Lys Leu Gly Asp
            660                 665                 670

Leu Glu Ile Leu Ile Ser Leu Asn Asn Glu Lys Tyr Val Asp Ile Asn
        675                 680                 685

Ile Met Ala Glu Asn Ile Glu Phe Arg Lys Thr Ile Tyr Glu Asn Ala
    690                 695                 700

His Glu Leu Lys Arg Asn Ile Asn Lys Ala Gly Leu Leu Ser Ala Asn
705                 710                 715                 720

Phe Phe Val Gly Asp Ile Ile Arg Ser Lys Phe Asp Thr Arg Asn Met
                725                 730                 735

Lys Asn Leu Asp Leu Glu Met Gly Met Asp Lys Lys Val
            740                 745

<210> SEQ ID NO 79
<211> LENGTH: 749
<212> TYPE: PRT
<213> ORGANISM: Campylobacter jejuni

<400> SEQUENCE: 79

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
            20                  25                  30

Asp Asn Pro Lys Glu Ala Leu Ala Gln Ala Leu Lys Gln Asn Leu Gly
        35                  40                  45

Leu Ser Lys Asp Ala Ser Ser Glu Glu Ile Leu Ala Lys Phe Val Gln
    50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Thr Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu

-continued

```
            130                 135                 140
Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
        195                 200                 205

Lys Asn Ile Ile Asn Ser Ser Lys Ile Glu Asn Lys Gln Ile Leu Asn
    210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
            260                 265                 270

Asp Phe Phe Lys Ala Leu Asn Lys Pro Glu Asn Leu Met Ile Lys Asp
        275                 280                 285

Pro Asn Ile Leu Lys Gln Thr Ala Thr Ala Phe Glu Lys Leu Glu Asn
    290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Met Lys Glu
                325                 330                 335

Glu Lys Leu Asn His Asn Thr Lys Asn Gln Asp Glu Lys His Ile
            340                 345                 350

Lys Ala Ser Lys Glu Glu Thr Leu Thr Asp Asp Thr Lys Thr Asp Ile
        355                 360                 365

Lys Gln Asp Leu Lys Asn Glu Glu Asn Ser His Ala Lys Glu Thr Asp
    370                 375                 380

Ile Lys Glu Asp Glu Asn Leu Asp Ser Asp Ile Lys Thr His Glu Glu
385                 390                 395                 400

Asp Thr Gln Asp Thr Lys Asn Asp Ile Gln Asn Asn Glu Thr Glu Asn
                405                 410                 415

Lys Pro Asp Asn Asp Ile Lys Asn Phe Thr Pro Asn Gln Glu Lys Ile
            420                 425                 430

Lys Asp Glu Lys Gln Glu Lys Ser Lys Glu Asn Ile Lys Glu Asn Pro
        435                 440                 445

Lys Phe Tyr Glu Thr Lys Thr Glu Asn Lys Thr Ser Ile Asn Thr Asn
    450                 455                 460

Thr Asn Thr Ser Asn Pro Asn Thr Asn Thr Gln Asn Leu Asn Asn
465                 470                 475                 480

Ser Gln Asn Ile Gln Ser Asn Asn Gln Thr Met Gln Asn Ile Phe
                485                 490                 495

Lys Asn Gln Glu Phe Ile Lys Gln Asn Ile Ile Lys Asn Leu Ala Phe
            500                 505                 510

Asn Val Glu Asn Leu Asp Leu Glu Gln Val Gln Asp Leu Ser Lys Asn
        515                 520                 525

Leu Ser Asn Leu Ser Arg Arg Leu Asn Glu Ser Leu Lys Glu Leu Glu
    530                 535                 540

Pro Tyr Thr Gln Asn Ala Lys Leu Asn Gln Ala Glu Leu Lys Asn Leu
545                 550                 555                 560
```

```
Glu His Lys Leu Asn Leu Ser Thr Lys Asp Leu Ala Gln Ile Lys Pro
            565                 570                 575

Lys Thr Glu Gln Asp Ile Ala Glu Ser Leu His His Asp Val Lys Ser
        580                 585                 590

Thr Leu Leu Gln Ile Ser Asn Leu Ala Lys Asn Glu Gly Asn Glu Ala
        595                 600                 605

Ile Tyr Asn Gln Ala Asn Arg Leu Leu Ala Gln Ile Glu Ile Asn Gln
        610                 615                 620

Leu Met Ser Leu Ala Asn Asp Ser Ile Asn Thr Tyr Leu Pro Phe Ser
625                 630                 635                 640

Trp Asp Asp Leu Asn Asp Ser Lys Ile Met Phe Arg Arg Gly Lys Lys
                645                 650                 655

Asp Lys Phe Phe Ala Gln Ile Lys Leu Glu Phe Ala Lys Leu Gly Asp
                660                 665                 670

Leu Glu Ile Leu Ile Ser Leu Asn Asn Glu Lys Tyr Ile Asp Ile Asn
            675                 680                 685

Ile Met Ala Glu Asn Ile Glu Phe Arg Lys Thr Ile Tyr Glu Asn Ala
        690                 695                 700

His Glu Leu Lys Arg Asn Ile Asn Lys Ala Gly Leu Leu Ser Ala Asn
705                 710                 715                 720

Phe Phe Val Gly Asp Ile Ile Arg Ser Lys Phe Asp Thr Arg Asn Met
                725                 730                 735

Lys Asn Leu Asp Leu Glu Met Gly Met Asp Lys Lys Val
                740                 745

<210> SEQ ID NO 80
<211> LENGTH: 749
<212> TYPE: PRT
<213> ORGANISM: Campylobacter jejuni

<400> SEQUENCE: 80

Met Ile Asn Thr Gln Leu Ala Ser Gln Ile Ala Asn Thr Gln Lys Asn
1               5                   10                  15

Asp Leu Lys Val Asp Asn Ser Thr Ser Lys Asp Lys Thr Asn Leu Lys
            20                  25                  30

Asp Asn Pro Lys Glu Ala Leu Ala Gln Ala Leu Lys Gln Asn Leu Gly
        35                  40                  45

Leu Ser Lys Asp Ala Ser Ser Glu Glu Ile Leu Ala Lys Phe Ile Gln
    50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Ile Leu Lys Gln Gly
                85                  90                  95

Lys Asn Leu Asn Leu Ala Pro Asn Phe Ala Asn Glu Leu Lys Thr Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
```

```
                180                 185                 190
Gln Leu Ala Asn Thr Asn Leu Ser Pro Lys Asp Thr Leu Lys Glu Leu
            195                 200                 205

Lys Asn Ile Ile Asn Ser Ser Lys Asn Glu Asn Lys Gln Ile Leu Asn
210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
            245                 250                 255

Thr Pro Ile Ala Asn Lys Ile Leu Lys Glu Leu Asn Ser Ile Lys Asn
            260                 265                 270

Asp Phe Phe Lys Ala Leu Asn Lys Pro Glu Asn Leu Met Ile Lys Asp
            275                 280                 285

Pro Asn Ile Leu Lys Gln Thr Ala Thr Ala Phe Glu Lys Leu Glu Asn
            290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Met Lys Glu
                325                 330                 335

Glu Lys Leu Asn His Asn Thr Lys Asn Gln Asp Glu Lys His Ile
            340                 345                 350

Lys Ala Ser Lys Glu Glu Thr Leu Thr Asp Asp Thr Lys Thr Asp Ile
            355                 360                 365

Lys Gln Asp Ser Lys Asn Glu Glu Asn Ser His Ala Lys Glu Thr Asp
            370                 375                 380

Ile Lys Glu Asp Glu Asn Leu Asp Ser Asp Ile Lys Thr His Glu Glu
385                 390                 395                 400

Asp Thr Gln Asp Thr Lys Asn Asp Ile Gln Asn Asn Glu Thr Glu Asn
                405                 410                 415

Lys Pro Asp Asn Asp Ile Lys Asn Ser Thr Pro Asn Gln Glu Lys Ile
            420                 425                 430

Lys Asp Gly Lys Gln Glu Lys Ser Lys Glu Asn Ile Lys Glu Asn Pro
            435                 440                 445

Lys Phe Tyr Glu Thr Lys Thr Glu Asn Lys Thr Ser Ile Asn Thr Asn
            450                 455                 460

Thr Asn Thr Ser Asn Pro Asn Thr Asn Asn Thr Gln Asn Leu Asn Asn
465                 470                 475                 480

Ser Gln Asn Ile Gln Ser Asn Asn Asn Gln Thr Met Gln Asn Ile Phe
                485                 490                 495

Lys Asn Gln Glu Phe Ile Lys Gln Asn Ile Val Lys Asn Leu Ala Phe
            500                 505                 510

Asn Val Glu Asn Leu Asp Leu Glu Gln Val Gln Asp Leu Ser Lys Asn
            515                 520                 525

Leu Ser Asn Leu Ser Arg Arg Leu Asn Glu Ser Leu Lys Glu Leu Glu
            530                 535                 540

Pro Tyr Thr Gln Asn Ala Lys Leu Asn Gln Ala Glu Leu Lys Asn Leu
545                 550                 555                 560

Glu His Lys Leu Asn Leu Ser Thr Lys Asp Leu Ala Gln Ile Lys Pro
                565                 570                 575

Lys Thr Glu Gln Asp Ile Ala Glu Ser Leu His His Asp Val Lys Ser
            580                 585                 590

Thr Leu Leu Gln Ile Ser Asn Leu Ala Lys Asn Glu Gly Asn Glu Ala
            595                 600                 605
```

Ile Tyr Asn Gln Ala Asn Arg Leu Leu Ala Gln Ile Glu Ile Asn Gln
610             615                 620

Leu Met Ser Leu Ala Asn Asp Ser Ile Asn Thr Tyr Leu Pro Phe Ser
625             630                 635                 640

Trp Asp Asp Leu Asn Asp Ser Lys Ile Met Phe Arg Arg Gly Lys Lys
            645                 650                 655

Asp Lys Phe Phe Ala Gln Ile Lys Leu Lys Phe Ala Lys Leu Gly Asp
            660                 665                 670

Leu Glu Ile Leu Ile Ser Leu Asn Asn Glu Lys Tyr Ile Asp Ile Asn
            675                 680                 685

Ile Met Ala Glu Asn Ile Glu Phe Arg Lys Thr Ile Tyr Glu Asn Ala
690             695                 700

His Glu Leu Lys Arg Asn Ile Asn Lys Ala Gly Leu Leu Ser Ala Asn
705             710                 715                 720

Phe Phe Val Gly Asp Ile Ile Arg Ser Lys Phe Asp Thr Arg Asn Met
            725                 730                 735

Lys Asn Leu Asp Leu Glu Met Gly Met Asp Lys Lys Val
            740                 745

<210> SEQ ID NO 81
<211> LENGTH: 698
<212> TYPE: PRT
<213> ORGANISM: Campylobacter jejuni

<400> SEQUENCE: 81

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
                20                  25                  30

Asp Asn Pro Lys Glu Ala Leu Ala Gln Ala Leu Lys Gln Asn Leu Gly
            35                  40                  45

Leu Ser Lys Asp Thr Ser Ser Glu Glu Ile Leu Ala Lys Phe Val Gln
    50                  55                  60

Asn Glu Thr Gly Ala Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Thr Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
        195                 200                 205

Lys Asn Ile Ile Asn Ser Ser Lys Asn Glu Lys Gln Ile Leu Asn
    210                 215                 220

Gln Ser Ser Phe Lys Ala Leu Leu Asn Leu Ser Ser Lys Leu Glu Asn

```
            225                 230                 235                 240
        Phe Lys Asn Tyr Ile Ser Lys Asn Pro Ser His Ala Gln Glu Lys Ile
                        245                 250                 255
        Thr Pro Ile Ala Asn Lys Ile Leu Lys Glu Leu Asn Ser Val Lys Asn
                        260                 265                 270
        Asp Phe Phe Lys Ala Leu Asn Lys Pro Glu Asn Leu Met Ile Lys Asp
                        275                 280                 285
        Pro Asn Ile Leu Lys Gln Thr Ala Thr Ala Phe Glu Lys Leu Glu Asn
                        290                 295                 300
        Thr Leu Lys Asn Ile Leu Gly Asn Gln Ala Ser Lys Ile Gln Asp Lys
        305                 310                 315                 320
        Glu Asn Ile Leu Glu Asn Leu Leu Ser Asn Lys Glu Asn Ile Lys Glu
                        325                 330                 335
        Glu Lys Leu Asn His Asn Thr Lys Asn Gln Asp Glu Glu Lys His Ile
                        340                 345                 350
        Lys Val Ser Lys Glu Glu Thr Leu Ala Asp Asp Ala Lys Thr Asn Ile
                        355                 360                 365
        Lys Gln Asp Val Lys Asn Glu Glu Asn Leu Pro Lys Lys Glu Val Asn
                        370                 375                 380
        Ala Asn Leu Asp Ser Ser Thr Lys Thr His Glu Ser Ile Lys Glu
        385                 390                 395                 400
        Asn Pro Lys Phe Tyr Glu Thr Lys Thr Glu Ser Lys Thr Ser Ile Asn
                        405                 410                 415
        Thr Asn Thr Asn Thr Asn Asn Thr Gln Asn Leu Asn Asn Ser Gln Asn
                        420                 425                 430
        Ile Gln Ser Asn Asn Asn Gln Thr Met Gln Asn Ile Phe Lys Asn Gln
                        435                 440                 445
        Glu Phe Ile Lys Gln Asn Ile Val Lys Asn Leu Ala Phe Asn Val Glu
                        450                 455                 460
        Asn Leu Asp Leu Glu Gln Val Gln Asp Leu Ser Lys Asn Leu Ser Asn
        465                 470                 475                 480
        Leu Ser Arg Arg Leu Asn Glu Ser Leu Lys Glu Leu Glu Pro Tyr Thr
                        485                 490                 495
        Gln Asn Ala Lys Leu Asn Gln Ala Glu Leu Lys Asn Leu Glu His Lys
                        500                 505                 510
        Leu Asn Leu Ser Ile Lys Asp Leu Val Gln Ile Lys Pro Lys Thr Glu
                        515                 520                 525
        Gln Asp Ile Ala Glu Ser Leu His His Asp Val Lys Ser Thr Leu Leu
                        530                 535                 540
        Gln Ile Ser Asn Leu Ala Lys Asn Glu Gly Asn Glu Ala Val Tyr Asn
        545                 550                 555                 560
        Gln Ala Asn Arg Leu Leu Ala Gln Ile Glu Ile Asn Gln Leu Met Ser
                        565                 570                 575
        Leu Ala Asn Asp Ser Ile Asn Thr Tyr Leu Pro Phe Ser Trp Asp Asp
                        580                 585                 590
        Leu Asn Asp Ser Lys Ile Met Phe Arg Arg Gly Lys Lys Asp Lys Phe
                        595                 600                 605
        Phe Ala Gln Ile Lys Leu Glu Phe Ala Lys Leu Gly Asp Leu Glu Ile
                        610                 615                 620
        Leu Ile Ser Leu Asn Asn Glu Lys Tyr Ile Asp Ile Asn Ile Met Ala
        625                 630                 635                 640
        Glu Asn Ile Glu Phe Arg Lys Thr Ile Tyr Glu Asn Ala His Glu Leu
                        645                 650                 655
```

```
Lys Arg Asn Ile Asn Lys Ala Gly Leu Leu Ser Ala Asn Phe Phe Val
            660                 665                 670

Gly Asp Ile Ile Arg Ser Lys Phe Asp Thr Arg Asn Met Lys Asn Leu
            675                 680                 685

Asp Leu Glu Met Gly Met Asp Lys Lys Val
            690                 695

<210> SEQ ID NO 82
<211> LENGTH: 698
<212> TYPE: PRT
<213> ORGANISM: Campylobacter jejuni

<400> SEQUENCE: 82

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
            20                  25                  30

Asp Asn Pro Lys Glu Ala Leu Ala Gln Ala Leu Lys Gln Asn Leu Gly
            35                  40                  45

Leu Ser Lys Asp Ala Ser Ser Glu Ile Leu Ala Lys Phe Val Gln
    50                  55                  60

Asn Glu Thr Gly Thr Lys Leu Lys Glu Leu Val Asn Lys Leu Leu Asp
65              70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Ile Leu
            100                 105                 110

Ser Thr Glu Leu Ala Lys Ser Asp Thr Phe Thr Gln Val Leu Asp Arg
            115                 120                 125

Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Ile Leu Ser Pro Lys Asp Thr Leu Lys Glu Leu
            195                 200                 205

Lys Asn Ile Ile Asn Ser Ser Lys Asn Glu Asn Lys Gln Ile Leu Asn
    210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
            260                 265                 270

Asp Phe Phe Lys Ala Leu Asn Lys Pro Glu Asn Leu Met Ile Lys Asp
            275                 280                 285

Pro Asn Ile Leu Lys Gln Thr Ala Thr Ala Phe Glu Lys Leu Glu Asn
    290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Ile Lys Glu
```

```
                    325                 330                 335
Glu Lys Leu Asn His Asn Thr Lys Asn Gln Asp Glu Glu Lys Tyr Ile
                340                 345                 350
Lys Val Ser Lys Glu Glu Thr Leu Ala Asp Asp Ala Lys Thr Asn Ile
                355                 360                 365
Lys Gln Asp Val Lys Asn Glu Glu Asn Leu Pro Lys Lys Glu Val Asn
            370                 375                 380
Ala Asn Leu Asp Ser Ser Thr Lys Thr His Glu Glu Asn Ile Lys Glu
385                 390                 395                 400
Asn Pro Lys Phe Tyr Glu Thr Lys Thr Glu Ser Lys Thr Ser Ile Asn
                405                 410                 415
Thr Asn Thr Asn Thr Asn Asn Thr Gln Asn Leu Asn Asn Ser Gln Asn
            420                 425                 430
Ile Gln Ser Asn Asn Gln Thr Met Gln Asn Ile Phe Lys Asn Gln
                435                 440                 445
Glu Phe Ile Lys Gln Asn Ile Val Lys Asn Leu Ala Phe Asn Val Glu
                450                 455                 460
Asn Leu Asp Leu Glu Gln Val Gln Asp Leu Ser Lys Asn Leu Ser Asn
465                 470                 475                 480
Leu Ser Arg Arg Leu Asn Glu Ser Leu Lys Glu Leu Glu Pro Tyr Thr
                485                 490                 495
Gln Asn Ala Lys Leu Asn Gln Ala Glu Leu Lys Asn Leu Glu His Lys
            500                 505                 510
Leu Asn Leu Ser Ile Lys Asp Leu Val Gln Ile Lys Pro Lys Thr Glu
            515                 520                 525
Gln Asp Ile Ala Glu Ser Leu His His Asp Val Lys Ser Thr Leu Leu
            530                 535                 540
Gln Ile Ser Asn Leu Ala Lys Asn Glu Gly Asn Glu Ala Val Tyr Asn
545                 550                 555                 560
Gln Ala Asn Arg Leu Leu Ala Gln Ile Glu Ile Asn Gln Leu Met Ser
                565                 570                 575
Leu Ala Asn Asp Ser Ile Asn Thr Tyr Leu Pro Phe Ser Trp Asp Asp
            580                 585                 590
Leu Asn Asp Ser Lys Ile Met Phe Arg Arg Gly Lys Lys Asp Lys Phe
            595                 600                 605
Phe Ala Gln Ile Lys Leu Glu Phe Ala Lys Leu Gly Asp Leu Glu Ile
            610                 615                 620
Leu Ile Ser Leu Asn Asn Glu Lys Tyr Ile Asp Ile Asn Ile Met Ala
625                 630                 635                 640
Glu Asn Ile Glu Phe Arg Lys Thr Ile Tyr Glu Asn Ala His Glu Leu
                645                 650                 655
Lys Arg Asn Ile Asn Lys Ala Gly Leu Leu Ser Ala Asn Phe Phe Val
            660                 665                 670
Gly Asp Ile Ile Arg Ser Lys Phe Asp Thr Arg Asn Met Lys Asn Leu
            675                 680                 685
Asp Leu Glu Met Gly Met Asp Lys Lys Val
            690                 695
```

<210> SEQ ID NO 83
<211> LENGTH: 253
<212> TYPE: PRT
<213> ORGANISM: Campylobacter jejuni

<400> SEQUENCE: 83

```
Met Arg Phe Asp Phe Val Ser Lys Arg Leu Asn Ile Ser Arg Asn
1               5                   10                  15

Lys Ala Leu Glu Leu Ile Glu Asn Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Lys Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
                100                 105                 110

Glu Asn Gln Ala Leu Lys Ile Thr Ala Leu Asp Val Gly Ser Asn Gln
            115                 120                 125

Leu His Pro Ser Leu Arg Val Asn Glu Lys Ile Ile Leu His Glu Asn
    130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250
```

<210> SEQ ID NO 84
<211> LENGTH: 253
<212> TYPE: PRT
<213> ORGANISM: Campylobacter jejuni

<400> SEQUENCE: 84

```
Met Arg Phe Asp Phe Phe Val Ser Lys Arg Leu Asn Ile Ser Arg Asn
1               5                   10                  15

Lys Ala Leu Glu Leu Ile Glu Asn Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Lys Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
                100                 105                 110

Glu Asn Gln Ala Leu Lys Ile Thr Ala Leu Asp Val Gly Ser Asn Gln
            115                 120                 125
```

Leu His Pro Ser Leu Arg Val Asn Glu Lys Ile Ile Leu His Glu Asn
        130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Phe Lys Asn
                245                 250

<210> SEQ ID NO 85
<211> LENGTH: 253
<212> TYPE: PRT
<213> ORGANISM: Campylobacter jejuni

<400> SEQUENCE: 85

Met Arg Phe Asp Phe Phe Val Ser Lys Arg Leu Asn Ile Ser Arg Asn
1               5                   10                  15

Lys Ala Leu Glu Leu Ile Glu Asn Glu Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Lys Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Pro Ser Leu Arg Ala Asn Glu Lys Ile Ile Leu His Glu Asn
        130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Val Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Glu Cys Ala Lys
210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn

<210> SEQ ID NO 86
<211> LENGTH: 253
<212> TYPE: PRT
<213> ORGANISM: Campylobacter jejuni

<400> SEQUENCE: 86

Met Arg Phe Asp Phe Val Ser Lys Arg Leu Asn Ile Ser Arg Asn
1               5                   10                  15

Lys Ala Leu Glu Leu Ile Glu Asn Glu Ile Leu Leu Asn Gly Lys
                20                  25                  30

Ser Phe Lys Ala Ser Phe Asp Val Lys Asn Phe Leu Glu Asn Leu Lys
            35                  40                  45

Lys Thr Gln Asp Leu Asn Pro Glu Asp Ile Leu Leu Ala Asn Glu Leu
50                      55                  60

Lys Leu Asp Leu Leu Ser Glu Ile Tyr Val Ser Arg Ala Ala Leu Lys
65                  70                  75                  80

Leu Lys Lys Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Pro Ser Leu Arg Ala Asn Glu Lys Ile Ile Leu His Glu Asn
130                 135                 140

Thr Asp Leu Arg Ala Phe Lys Ser Lys Glu Lys Phe Glu Leu Val Thr
145                 150                 155                 160

Cys Asp Val Ser Phe Ile Ser Leu Ile Asn Leu Leu Tyr Tyr Val Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Glu Cys Ala Lys
210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
            245                 250

<210> SEQ ID NO 87
<211> LENGTH: 253
<212> TYPE: PRT
<213> ORGANISM: Campylobacter jejuni

<400> SEQUENCE: 87

Met Arg Phe Asp Phe Val Ser Lys Arg Leu Asn Ile Ser Arg Asn
1               5                   10                  15

Lys Ala Leu Glu Leu Ile Glu Asn Glu Ile Leu Leu Asn Gly Lys
                20                  25                  30

Ser Phe Lys Ala Ser Phe Asp Val Lys Asn Phe Leu Glu Asn Leu Lys
            35                  40                  45

Lys Thr Gln Asp Leu Asn Pro Glu Asp Ile Leu Leu Ala Asn Glu Leu
50                      55                  60

Lys Leu Asp Leu Leu Ser Glu Ile Tyr Val Ser Arg Ala Ala Leu Lys

```
            65                  70                  75                  80
Leu Lys Lys Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
                100                 105                 110

Glu Asn Gln Ala Leu Lys Ile Thr Ala Leu Asp Val Gly Ser Asn Gln
                115                 120                 125

Leu His Pro Ser Leu Arg Ala Asn Glu Lys Ile Ile Leu His Glu Asn
            130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Val Asp
                    165                 170                 175

Asn Leu Ala Leu Lys Glu Ile Ile Leu Leu Phe Lys Pro Gln Phe Glu
                180                 185                 190

Val Gly Lys Asn Ile Lys Arg Asp Lys Lys Gly Val Leu Lys Asp Asp
                195                 200                 205

Lys Ala Ile Leu Lys Ala Arg Met Asp Phe Glu Lys Glu Cys Ala Lys
            210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Phe Lys Asn
                    245                 250

<210> SEQ ID NO 88
<211> LENGTH: 253
<212> TYPE: PRT
<213> ORGANISM: Campylobacter jejuni

<400> SEQUENCE: 88

Met Arg Phe Asp Phe Phe Val Ser Lys Arg Leu Asn Ile Ser Arg Asn
1               5                   10                  15

Lys Ala Leu Glu Leu Ile Glu Asn Glu Glu Ile Leu Leu Asn Gly Lys
                20                  25                  30

Ser Phe Lys Ala Ser Phe Asp Val Lys Asn Phe Leu Glu Asn Leu Lys
            35                  40                  45

Lys Thr Gln Asp Leu Asn Pro Glu Asp Ile Leu Leu Ala Asn Glu Leu
        50                  55                  60

Lys Leu Asp Leu Leu Ser Glu Ile Tyr Val Ser Arg Ala Ala Leu Lys
65                  70                  75                  80

Leu Lys Lys Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
                100                 105                 110

Glu Asn Gln Ala Leu Lys Ile Thr Ala Leu Asp Val Gly Ser Asn Gln
                115                 120                 125

Leu His Pro Ser Leu Arg Ala Asn Glu Lys Ile Ile Leu His Glu Asn
            130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Val Asp
                    165                 170                 175

Asn Leu Ala Leu Lys Glu Ile Ile Leu Leu Phe Lys Pro Gln Phe Glu
                180                 185                 190
```

-continued

Val Gly Lys Asn Ile Lys Arg Asp Lys Lys Gly Val Leu Lys Asp Asp
         195                 200                 205

Lys Ala Ile Leu Lys Ala Arg Met Asp Phe Glu Lys Glu Cys Ala Lys
    210                 215                 220

Leu Ser Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250

<210> SEQ ID NO 89
<211> LENGTH: 253
<212> TYPE: PRT
<213> ORGANISM: Campylobacter jejuni

<400> SEQUENCE: 89

Met Arg Phe Asp Phe Phe Val Ser Lys Arg Leu Asn Ile Ser Arg Asn
1               5                   10                  15

Lys Ala Leu Glu Leu Ile Glu Asn Glu Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Ser Ser Leu Arg Val Asn Glu Lys Ile Ile Leu Tyr Glu Asn
    130                 135                 140

Thr Asp Leu Arg Thr Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250

<210> SEQ ID NO 90
<211> LENGTH: 253
<212> TYPE: PRT
<213> ORGANISM: Campylobacter jejuni

<400> SEQUENCE: 90

Met Arg Phe Asp Phe Phe Val Ser Lys Arg Leu Asn Ile Ser Arg Asn
1               5                   10                  15

Lys Ala Leu Glu Leu Ile Glu Asn Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Leu Glu Asp Ile Leu Leu Ala Asn Glu Leu
 50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Ser Ser Leu Arg Val Asn Glu Lys Ile Ile Leu His Glu Asn
    130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250

<210> SEQ ID NO 91
<211> LENGTH: 253
<212> TYPE: PRT
<213> ORGANISM: Campylobacter jejuni

<400> SEQUENCE: 91

Met Arg Phe Asp Phe Phe Val Ser Lys Arg Leu Asn Ile Ser Arg Asn
1               5                   10                  15

Lys Ala Leu Glu Leu Ile Glu Asn Glu Glu Val Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Ala Asp Glu Leu
 50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Pro Ser Leu Arg Ala Asn Glu Lys Ile Ile Leu His Glu Asn
    130                 135                 140

```
Ile Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Glu Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250

<210> SEQ ID NO 92
<211> LENGTH: 253
<212> TYPE: PRT
<213> ORGANISM: Campylobacter jejuni

<400> SEQUENCE: 92

Met Arg Phe Asp Phe Val Ser Lys Arg Leu Asn Ile Ser Arg Asn
1               5                   10                  15

Lys Ala Leu Glu Leu Ile Glu Asn Glu Ile Leu Leu Asn Gly Lys
            20                  25                  30

Ser Phe Lys Ala Ser Phe Asp Val Lys Asn Phe Leu Glu Asn Leu Lys
            35                  40                  45

Lys Thr Gln Asp Leu Asn Leu Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
                100                 105                 110

Glu Asn Gln Ala Leu Lys Ile Thr Ala Leu Asp Val Gly Ser Asn Gln
            115                 120                 125

Leu His Ser Ser Leu Arg Val Asn Glu Lys Ile Ile Leu His Glu Asn
    130                 135                 140

Thr Asp Leu Arg Thr Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250
```

```
<210> SEQ ID NO 93
<211> LENGTH: 253
<212> TYPE: PRT
<213> ORGANISM: Campylobacter jejuni

<400> SEQUENCE: 93

Met Arg Phe Asp Phe Phe Val Ser Lys Arg Leu Asn Ile Ser Arg Asn
1               5                   10                  15

Lys Ala Leu Glu Leu Ile Glu Asn Glu Val Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Ala Asn Glu Leu
    50                  55                  60

Lys Leu Asp Leu Leu Arg Glu Ile Tyr Val Ser Arg Ala Ala Leu Lys
65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Pro Ser Leu Arg Ala Asn Glu Lys Ile Ile Leu His Glu Asn
    130                 135                 140

Thr Asp Leu Arg Ala Phe Lys Ser Glu Glu Lys Phe Glu Phe Ile Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Gly Val Leu Lys Asp Gly
        195                 200                 205

Lys Ala Ile Leu Lys Ala Arg Met Asp Phe Glu Lys Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Ile Lys Asn
                245                 250

<210> SEQ ID NO 94
<211> LENGTH: 253
<212> TYPE: PRT
<213> ORGANISM: Campylobacter jejuni

<400> SEQUENCE: 94

Met Arg Phe Asp Phe Phe Val Ser Lys Arg Leu Asp Ile Ser Arg Asn
1               5                   10                  15

Lys Ala Leu Glu Leu Ile Glu Asn Glu Val Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Ala Asp Glu Leu
    50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
```

```
            85                  90                  95
Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
            115                 120                 125

Leu His Pro Ser Leu Arg Ala Asn Glu Lys Ile Ile Leu His Glu Asn
            130                 135                 140

Ile Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                    165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
            195                 200                 205

Lys Ala Ile Leu Lys Ala Arg Met Asp Phe Glu Lys Glu Cys Ala Lys
210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
            245                 250

<210> SEQ ID NO 95
<211> LENGTH: 253
<212> TYPE: PRT
<213> ORGANISM: Campylobacter jejuni

<400> SEQUENCE: 95

Met Arg Phe Asp Phe Phe Val Ser Lys Arg Leu Asn Ile Ser Arg Asn
1               5                   10                  15

Lys Ala Leu Glu Leu Ile Glu Asn Glu Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Leu Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Thr Leu Asp Val Gly Ser Asn Gln
            115                 120                 125

Leu His Pro Ser Leu Arg Ala Asn Glu Ile Ile Ile Leu His Glu Asn
            130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                    165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
            195                 200                 205
```

```
Lys Ala Ile Leu Lys Ala Arg Met Asp Phe Glu Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250

<210> SEQ ID NO 96
<211> LENGTH: 251
<212> TYPE: PRT
<213> ORGANISM: Campylobacter jejuni

<400> SEQUENCE: 96

Met Ile Phe Phe Val Ser Lys Arg Leu Asn Ile Ser Arg Asn Lys Ala
1               5                   10                  15

Leu Glu Leu Ile Glu Asn Glu Glu Ile Leu Leu Asn Gly Lys Ser Phe
            20                  25                  30

Lys Ala Ser Phe Asp Val Lys Asn Phe Leu Glu Asn Leu Lys Lys Thr
        35                  40                  45

Gln Asp Leu Asn Pro Glu Asp Ile Leu Leu Ala Asn Glu Leu Lys Leu
    50                  55                  60

Asp Leu Leu Ser Glu Ile Tyr Val Ser Arg Ala Ala Leu Lys Leu Lys
65                  70                  75                  80

Lys Phe Leu Glu Glu Asn Asp Ile Glu Ile Lys His Lys Asn Cys Leu
                85                  90                  95

Asp Ile Gly Ser Ser Thr Gly Gly Phe Val Gln Ile Leu Leu Glu Asn
            100                 105                 110

Gln Ala Leu Lys Ile Thr Ala Leu Asp Val Gly Ser Asn Gln Leu His
        115                 120                 125

Pro Ser Leu Arg Ala Asn Glu Lys Ile Ile Leu His Glu Asn Thr Asp
    130                 135                 140

Leu Arg Ala Phe Lys Ser Glu Glu Lys Phe Glu Leu Val Thr Cys Asp
145                 150                 155                 160

Val Ser Phe Ile Ser Leu Ile Asn Leu Leu Tyr Tyr Val Asp Asn Leu
                165                 170                 175

Ala Leu Lys Glu Ile Ile Leu Leu Phe Lys Pro Gln Phe Glu Val Gly
            180                 185                 190

Lys Asn Ile Lys Arg Asp Lys Lys Gly Val Leu Lys Asp Asp Lys Ala
        195                 200                 205

Ile Leu Lys Ala Arg Met Asp Phe Glu Lys Cys Ala Lys Leu Gly
    210                 215                 220

Trp Leu Leu Lys Asn Thr Gln Lys Ser Ser Ile Lys Gly Lys Glu Gly
225                 230                 235                 240

Asn Val Glu Tyr Phe Tyr Tyr Tyr Ile Lys Asn
                245                 250

<210> SEQ ID NO 97
<211> LENGTH: 253
<212> TYPE: PRT
<213> ORGANISM: Campylobacter jejuni

<400> SEQUENCE: 97

Met Arg Phe Asp Phe Phe Val Ser Lys Arg Leu Asn Ile Ser Arg Asn
1               5                   10                  15

Lys Ala Leu Glu Leu Ile Glu Asn Glu Glu Ile Leu Leu Asn Gly Lys
            20                  25                  30
```

Ser Phe Lys Ala Ser Phe Asp Val Lys Asn Phe Leu Glu Asn Leu Lys
    35                  40                  45

Lys Thr Gln Asp Leu Asn Leu Glu Asp Ile Leu Leu Ala Asn Glu Leu
50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
            85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Ser Ser Leu Arg Val Asn Glu Lys Ile Ile Leu Tyr Glu Asn
    130                 135                 140

Thr Asp Leu Arg Thr Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Ile Lys Asn
                245                 250

<210> SEQ ID NO 98
<211> LENGTH: 253
<212> TYPE: PRT
<213> ORGANISM: Campylobacter jejuni

<400> SEQUENCE: 98

Met Arg Phe Asp Phe Phe Val Ser Lys Arg Leu Asn Ile Ser Arg Asn
1               5                   10                  15

Lys Ala Leu Glu Leu Ile Glu Asn Glu Glu Val Leu Leu Asn Gly Lys
            20                  25                  30

Ser Phe Lys Ala Ser Phe Asp Val Lys Asn Phe Leu Glu Asn Leu Lys
        35                  40                  45

Lys Ala Gln Asp Leu Asn Pro Glu Asp Val Leu Leu Thr Asp Glu Leu
    50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
            85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Asn Asn Gln
        115                 120                 125

Leu His Pro Ser Leu Arg Thr Asn Glu Lys Ile Ile Leu His Glu Asn
    130                 135                 140

Thr Asp Leu Arg Ala Phe Lys Ser Glu Glu Lys Phe Glu Leu Ile Thr
145                 150                 155                 160

```
Cys Asp Val Ser Phe Ile Ser Leu Ile Asn Leu Leu Tyr Tyr Ile Asp
            165                 170                 175

Asn Leu Ala Leu Lys Glu Ile Ile Leu Leu Phe Lys Pro Gln Phe Glu
        180                 185                 190

Val Gly Lys Asn Ile Lys Arg Asp Lys Lys Gly Val Leu Lys Asp Asp
            195                 200                 205

Lys Ala Ile Leu Lys Ala Arg Met Asp Phe Glu Lys Glu Cys Ala Lys
        210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
            245                 250
```

<210> SEQ ID NO 99
<211> LENGTH: 251
<212> TYPE: PRT
<213> ORGANISM: Campylobacter jejuni

<400> SEQUENCE: 99

```
Met Ile Phe Phe Val Ser Lys Arg Leu Asn Ile Ser Arg Asn Lys Ala
1               5                   10                  15

Leu Glu Leu Ile Glu Asn Glu Glu Ile Leu Leu Asn Gly Lys Ser Phe
            20                  25                  30

Lys Ala Ser Phe Asp Val Lys Asn Phe Leu Glu Asn Leu Lys Lys Thr
        35                  40                  45

Gln Asp Leu Asn Pro Glu Asp Ile Leu Leu Ala Asn Glu Leu Lys Leu
50                  55                  60

Asp Leu Leu Ser Glu Ile Tyr Val Ser Arg Ala Ala Leu Lys Leu Lys
65                  70                  75                  80

Lys Phe Leu Glu Glu Asn Asp Ile Glu Ile Lys His Lys Asn Cys Leu
                85                  90                  95

Asp Ile Gly Ser Ser Thr Gly Gly Phe Val Gln Ile Leu Leu Glu Asn
            100                 105                 110

Gln Ala Leu Lys Ile Thr Ala Leu Asp Val Gly Ser Asn Gln Leu His
        115                 120                 125

Pro Ser Leu Arg Ala Asn Glu Lys Ile Ile Leu His Glu Asn Thr Asp
130                 135                 140

Leu Arg Ala Phe Lys Ser Glu Glu Lys Phe Glu Leu Val Thr Cys Asp
145                 150                 155                 160

Val Ser Phe Ile Ser Leu Ile Asn Leu Leu Tyr Tyr Val Asp Asn Leu
                165                 170                 175

Ala Leu Lys Glu Ile Ile Leu Leu Phe Lys Pro Gln Phe Glu Val Gly
            180                 185                 190

Lys Asn Ile Lys Arg Asp Lys Lys Gly Val Leu Lys Asp Asp Arg Ala
        195                 200                 205

Ile Leu Lys Ala Arg Met Asp Phe Glu Lys Glu Cys Ala Lys Leu Gly
210                 215                 220

Trp Phe Leu Lys Asn Thr Gln Lys Ser Ser Ile Lys Gly Lys Glu Gly
225                 230                 235                 240

Asn Val Glu Tyr Phe Tyr Tyr Tyr Ile Lys Asn
            245                 250
```

<210> SEQ ID NO 100
<211> LENGTH: 253
<212> TYPE: PRT

<213> ORGANISM: Campylobacter jejuni

<400> SEQUENCE: 100

Met Arg Phe Asp Phe Phe Val Ser Lys Arg Leu Asn Ile Ser Arg Asn
1               5                   10                  15

Lys Ala Leu Glu Leu Ile Glu Ser Glu Val Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Ala Asn Glu Leu
    50                  55                  60

Lys Leu Asn Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys Gln Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Ser Asn Leu Arg Thr Asn Glu Lys Val Ile Leu His Glu Asn
    130                 135                 140

Thr Asp Leu Arg Ala Phe Lys Ser Glu Lys Phe Glu Phe Ile Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250

<210> SEQ ID NO 101
<211> LENGTH: 253
<212> TYPE: PRT
<213> ORGANISM: Campylobacter jejuni

<400> SEQUENCE: 101

Met Arg Phe Asp Phe Phe Val Ser Lys Arg Leu Asn Ile Ser Arg Asn
1               5                   10                  15

Lys Ala Leu Glu Leu Ile Glu Asn Glu Glu Val Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Thr Asp Gly Leu
    50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu

```
            100                 105                 110
Glu Asn Gln Ala Leu Lys Ile Thr Ala Leu Asp Val Gly Asn Asn Gln
            115                 120                 125

Leu His Leu Ser Leu Arg Thr Asn Glu Lys Ile Ile Leu His Glu Asn
        130                 135                 140

Thr Asp Leu Arg Ala Phe Lys Ser Glu Glu Lys Phe Glu Leu Ile Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Glu Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
            245                 250

<210> SEQ ID NO 102
<211> LENGTH: 253
<212> TYPE: PRT
<213> ORGANISM: Campylobacter jejuni

<400> SEQUENCE: 102

Met Arg Phe Asp Phe Phe Ile Ser Lys Arg Leu Asn Ile Ser Arg Asn
1               5                   10                  15

Lys Ala Leu Glu Leu Ile Glu Asn Glu Glu Val Leu Leu Asn Gly Lys
            20                  25                  30

Asn Phe Lys Ala Ser Cys Asp Val Lys Asn Phe Leu Glu Asn Leu Lys
        35                  40                  45

Lys Ala Gln Asp Leu Asn Pro Glu Asp Val Leu Leu Ala Asp Glu Leu
    50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Val Lys His Lys Asn
                85                  90                  95

Cys Leu Asp Ile Gly Ser Ser Thr Gly Gly Phe Val Gln Ile Leu Leu
            100                 105                 110

Glu Asn Lys Ala Leu Lys Ile Thr Ala Leu Asp Val Gly Ser Asn Gln
            115                 120                 125

Leu His Pro Ser Leu Arg Thr Asn Glu Lys Val Ile Leu His Glu Asn
        130                 135                 140

Thr Asp Leu Arg Ala Phe Lys Ser Glu Glu Lys Phe Glu Leu Ile Thr
145                 150                 155                 160

Cys Asp Val Ser Phe Ile Ser Leu Val Asn Leu Leu Tyr Tyr Ile Asn
                165                 170                 175

Asn Leu Ala Leu Lys Glu Met Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
    210                 215                 220
```

Leu Gly Trp Leu Leu Lys Asn Thr Gln Lys Ser Ile Lys Gly Lys
225                 230                 235                 240

Glu Gly Asn Val Glu Tyr Phe Tyr Tyr Tyr Ile Lys Asn
                245                 250

<210> SEQ ID NO 103
<211> LENGTH: 253
<212> TYPE: PRT
<213> ORGANISM: Campylobacter jejuni

<400> SEQUENCE: 103

Met Arg Phe Asp Phe Val Ser Lys Arg Leu Asn Ile Ser Arg Asn
1               5                   10                  15

Lys Ala Leu Glu Leu Ile Glu Asn Glu Val Leu Leu Asn Gly Lys
                20                  25                  30

Ser Phe Lys Ala Ser Phe Asp Val Lys Asn Phe Leu Glu Asn Leu Lys
            35                  40                  45

Lys Thr Gln Asp Leu Asn Pro Glu Asp Ile Leu Leu Thr Asp Gly Leu
        50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Gly Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Asn Asn Gln
        115                 120                 125

Leu His Leu Ser Leu Arg Thr Asn Glu Lys Ile Ile Leu His Glu Asn
130                 135                 140

Thr Asp Leu Arg Thr Phe Lys Ser Glu Glu Lys Phe Glu Leu Ile Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250

<210> SEQ ID NO 104
<211> LENGTH: 253
<212> TYPE: PRT
<213> ORGANISM: Campylobacter jejuni

<400> SEQUENCE: 104

Met Arg Phe Asp Phe Val Ser Lys Arg Leu Asn Ile Ser Arg Asn
1               5                   10                  15

Lys Ala Leu Glu Leu Ile Glu Asn Glu Val Leu Leu Asn Gly Lys
                20                  25                  30

Ser Phe Lys Ala Ser Phe Asp Val Lys Asn Leu Leu Glu Asn Leu Leu
            35                  40                  45

```
Lys Lys Gln Asp Leu Asn Ser Glu Glu Ile Tyr Leu Ser Lys Glu Leu
     50                  55                  60

Asn Leu Glu Leu Leu Ser Glu Ile Tyr Ile Ser Arg Ala Ala Leu Lys
 65                  70                  75                  80

Leu Lys Asn Phe Leu Glu Glu Asn Asn Ile Glu Val Asn Asn Lys Asn
                 85                  90                  95

Cys Leu Asp Ile Gly Ser Ser Thr Gly Gly Phe Val Gln Ile Leu Leu
                100                 105                 110

Glu Asn Lys Ala Leu Lys Ile Thr Ala Leu Asp Val Gly Ser Asn Gln
            115                 120                 125

Leu His Ser Ser Leu Arg Thr Asn Glu Lys Ile Ile Leu Tyr Glu Asn
130                 135                 140

Thr Asp Leu Arg Val Phe Lys Ser Glu Glu Lys Phe Glu Phe Ile Thr
145                 150                 155                 160

Cys Asp Val Ser Phe Ile Ser Leu Val Asn Leu Leu Tyr Tyr Ile Asn
                165                 170                 175

Asn Leu Ala Leu Arg Glu Ile Ile Leu Leu Phe Lys Pro Gln Phe Glu
                180                 185                 190

Val Gly Lys Asn Val Lys Arg Asp Lys Lys Gly Val Leu Lys Asp Asp
            195                 200                 205

Lys Val Ile Leu Lys Ala Lys Met Asp Phe Glu Lys Glu Cys Ala Lys
210                 215                 220

Leu Gly Trp Ile Leu Lys Asn Thr Gln Lys Ser Cys Ile Lys Gly Lys
225                 230                 235                 240

Glu Gly Asn Val Glu Tyr Phe Tyr Tyr Tyr Ile Lys Asn
                245                 250

<210> SEQ ID NO 105
<211> LENGTH: 188
<212> TYPE: PRT
<213> ORGANISM: Campylobacter jejuni

<400> SEQUENCE: 105

Met Asp Leu Leu Ser Glu Ile Tyr Val Ser Arg Ala Ala Leu Lys Leu
 1               5                  10                  15

Lys Lys Phe Leu Glu Glu Asn Asp Ile Glu Ile Lys His Lys Asn Cys
                20                  25                  30

Leu Asp Ile Gly Ser Ser Thr Gly Gly Phe Val Gln Ile Leu Leu Glu
            35                  40                  45

Asn Gln Ala Leu Lys Ile Thr Ala Leu Asp Val Gly Ser Asn Gln Leu
 50                  55                  60

His Pro Ser Leu Arg Val Asn Glu Lys Ile Ile Leu His Glu Asn Thr
 65                  70                  75                  80

Asp Leu Arg Ala Phe Lys Ser Glu Glu Lys Phe Glu Leu Val Thr Cys
                 85                  90                  95

Asp Val Ser Phe Ile Ser Leu Ile Asn Leu Leu Tyr Tyr Ile Asp Asn
                100                 105                 110

Leu Ala Leu Lys Glu Ile Ile Leu Leu Phe Lys Pro Gln Phe Glu Val
            115                 120                 125

Gly Lys Asn Ile Lys Arg Asp Lys Lys Gly Val Leu Lys Asp Asp Lys
130                 135                 140

Ala Ile Leu Lys Ala Arg Met Asp Phe Glu Lys Ala Cys Ala Lys Leu
145                 150                 155                 160

Gly Trp Leu Leu Lys Asn Thr Gln Lys Ser Ser Ile Lys Gly Lys Glu
                165                 170                 175
```

Gly Asn Val Glu Tyr Phe Tyr Tyr Ile Lys Asn
            180                 185

<210> SEQ ID NO 106
<211> LENGTH: 52
<212> TYPE: PRT
<213> ORGANISM: Campylobacter jejuni

<400> SEQUENCE: 106

Met Arg Phe Asp Phe Phe Val Ser Lys Arg Leu Asn Ile Ser Arg Asn
1               5                   10                  15

Lys Ala Leu Glu Leu Ile Glu Asn Glu Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Arg Lys Ile
    50

<210> SEQ ID NO 107
<211> LENGTH: 183
<212> TYPE: DNA
<213> ORGANISM: Campylobacter jejuni

<400> SEQUENCE: 107
atggtttcag atgtttctat gggtaatgtt aatttaatga ctgctgttaa tacttcagtt    60
ttgaaaaaat ctatggacac aaacgaggca ttgatgaatg aactcatcga aggtatggaa   120
ggtgtctctc aagcctccgc tccacaagct tctagctcta gtggtttgga tatttacgct   180
taa                                                                 183

<210> SEQ ID NO 108
<211> LENGTH: 60
<212> TYPE: PRT
<213> ORGANISM: Campylobacter jejuni

<400> SEQUENCE: 108

Met Val Ser Asp Val Ser Met Gly Asn Val Asn Leu Met Thr Ala Val
1               5                   10                  15

Asn Thr Ser Val Leu Lys Lys Ser Met Asp Thr Asn Glu Ala Leu Met
            20                  25                  30

Asn Glu Leu Ile Glu Gly Met Glu Gly Val Ser Gln Ala Ser Ala Pro
        35                  40                  45

Gln Ala Ser Ser Ser Ser Gly Leu Asp Ile Tyr Ala
    50                  55                  60

<210> SEQ ID NO 109
<211> LENGTH: 384
<212> TYPE: DNA
<213> ORGANISM: Campylobacter jejuni

<400> SEQUENCE: 109
atgcaggtaa attatagaac gattagctcg tatgaatacg atgctattag tggtcagtat    60
aaacaggtgg ataaacagat tgaagattat tcttcatctg agattctga ttttatggat    120 atgttaaata aggcggatga aagtcaagc ggagatgctt taaattctag cagtagtttt    180
caaagcaatg cgcaaaactc aaattcaaat ttaagtaatt atgctcaaat gtcaaatgtt    240
tacgcttatc gttttagaca aaatgaaggc gagctgtcta tgagagctca agtgctagc    300 gttcataatg atcttacaca acaaggtgca atgaacaaa gtaagaataa tactttgtta    360
aatgatttat tgaacgcaat ttaa                                              384

<210> SEQ ID NO 110
<211> LENGTH: 127
<212> TYPE: PRT
<213> ORGANISM: Campylobacter jejuni

<400> SEQUENCE: 110

Met Gln Val Asn Tyr Arg Thr Ile Ser Ser Tyr Glu Tyr Asp Ala Ile
1               5                   10                  15

Ser Gly Gln Tyr Lys Gln Val Asp Lys Gln Ile Glu Asp Tyr Ser Ser
            20                  25                  30

Ser Gly Asp Ser Asp Phe Met Asp Met Leu Asn Lys Ala Asp Glu Lys
        35                  40                  45

Ser Ser Gly Asp Ala Leu Asn Ser Ser Ser Phe Gln Ser Asn Ala
    50                  55                  60

Gln Asn Ser Asn Ser Asn Leu Ser Asn Tyr Ala Gln Met Ser Asn Val
65                  70                  75                  80

Tyr Ala Tyr Arg Phe Arg Gln Asn Glu Gly Glu Leu Ser Met Arg Ala
                85                  90                  95

Gln Ser Ala Ser Val His Asn Asp Leu Thr Gln Gln Gly Ala Asn Glu
            100                 105                 110

Gln Ser Lys Asn Asn Thr Leu Leu Asn Asp Leu Leu Asn Ala Ile
        115                 120                 125

<210> SEQ ID NO 111
<211> LENGTH: 168
<212> TYPE: DNA
<213> ORGANISM: Campylobacter jejuni

<400> SEQUENCE: 111
atgaaaaaag ttgtactaat ctcagcatta ctaggtgctt tcgcagctaa tgtttttgca    60
gctaatactc aagcgatgt aaatcaaaca catacaaaag ctaaagctga taaaaaacat    120
gaagctaaaa ctcacaaaaa aacaaaagag caaacaccag ctcaataa                168

<210> SEQ ID NO 112
<211> LENGTH: 55
<212> TYPE: PRT
<213> ORGANISM: Campylobacter jejuni

<400> SEQUENCE: 112

Met Lys Lys Val Val Leu Ile Ser Ala Leu Leu Gly Ala Phe Ala Ala
1               5                   10                  15

Asn Val Phe Ala Ala Asn Thr Pro Ser Asp Val Asn Gln Thr His Thr
            20                  25                  30

Lys Ala Lys Ala Asp Lys Lys His Glu Ala Lys Thr His Lys Lys Thr
        35                  40                  45

Lys Glu Gln Thr Pro Ala Gln
    50                  55

<210> SEQ ID NO 113
<211> LENGTH: 336
<212> TYPE: DNA
<213> ORGANISM: Campylobacter jejuni

<400> SEQUENCE: 113
atgatggcta aatttagaat tcaatacagc gcaggttttg ggcactatac gcaaaatcac    60

```
aagggttttg gacctacgat ttatatagaa gaggtcgtag agtttgataa tggcaaggat    120
tattttgact atatagattt ttataaaact tattcaaaga gcgatgatac ttattttcat    180
atcagttttt tagaagatag acctctaagc gataaagaaa tcaccattcg caatgaatac    240
cgcaaaatgc gtgatgaaaa ctgtaaaaaa gccaaggagg aatttatagc caacaatgag    300
cttgatgtgg agcatttgcc tactcaccat gattaa                              336
```

<210> SEQ ID NO 114
<211> LENGTH: 111
<212> TYPE: PRT
<213> ORGANISM: Campylobacter jejuni

<400> SEQUENCE: 114

```
Met Met Ala Lys Phe Arg Ile Gln Tyr Ser Ala Gly Phe Gly His Tyr
1               5                   10                  15

Thr Gln Asn His Lys Gly Phe Gly Pro Thr Ile Tyr Ile Glu Glu Val
            20                  25                  30

Val Glu Phe Asp Asn Gly Lys Asp Tyr Phe Asp Tyr Ile Asp Phe Tyr
        35                  40                  45

Lys Thr Tyr Ser Lys Ser Asp Asp Thr Tyr Phe His Ile Ser Phe Leu
    50                  55                  60

Glu Asp Arg Pro Leu Ser Asp Lys Glu Ile Thr Ile Arg Asn Glu Tyr
65                  70                  75                  80

Arg Lys Met Arg Asp Glu Asn Cys Lys Lys Ala Lys Glu Glu Phe Ile
                85                  90                  95

Ala Asn Asn Glu Leu Asp Val Glu His Leu Pro Thr His His Asp
            100                 105                 110
```

<210> SEQ ID NO 115
<211> LENGTH: 498
<212> TYPE: DNA
<213> ORGANISM: Campylobacter jejuni

<400> SEQUENCE: 115

```
atgaaaaaaa ttcttttttac ttcaatcgca gctcttgcag ttgttattag tggttgtagc     60
acaaaaagca ctagcgtaag cggtgatagt agtgttgatt caaatcgtgg ttcaggtgga    120
agtgatggtt gggatattga ttcaaaaatt tctcaactta atgatacttt aaataaagta    180
tattttgatt ttgataaatt caacattcgt cctgatatgc aaaatgttgt aagcacaaat    240
gctaatattt ttaacactga agtaagcggt gtaagtatta ctgttgaagg aaactgcgat    300
gagtggggaa ccgatgaata taaccaagct ctaggtttaa aaagagcaaa agctgtaaaa    360
gaagctttaa tcgctaaagg tgtaaatgct gatagaattg ctgttaaaag ctatggagaa    420
acaaatcctg tgtgcactga aaaaactaaa gcttgcgatg cgcaaaatag acgtgctgaa    480
tttaaattat caagataa                                                  498
```

<210> SEQ ID NO 116
<211> LENGTH: 165
<212> TYPE: PRT
<213> ORGANISM: Campylobacter jejuni

<400> SEQUENCE: 116

```
Met Lys Lys Ile Leu Phe Thr Ser Ile Ala Ala Leu Ala Val Val Ile
1               5                   10                  15

Ser Gly Cys Ser Thr Lys Ser Thr Ser Val Ser Gly Asp Ser Ser Val
            20                  25                  30
```

Asp Ser Asn Arg Gly Ser Gly Ser Asp Gly Trp Asp Ile Asp Ser
            35                  40                  45

Lys Ile Ser Gln Leu Asn Asp Thr Leu Asn Lys Val Tyr Phe Asp Phe
 50                  55                  60

Asp Lys Phe Asn Ile Arg Pro Asp Met Gln Asn Val Val Ser Thr Asn
 65                  70                  75                  80

Ala Asn Ile Phe Asn Thr Glu Val Ser Gly Val Ser Ile Thr Val Glu
                85                  90                  95

Gly Asn Cys Asp Glu Trp Gly Thr Asp Glu Tyr Asn Gln Ala Leu Gly
            100                 105                 110

Leu Lys Arg Ala Lys Ala Val Lys Glu Ala Leu Ile Ala Lys Gly Val
            115                 120                 125

Asn Ala Asp Arg Ile Ala Val Lys Ser Tyr Gly Glu Thr Asn Pro Val
            130                 135                 140

Cys Thr Glu Lys Thr Lys Ala Cys Asp Ala Gln Asn Arg Arg Ala Glu
145                 150                 155                 160

Phe Lys Leu Ser Arg
            165

<210> SEQ ID NO 117
<211> LENGTH: 840
<212> TYPE: DNA
<213> ORGANISM: Campylobacter jejuni

<400> SEQUENCE: 117
atgaaaaaaa tacttctaag tgttttaacg gcctttgttg cagtagtatt ggctgcttgt      60
ggaggaaatt ctgactctaa aactttaaat tctcttgata agatcaagca aaatggagtt     120
gttaggattg gggtatttgg cgataaacca ccttttggtt atgtggatga aaaaggaaac     180
aatcaaggct atgatatagc tttagctaaa cgcatagcaa agaactttt tggcgatgaa      240
ataaggtgc aatttgttct tgttgaagct gcaaataggg ttgagttttt aaaatcaaat      300
aaagtagata ttattttggc taattttact caaactccgc aaagggcaga gcaggttgat     360
ttttgctcgc cttatatgaa ggtagcttta ggcgtagctg taccaaagga tagtaatata     420
actagcgtag aagatttaaa agataaaacc ttgcttttaa acaaaggcac aacagcagat     480
gcttatttta cgcaaaatta tcctaatatt aaaactttaa aatatgatca aaataccgaa     540
acctttgccg cttttgatgga taaaagaggc gatgcttttaa gtcatgataa taccttactt    600
tttgcttggg tgaaagatca tcctgatttt aaaatgggta ttaaagagtt aggtaacaaa     660
gatgttatcg caccagcggt taaaaaaggc gataaagaac ttaagaatt tatcgataat      720
ttgatcatca aactaggcca agagcagttt tttcacaagg cttatgatga aactttaaaa     780
gctcattttg gagatgatgt taaggccgat gatgtagtga ttgaaggtgg aaaaattaa     840

<210> SEQ ID NO 118
<211> LENGTH: 279
<212> TYPE: PRT
<213> ORGANISM: Campylobacter jejuni

<400> SEQUENCE: 118

Met Lys Lys Ile Leu Leu Ser Val Leu Thr Ala Phe Val Ala Val Val
 1               5                  10                  15

Leu Ala Ala Cys Gly Gly Asn Ser Asp Ser Lys Thr Leu Asn Ser Leu
            20                  25                  30

Asp Lys Ile Lys Gln Asn Gly Val Val Arg Ile Gly Val Phe Gly Asp
            35                  40                  45

```
Lys Pro Pro Phe Gly Tyr Val Asp Glu Lys Gly Asn Asn Gln Gly Tyr
     50                  55                  60

Asp Ile Ala Leu Ala Lys Arg Ile Ala Lys Glu Leu Phe Gly Asp Glu
 65                  70                  75                  80

Asn Lys Val Gln Phe Val Leu Val Glu Ala Ala Asn Arg Val Glu Phe
                 85                  90                  95

Leu Lys Ser Asn Lys Val Asp Ile Ile Leu Ala Asn Phe Thr Gln Thr
            100                 105                 110

Pro Gln Arg Ala Glu Gln Val Asp Phe Cys Ser Pro Tyr Met Lys Val
        115                 120                 125

Ala Leu Gly Val Ala Val Pro Lys Asp Ser Asn Ile Thr Ser Val Glu
    130                 135                 140

Asp Leu Lys Asp Lys Thr Leu Leu Leu Asn Lys Gly Thr Thr Ala Asp
145                 150                 155                 160

Ala Tyr Phe Thr Gln Asn Tyr Pro Asn Ile Lys Thr Leu Lys Tyr Asp
                165                 170                 175

Gln Asn Thr Glu Thr Phe Ala Ala Leu Met Asp Lys Arg Gly Asp Ala
            180                 185                 190

Leu Ser His Asp Asn Thr Leu Leu Phe Ala Trp Val Lys Asp His Pro
        195                 200                 205

Asp Phe Lys Met Gly Ile Lys Glu Leu Gly Asn Lys Asp Val Ile Ala
    210                 215                 220

Pro Ala Val Lys Lys Gly Asp Lys Glu Leu Lys Glu Phe Ile Asp Asn
225                 230                 235                 240

Leu Ile Ile Lys Leu Gly Gln Glu Gln Phe Phe His Lys Ala Tyr Asp
                245                 250                 255

Glu Thr Leu Lys Ala His Phe Gly Asp Asp Val Lys Ala Asp Asp Val
            260                 265                 270

Val Ile Glu Gly Gly Lys Ile
        275

<210> SEQ ID NO 119
<211> LENGTH: 780
<212> TYPE: DNA
<213> ORGANISM: Campylobacter jejuni

<400> SEQUENCE: 119
atggttttta gaaatctttt gttaaagttg cagtttttg ctctaggtgc ttgtgttgca      60
tttagcaatg ctaatgcagc agaaggtaaa cttgagtcta ttaaatctaa aggacaatta    120
atagttggtg ttaaaaatga tgttccgcat tatgctttac ttgatcaagc aacaggtgaa    180
attaaaggtt tcgaagtaga tgttgccaaa ttgctagcta aaagtatatt gggtgatgat    240
aaaaaaataa aactagttgc agttaatgct aaaacaagag gccctttgct tgataatggt    300
agtgtagatg cggtgatagc aactttact attactccag agagaaaaag aatttataat    360
ttctcagagc cttattatca agatgctata gggcttttgg ttttaaaaga aaaaaatat    420 aaatctttag ctgatatgaa aggtgcaaat attggagtgg ctcaagctgc aactacaaaa    480
aaagctatag gtgaagctgc taaaaaaatt ggcattgatg ttaaatttag tgaatttcct    540
gattatccaa gtataaaagc tgctttagat gctaaaagag ttgatgcgtt ttctgtagac    600
aaatcaatat tgttaggtta tgtggatgat aaaagtgaaa ttttgccaga tagttttgaa    660
ccacaaagtt atggtattgt aaccaaaaaa gatgatccag cttttgcaaa atatgttgat    720
gattttgtaa aagaacataa aaatgaaatt gatgctttag cgaaaaaatg gggtttataa    780
```

<210> SEQ ID NO 120
<211> LENGTH: 259
<212> TYPE: PRT
<213> ORGANISM: Campylobacter jejuni

<400> SEQUENCE: 120

Met Val Phe Arg Lys Ser Leu Leu Lys Leu Ala Val Phe Ala Leu Gly
1               5                   10                  15

Ala Cys Val Ala Phe Ser Asn Ala Asn Ala Glu Gly Lys Leu Glu
            20                  25                  30

Ser Ile Lys Ser Lys Gly Gln Leu Ile Val Gly Val Lys Asn Asp Val
        35                  40                  45

Pro His Tyr Ala Leu Leu Asp Gln Ala Thr Gly Glu Ile Lys Gly Phe
    50                  55                  60

Glu Val Asp Val Ala Lys Leu Leu Ala Lys Ser Ile Leu Gly Asp Asp
65                  70                  75                  80

Lys Lys Ile Lys Leu Val Ala Val Asn Ala Lys Thr Arg Gly Pro Leu
                85                  90                  95

Leu Asp Asn Gly Ser Val Asp Ala Val Ile Ala Thr Phe Thr Ile Thr
            100                 105                 110

Pro Glu Arg Lys Arg Ile Tyr Asn Phe Ser Glu Pro Tyr Tyr Gln Asp
        115                 120                 125

Ala Ile Gly Leu Leu Val Leu Lys Glu Lys Lys Tyr Lys Ser Leu Ala
    130                 135                 140

Asp Met Lys Gly Ala Asn Ile Gly Val Ala Gln Ala Ala Thr Thr Lys
145                 150                 155                 160

Lys Ala Ile Gly Glu Ala Ala Lys Lys Ile Gly Ile Asp Val Lys Phe
                165                 170                 175

Ser Glu Phe Pro Asp Tyr Pro Ser Ile Lys Ala Ala Leu Asp Ala Lys
            180                 185                 190

Arg Val Asp Ala Phe Ser Val Asp Lys Ser Ile Leu Leu Gly Tyr Val
        195                 200                 205

Asp Asp Lys Ser Glu Ile Leu Pro Asp Ser Phe Glu Pro Gln Ser Tyr
    210                 215                 220

Gly Ile Val Thr Lys Lys Asp Asp Pro Ala Phe Ala Lys Tyr Val Asp
225                 230                 235                 240

Asp Phe Val Lys Glu His Lys Asn Glu Ile Asp Ala Leu Ala Lys Lys
                245                 250                 255

Trp Gly Leu

<210> SEQ ID NO 121
<211> LENGTH: 1275
<212> TYPE: DNA
<213> ORGANISM: Campylobacter jejuni

<400> SEQUENCE: 121
atgaaactag ttaaacttag tttagttgca gctcttgctg caggtgcttt ttcagcagct      60
aacgctactc cacttgaaga agcgatcaaa gatgttgatg tatcaggtgt attaagatac     120
agatacgata caggtaattt tgataaaaat ttcgttaaca actcaaattt aaacaacagc     180
aaacaagatc acaaatatag agcacaagtt aacttcagtg ctgctatagc tgataacttc     240
aaagcttttg ttcaatttga ctataatgct gctgatggtg ttatggtgc taatggaata     300 aaaaatgatc aaaaaggact ttttgttcgt caattatact taacttatac aaatgaagat     360

```
gttgctacaa gtgtaatcgc tggtaaacaa caattaaacc ttatctggac ggataacgct      420
attgatggtt tagttggcac aggtgttaaa gtagtaaata acagcatcga tggtttaact      480
ctagctgctt ttgctgtaga tagcttcatg gctgcagagc aaggtgcaga tttattagaa      540
catagtaata tttcaacaac atcaaatcaa gctccttta aagtagattc agtaggaaat       600
ctttacggtg ctgctgctgt aggttcttat gatcttgctg gtggacaatt caacccacaa      660
ttatggttag cttattggga tcaagtagca ttcttctatg ctgtagatgc agcttatagt      720
acaactatct ttgatggaat caactggaca cttgaaggtg cttacttagg aaatagcctt      780
gatagcgaac ttgatgataa aacacacgct aatggcaatt tatttgcttt aaaaggtagc      840
attgaagtaa atggttggga tgctagcctt ggtggtttat actacggtga taagaaaaaa      900
gcttctacag ttgtaatcga agatcaaggt aatcttggtt cttacttgc aggtgaggaa       960 atttttctata ctactggttc aagactaaat ggtgatactg gtagaaatat cttcggttat     1020
gtaactggtg gatatacttt caacgaaaca gttcgcgttg gtgctgactt cgtatatggt     1080
ggaacaaaaa cagaagctgc taatcattta ggtggtggta aaaaacttga agctgttgca     1140
agagtagatt acaaatactc tccaaaactt aacttctcag cattctattc ttatgtgaac     1200
ctagatcaag gtgtaaacac taatgaaagt gctgatcata gcactgtaag acttcaagct     1260
ctttacaaat tctaa                                                      1275
```

<210> SEQ ID NO 122
<211> LENGTH: 424
<212> TYPE: PRT
<213> ORGANISM: Campylobacter jejuni

<400> SEQUENCE: 122

```
Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Lys Gln Asp His
        50                  55                  60

Lys Tyr Arg Ala Gln Val Asn Phe Ser Ala Ala Ile Ala Asp Asn Phe
65                  70                  75                  80

Lys Ala Phe Ile Gln Phe Asp Tyr Asn Ala Val Asp Gly Gly Thr Gly
                85                  90                  95

Val Asp Asn Val Thr Asn Ala Glu Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Leu Ile Trp Thr Asp Asn Ala Ile Asp Gly Leu
    130                 135                 140

Val Gly Thr Gly Ile Lys Val Val Asn Asn Ser Ile Asp Gly Leu Thr
145                 150                 155                 160

Leu Ala Ala Phe Ala Val Asp Ser Phe Met Ala Glu Glu Gln Gly Ala
                165                 170                 175

Asp Leu Leu Gly Gln Ser Thr Ile Ser Thr Thr Gln Lys Ala Ala Pro
            180                 185                 190

Phe Lys Val Asp Ser Val Gly Asn Leu Tyr Gly Ala Ala Ala Val Gly
        195                 200                 205
```

-continued

```
Ser Tyr Asp Leu Ala Gly Gly Gln Phe Asn Pro Gln Leu Trp Leu Ala
    210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Thr His Ala Asn Gly
            260                 265                 270

Asn Leu Phe Ala Leu Lys Gly Ser Ile Glu Val Asn Gly Trp Asp Ala
        275                 280                 285

Ser Leu Gly Gly Leu Tyr Tyr Gly Asp Lys Lys Ala Ser Thr Val
    290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Tyr Thr Phe Asn Glu Thr Val Arg
            340                 345                 350

Val Gly Ala Asp Phe Val Tyr Gly Gly Thr Lys Thr Glu Asp Thr Ala
        355                 360                 365

His Val Gly Gly Gly Lys Lys Leu Glu Ala Val Ala Arg Val Asp Tyr
    370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
            420
```

<210> SEQ ID NO 123
<211> LENGTH: 1719
<212> TYPE: DNA
<213> ORGANISM: Campylobacter jejuni

<400> SEQUENCE: 123

```
atgggatttc gtattaacac caatgttgca gctttaaatg caaaagcaaa cgctgattta      60
aatagtaaaa gttagatgc ttctttaagc agacttagtt caggtcttag aatcaactcc     120
gcagcagatg atgcttcagg gatggcgata gcagatagtt taagatctca agctaatact     180
ttaggtcaag ctatatctaa tggtaatgat gctttaggta tcttacaaac tgctgataag     240
gctatggatg agcaacttaa aatcttagat acaatcaaaa ctaaggcaac tcaagcggct     300
caagatggac aaagtttaaa acaagaacc atgcttcaag cagatatcaa ccgtttaatg     360
gaagaacttg acaatattgc aaatactact tcatttaacg gtaaacaact tttaagtggg     420
aatttttatca atcaagaatt tcaaatcggt gcaagttcaa atcaaactgt aaaagctact     480
ataggagcaa ctcaatcttc taagataggt ttaacacgct tgaaacaggag aggaagaatt     540
tcaactagtg gcgaagtaca atttactctt aaaaattaca atggtataga tgattttcag     600
tttcaaaaag ttgtgatttc aacttcagtt ggaacaggac ttggagcttt agcagatgag     660
atcaataaaa atgctgataa acaggtgtt agagctactt ttacagtaga actagaggt     720
atagctgcag ttagagcagg agctacttca gatactttg ctatcaatgg ggtaaaaatc     780
ggtaaagtag attacaaaga tggtgatgct aatggagcct tagttgctgc aatcaattcg     840
gttaaagata ccactggagt tgaagcttcg atcgatgcta atggacaact tttacttact     900
```

```
tcaagagaag gtagagggat taaaatcgat ggtaatatag gtggaggtgc ctttatcaat      960
gctgatatga aagaaaacta tggccgcttg tctttagtta aaaatgatgg taaagatatt     1020
ttaatcagcg gtagcaatct ttcttctgca ggttttggtg caactcaatt tatctctcaa     1080
gcttctgttt ctttaagaga gtcaaaagga caaattgatg ctaatatcgc tgatgctatg     1140
ggatttggtt ctgcaaacaa aggagttgtg ttaggtggtt attcttctgt tagtgcctat     1200
atgagtagcg caggaagtgg attttcttca ggttcaggtt attctgtagg tagcggtaaa     1260
aattattcca caggttttgc aaacgctata gctatttcag ctgcttcgca actttctacg     1320
gtatataatg tttctgcagg ctcaggtttt caagtggtt caacactttc tcagtttgca      1380
actatgaaaa caactgcttt tggagtaaaa gatgaaacag caggtgttac cacacttaaa     1440
ggcgctatgg ctgtgatgga tatagctgaa acagctataa caaatcttga tcaaatcaga     1500
gccgacattg gttcggtaca aaatcaagtt acatcaacta taaacaacat caccgtaact     1560
caagtaaacg ttaaagcagc agaatcgcaa atccgtgatg tagactttgc agccgagagt     1620
gcaaactact ctaaagcaaa tatcttagct caaagcggct cttatgccat ggcacaggct     1680
aattctgttc aacaaaatgt tttaagatta ctacagtag                            1719

<210> SEQ ID NO 124
<211> LENGTH: 572
<212> TYPE: PRT
<213> ORGANISM: Campylobacter jejuni

<400> SEQUENCE: 124

Met Gly Phe Arg Ile Asn Thr Asn Val Ala Ala Leu Asn Ala Lys Ala
1               5                   10                  15

Asn Ala Asp Leu Asn Ser Lys Ser Leu Asp Ala Ser Leu Ser Arg Leu
            20                  25                  30

Ser Ser Gly Leu Arg Ile Asn Ser Ala Ala Asp Asp Ala Ser Gly Met
        35                  40                  45

Ala Ile Ala Asp Ser Leu Arg Ser Gln Ala Asn Thr Leu Gly Gln Ala
    50                  55                  60

Ile Ser Asn Gly Asn Asp Ala Leu Gly Ile Leu Gln Thr Ala Asp Lys
65                  70                  75                  80

Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
            100                 105                 110

Gln Ala Asp Ile Asn Arg Leu Met Glu Glu Leu Asp Asn Ile Ala Asn
        115                 120                 125

Thr Thr Ser Phe Asn Gly Lys Gln Leu Leu Ser Gly Asn Phe Ile Asn
    130                 135                 140

Gln Glu Phe Gln Ile Gly Ala Ser Ser Asn Gln Thr Val Lys Ala Thr
145                 150                 155                 160

Ile Gly Ala Thr Gln Ser Ser Lys Ile Gly Leu Thr Arg Phe Glu Thr
                165                 170                 175

Gly Gly Arg Ile Ser Thr Ser Gly Glu Val Gln Phe Thr Leu Lys Asn
            180                 185                 190

Tyr Asn Gly Ile Asp Asp Phe Gln Phe Gln Lys Val Val Ile Ser Thr
        195                 200                 205

Ser Val Gly Thr Gly Leu Gly Ala Leu Ala Asp Glu Ile Asn Lys Asn
    210                 215                 220
```

| | | | | | | | | | | | | | | |
|---|---|---|---|---|---|---|---|---|---|---|---|---|---|---|
Ala | Asp | Lys | Thr | Gly | Val | Arg | Ala | Thr | Phe | Thr | Val | Glu | Thr | Arg | Gly
225 | | | | 230 | | | | 235 | | | | | | 240

Ile Ala Ala Val Arg Ala Gly Thr Ser Asp Thr Phe Ala Ile Asn
                     245                   250                  255

Gly Val Lys Ile Gly Lys Val Asp Tyr Lys Asp Gly Asp Ala Asn Gly
           260                   265                  270

Ala Leu Val Ala Ala Ile Asn Ser Val Lys Asp Thr Thr Gly Val Glu
       275                  280                  285

Ala Ser Ile Asp Ala Asn Gly Gln Leu Leu Thr Ser Arg Glu Gly
     290                  295               300

Arg Gly Ile Lys Ile Asp Gly Asn Ile Gly Gly Ala Phe Ile Asn
305              310                  315              320

Ala Asp Met Lys Glu Asn Tyr Gly Arg Leu Ser Leu Val Lys Asn Asp
           325                   330                  335

Gly Lys Asp Ile Leu Ile Ser Gly Ser Asn Leu Ser Ser Ala Gly Phe
              340                  345                  350

Gly Ala Thr Gln Phe Ile Ser Gln Ala Ser Val Ser Leu Arg Glu Ser
           355                   360                 365

Lys Gly Gln Ile Asp Ala Asn Ile Ala Asp Ala Met Gly Phe Gly Ser
370              375                  380

Ala Asn Lys Gly Val Val Leu Gly Gly Tyr Ser Ser Val Ser Ala Tyr
385              390                  395              400

Met Ser Ser Ala Gly Ser Gly Phe Ser Ser Gly Ser Gly Tyr Ser Val
              405                  410                  415

Gly Ser Gly Lys Asn Tyr Ser Thr Gly Phe Ala Asn Ala Ile Ala Ile
           420                   425                  430

Ser Ala Ala Ser Gln Leu Ser Thr Val Tyr Asn Val Ser Ala Gly Ser
             435                  440               445

Gly Phe Ser Ser Gly Ser Thr Leu Ser Gln Phe Ala Thr Met Lys Thr
         450                  455                460

Thr Ala Phe Gly Val Lys Asp Glu Thr Ala Gly Val Thr Thr Leu Lys
465              470                  475              480

Gly Ala Met Ala Val Met Asp Ile Ala Glu Thr Ala Ile Thr Asn Leu
             485                  490              495

Asp Gln Ile Arg Ala Asp Ile Gly Ser Val Gln Asn Gln Val Thr Ser
           500                  505              510

Thr Ile Asn Asn Ile Thr Val Thr Gln Val Asn Val Lys Ala Ala Glu
         515                  520              525

Ser Gln Ile Arg Asp Val Asp Phe Ala Ala Glu Ser Ala Asn Tyr Ser
   530                  535               540

Lys Ala Asn Ile Leu Ala Gln Ser Gly Ser Tyr Ala Met Ala Gln Ala
545              550                  555              560

Asn Ser Val Gln Gln Asn Val Leu Arg Leu Leu Gln
           565                   570

<210> SEQ ID NO 125
<211> LENGTH: 702
<212> TYPE: DNA
<213> ORGANISM: Campylobacter jejuni

<400> SEQUENCE: 125
atgaaaacaa ataatatctt tatggcttta gccatagttt tggcaagttt gattctagct        60
tttggattta acaaggcttt aagtgatttt aaaacacttg aaagaagtgt aagtgtaaag       120
ggtttaagtc aaaaagaagt cgaagcggat actttgatac ttcctataaa attcacaaga       180

```
tcaaacaaca atcttacaaa tttatacgaa gaactagaac aagataaaga aaatatcatc    240
aaatttttag aaaaacaagg cataaaagaa gatgagatca gctacaactc gccaaatatc    300
atagatcgtt taagcgatcc ttatagcaac gacactcaag ctgcataccg atacataggc    360
actgcgaatt tactcatcta tactcaaaat gtaaagcttg gaaaaagcat actagaaaac    420
atttcaagtc ttgcaaaatt tggtatagta acaaaaatcg atgattatga tatagaatac    480
ctttacacca agctaaatga tataaaacca caatgatgat aagaagcaac gctcaatgct    540
agaaatgcag cgataaaatt cgcacaagac tcaaacagcc atctaggcaa gataaaaaag    600
gcttctcaag gacaatttag cattagcaac agagataaaa acacccctta tatcaaaacc    660
ataagagtgg tttctactat agaatactac ttaaaagact ga                      702
```

<210> SEQ ID NO 126
<211> LENGTH: 233
<212> TYPE: PRT
<213> ORGANISM: Campylobacter jejuni

<400> SEQUENCE: 126

```
Met Lys Thr Asn Asn Ile Phe Met Ala Leu Ala Ile Val Leu Ala Ser
1               5                   10                  15

Leu Ile Leu Ala Phe Gly Phe Asn Lys Ala Leu Ser Asp Phe Lys Thr
            20                  25                  30

Leu Glu Arg Ser Val Ser Val Lys Gly Leu Ser Gln Lys Glu Val Glu
        35                  40                  45

Ala Asp Thr Leu Ile Leu Pro Ile Lys Phe Thr Arg Ser Asn Asn Asn
    50                  55                  60

Leu Thr Asn Leu Tyr Glu Glu Leu Glu Gln Asp Lys Glu Asn Ile Ile
65                  70                  75                  80

Lys Phe Leu Glu Lys Gln Gly Ile Lys Glu Asp Glu Ile Ser Tyr Asn
                85                  90                  95

Ser Pro Asn Ile Ile Asp Arg Leu Ser Asp Pro Tyr Ser Asn Asp Thr
            100                 105                 110

Gln Ala Ala Tyr Arg Tyr Ile Gly Thr Ala Asn Leu Leu Ile Tyr Thr
        115                 120                 125

Gln Asn Val Lys Leu Gly Lys Ser Ile Leu Glu Asn Ile Ser Ser Leu
    130                 135                 140

Ala Lys Phe Gly Ile Val Thr Lys Ile Asp Asp Tyr Asp Ile Glu Tyr
145                 150                 155                 160

Leu Tyr Thr Lys Leu Asn Asp Ile Lys Pro Gln Met Ile Glu Glu Ala
                165                 170                 175

Thr Leu Asn Ala Arg Asn Ala Ala Ile Lys Phe Ala Gln Asp Ser Asn
            180                 185                 190

Ser His Leu Gly Lys Ile Lys Lys Ala Ser Gln Gly Gln Phe Ser Ile
        195                 200                 205

Ser Asn Arg Asp Lys Asn Thr Pro Tyr Ile Lys Thr Ile Arg Val Val
    210                 215                 220

Ser Thr Ile Glu Tyr Tyr Leu Lys Asp
225                 230
```

<210> SEQ ID NO 127
<211> LENGTH: 837
<212> TYPE: DNA
<213> ORGANISM: Campylobacter jejuni

<400> SEQUENCE: 127

-continued

```
atggaaaatc aaaaaaatga atttgatgat attattttag aaaaaagtaa taaaagtgaa      60
aaagtaaaaa aaattctttt acgagttatt gctttagtta ttttgttttt agctatcatg     120
atagttatga agcttattaa tggtagtggt gatgaaaata cgcaaaatca aagtgtattg     180
ccaagtgaac ctatagcaac tcaagacaat aacaatgata cttcttttga agtatgcca     240
attacagata atacttcagc agaagatcaa tttgaggcat taagaaaaca atttcaagat     300
gaacaaaata caactcaaaa tacaacaacc tctagttcaa ataacaatga tactacaaat     360
tttgctatgc ctgatcaaga agttccagca gaaccaacag caactacttc agcaaatacc     420
actccacaag caagtactcc taaacaagaa gtaacacaaa ctgcaaaatc taagaagaa      480
gcaaaaaaac aaacagctgt aaaaaaagaa aagaaagtg caaaacaaac ccctaaaaaa      540
gaacaaaatg caaatgattt atttaaaaat gttgatgcta aacctgtaca tccaagtggt     600
ttagcatcgg gtatttatgt gcaaattttc tcagtaagta atttggatca aaaatcaaaa     660
gaacttgctt ctgtaaagca aaaaggttat gattataaac tttataaaac tacagttgga     720
agtaaagaaa ttaccaaggt tttaatagga ccatttgaaa aggcagatat tgcagcagaa     780
cttgctaaaa tccgtaagga tattgcaaaa gatgcttttt cttttacttt aaaatga       837
```

<210> SEQ ID NO 128
<211> LENGTH: 278
<212> TYPE: PRT
<213> ORGANISM: Campylobacter jejuni

<400> SEQUENCE: 128

```
Met Glu Asn Gln Lys Asn Glu Phe Asp Asp Ile Ile Leu Glu Lys Ser
1               5                   10                  15

Asn Lys Ser Glu Lys Val Lys Lys Ile Leu Leu Arg Val Ile Ala Leu
            20                  25                  30

Val Ile Leu Phe Leu Ala Ile Met Ile Val Met Lys Leu Ile Asn Gly
        35                  40                  45

Ser Gly Asp Glu Asn Thr Gln Asn Gln Ser Val Leu Pro Ser Glu Pro
    50                  55                  60

Ile Ala Thr Gln Asp Asn Asn Asn Asp Thr Ser Phe Glu Ser Met Pro
65                  70                  75                  80

Ile Thr Asp Asn Thr Ser Ala Glu Asp Gln Phe Glu Ala Leu Arg Lys
                85                  90                  95

Gln Phe Gln Asp Glu Gln Asn Thr Thr Gln Asn Thr Thr Ser Ser
            100                 105                 110

Ser Asn Asn Asn Asp Thr Thr Asn Phe Ala Met Pro Asp Gln Glu Val
        115                 120                 125

Pro Ala Glu Pro Thr Ala Thr Thr Ser Ala Asn Thr Thr Pro Gln Ala
    130                 135                 140

Ser Thr Pro Lys Gln Glu Val Thr Gln Thr Ala Lys Ser Lys Glu Glu
145                 150                 155                 160

Ala Lys Lys Gln Thr Ala Val Lys Lys Glu Lys Ser Ala Lys Gln
                165                 170                 175

Thr Pro Lys Lys Glu Gln Asn Ala Asn Asp Leu Phe Lys Asn Val Asp
            180                 185                 190

Ala Lys Pro Val His Pro Ser Gly Leu Ala Ser Gly Ile Tyr Val Gln
        195                 200                 205

Ile Phe Ser Val Ser Asn Leu Asp Gln Lys Ser Lys Glu Leu Ala Ser
    210                 215                 220
```

Val Lys Gln Lys Gly Tyr Asp Tyr Lys Leu Tyr Lys Thr Thr Val Gly
225                 230                 235                 240

Ser Lys Glu Ile Thr Lys Val Leu Ile Gly Pro Phe Glu Lys Ala Asp
            245                 250                 255

Ile Ala Ala Glu Leu Ala Lys Ile Arg Lys Asp Ile Ala Lys Asp Ala
        260                 265                 270

Phe Ser Phe Thr Leu Lys
        275

<210> SEQ ID NO 129
<211> LENGTH: 1479
<212> TYPE: DNA
<213> ORGANISM: Campylobacter jejuni

<400> SEQUENCE: 129
atgaataaaa taatttcaat tagtgctata gcaagtttta ctcttttgat ttcagcttgc        60
tctttaagtc caaatttaaa tattcccgaa gcaaactata gcattgataa taagcttgga      120
gccttatctt gggaaaaaga aaacaatagc tctatcacaa aaaattggtg gaaagacttt      180
gatgatgaaa atttaaataa agtggttgat ttagcactta aaaataataa tgatttaaaa      240
cttgctttca tacacatgga acaagctgct gctcaattag gtatagattt tagcagtttg      300
ttgccaaaat tgatggtag cgcaagcgga agtcgtgcaa aaacagctat aaatgctcca      360
agcaatcgaa ctggggaagt aagttacggt aatgatttta aatgggact taatttaagc      420 tatgaaatcg atctttgggg aaaatatcgc gatacatatc gcgcctcaaa atcaggcttt      480
aaagcaagtg agtatgatta tgaagctgca agactttctg ttatttcaaa tacagttcaa      540
acttatttta atcttgtaaa tgcttatgaa aatgaaaatg ctcttaaaga agcctataaa      600
tctgcaaaag aaatttatag gattaatgat gaaaaatttc aagttggtgc tgtaggtgaa      660
tatgaacttg ctcaagcaag agccaactta gaaagtatgg ctttgcaata taatgaagca      720
aagttaaata agaaaaatta ccttaaagct ttaaaaattt taacttcaaa tgatttaaat      780
gacatacttt acaaaaatca aagctatcaa gttttttaatc ttaaagaatt tgacattcca      840
actggaattt caagtaccat cttgcttcaa cgtccagata ttggctcttc tttagaaaaa      900
ttaactcagc aaaattatct tgttggagta gctcgcacgg ctttcttacc tagccttct      960 ttaacaggat tatttgggatt tgaaagcggg gatttagata ccttggttaa aggaggttct     1020
aagacttgga atataggtgg aaactttact ctgcctattt ttcattgggg tgaaatttac     1080
caaaatgtaa atttagccaa gcttaataaa gatgaagctt ttgtaaatta tcaaaatact     1140
ttgattactg cttttggaga aattcgctat gctttagtag ctagaaaaac tatacgctta     1200
caatacgata tgcacaagc aagcgaacaa tcttacaaaa gaatctatga aattgctaaa     1260
gaacgctatg atataggaga atgtctttg caagattatt tagaggcacg tcaaaattgg     1320
cttaatgctg cggttgcttt taataatatt aaatattctt atgccaattc catagtagat     1380
gtaatcaaag catttggtgg aggatttgag caaagtgaag atacgagtaa aaatataaaa     1440
gaagaatcaa aaaatttaga tatgtctttt agagaatag                            1479

<210> SEQ ID NO 130
<211> LENGTH: 492
<212> TYPE: PRT
<213> ORGANISM: Campylobacter jejuni

<400> SEQUENCE: 130

Met Asn Lys Ile Ile Ser Ile Ser Ala Ile Ala Ser Phe Thr Leu Leu

```
            1               5                  10                 15
        Ile Ser Ala Cys Ser Leu Ser Pro Asn Leu Asn Ile Pro Glu Ala Asn
                    20                  25                  30
        Tyr Ser Ile Asp Asn Lys Leu Gly Ala Leu Ser Trp Glu Lys Glu Asn
                    35                  40                  45
        Asn Ser Ser Ile Thr Lys Asn Trp Trp Lys Asp Phe Asp Asp Glu Asn
                    50                  55                  60
        Leu Asn Lys Val Val Asp Leu Ala Leu Lys Asn Asn Asn Asp Leu Lys
        65                  70                  75                  80
        Leu Ala Phe Ile His Met Glu Gln Ala Ala Gln Leu Gly Ile Asp
                            85                  90                  95
        Phe Ser Ser Leu Leu Pro Lys Phe Asp Gly Ser Ala Gly Ser Arg
                        100                 105                 110
        Ala Lys Thr Ala Ile Asn Ala Pro Ser Asn Arg Thr Gly Glu Val Ser
                        115                 120                 125
        Tyr Gly Asn Asp Phe Lys Met Gly Leu Asn Leu Ser Tyr Glu Ile Asp
                    130                 135                 140
        Leu Trp Gly Lys Tyr Arg Asp Thr Tyr Arg Ala Ser Lys Ser Gly Phe
        145                 150                 155                 160
        Lys Ala Ser Glu Tyr Asp Tyr Glu Ala Ala Arg Leu Ser Val Ile Ser
                        165                 170                 175
        Asn Thr Val Gln Thr Tyr Phe Asn Leu Val Asn Ala Tyr Glu Asn Glu
                        180                 185                 190
        Asn Ala Leu Lys Glu Ala Tyr Lys Ser Ala Lys Glu Ile Tyr Arg Ile
                    195                 200                 205
        Asn Asp Glu Lys Phe Gln Val Gly Ala Val Gly Tyr Glu Leu Ala
                210                 215                 220
        Gln Ala Arg Ala Asn Leu Glu Ser Met Ala Leu Gln Tyr Asn Glu Ala
        225                 230                 235                 240
        Lys Leu Asn Lys Glu Asn Tyr Leu Lys Ala Leu Lys Ile Leu Thr Ser
                        245                 250                 255
        Asn Asp Leu Asn Asp Ile Leu Tyr Lys Asn Gln Ser Tyr Gln Val Phe
                    260                 265                 270
        Asn Leu Lys Glu Phe Asp Ile Pro Thr Gly Ile Ser Ser Thr Ile Leu
                    275                 280                 285
        Leu Gln Arg Pro Asp Ile Gly Ser Ser Leu Glu Lys Leu Thr Gln Gln
                    290                 295                 300
        Asn Tyr Leu Val Gly Val Ala Arg Thr Ala Phe Leu Pro Ser Leu Ser
        305                 310                 315                 320
        Leu Thr Gly Leu Leu Gly Phe Glu Ser Gly Asp Leu Asp Thr Leu Val
                        325                 330                 335
        Lys Gly Gly Ser Lys Thr Trp Asn Ile Gly Gly Asn Phe Thr Leu Pro
                    340                 345                 350
        Ile Phe His Trp Gly Glu Ile Tyr Gln Asn Val Asn Leu Ala Lys Leu
                    355                 360                 365
        Asn Lys Asp Glu Ala Phe Val Asn Tyr Gln Asn Thr Leu Ile Thr Ala
                370                 375                 380
        Phe Gly Glu Ile Arg Tyr Ala Leu Val Ala Arg Lys Thr Ile Arg Leu
        385                 390                 395                 400
        Gln Tyr Asp Asn Ala Gln Ala Ser Glu Gln Ser Tyr Lys Arg Ile Tyr
                        405                 410                 415
        Glu Ile Ala Lys Glu Arg Tyr Asp Ile Gly Glu Met Ser Leu Gln Asp
                    420                 425                 430
```

Tyr Leu Glu Ala Arg Gln Asn Trp Leu Asn Ala Ala Val Ala Phe Asn
            435                 440                 445

Asn Ile Lys Tyr Ser Tyr Ala Asn Ser Ile Val Asp Val Ile Lys Ala
    450                 455                 460

Phe Gly Gly Phe Glu Gln Ser Glu Asp Thr Ser Lys Asn Ile Lys
465                 470                 475                 480

Glu Glu Ser Lys Asn Leu Asp Met Ser Phe Arg Glu
            485                 490

<210> SEQ ID NO 131
<211> LENGTH: 2091
<212> TYPE: DNA
<213> ORGANISM: Campylobacter jejuni

<400> SEQUENCE: 131

| | | |
|---|---|---|
| atgaaaaaaa tatgtctatc agtttgcgcc attggtctct taagctccaa tgccatatcg | 60 |
| caaaatgtag aactagatag ctcaatcgtt agtgcttctg ctttaccca agatattaaa | 120 |
| gaagctcctg ctactatcaa tgttatcact aaaaaagaat acaaagtaa gccttataga | 180 |
| gatgttgcag aggctatcgc agatatccca ggcgttgatt tatatgctag caagggaaaa | 240 |
| acaggttctt ataatatcac tatgaggggt attactggat atactttggt tttgattgat | 300 |
| gggcgtcgtc agggtattgg cggagaggtg ggccctaatg gttttaatga aatttcaaat | 360 |
| tctttcttac ctccgatttc tagtatagaa aggatagaag ttataaaagg tcctatgagt | 420 |
| actttatatg ctctgaagc tttaggcggg gtggtaaata tcattaccaa aaaagtaagt | 480 |
| gataaatggg aaacttctgt aagtttggat gctcttttaa atgaaaataa agattggggt | 540 |
| aatacttatg gaacaagtat ttattctagt ggtccttga tgaatgacaa attgggtcta | 600 |
| acacttcgat ttagagaatt ttacagacag caatctaatg ttgaatttac aaatggaagt | 660 |
| ggacaaagag ttcaaggaga tcaagctcaa agtcctacaa aggcaaataa ttttaacata | 720 |
| ggaacaagaa ttagttattt ggctaatgat tataatacct ttatatttga tatagatttt | 780 |
| tcaagaaatc attatgataa taaacaaggt caattaggaa ccatcacaag tccaggtaga | 840 |
| acaccaggta gcttaacggg tggttatgca gatattatgg aagttgataa atttgtgact | 900 |
| tatttaagtc atgagggtgt ttatgaaaat ttttctatca cttctggttt gcaatataat | 960 |
| agagtgagca atgatggccg cgaagtcgta gggcaatcta cacagccgtt tttgggagaa | 1020 |
| aatagagata tagtcgcaga agatattatc ttagatacta gtctgttat tcctctagga | 1080 |
| caaagtcata ttttaagcgt aggcggtgaa tataggcttg aaaaaatgca agataaaata | 1140 |
| gctagtccta ctaattttga tcagtattta ttggcaattt ttgcagagga tgagtatagt | 1200 |
| ataaaagatg atttaagact tacttttgga gcaagatata atcatcatga aattttggaa | 1260 |
| aacaatgttt cgccaagagc ttatgtggtt tataatccta ctaatgagct tactttaaaa | 1320 |
| ggcggtgtat ctacaggctt tagaaccccct atgcaaaacc gttgataaa tggaacttac | 1380 |
| agttatagtg ccaaggcag atttcctaca tatggaaatc ctgatttaaa agaagagaca | 1440 |
| tctttaaact atgaaatagc agctatttac aataatgatt tatttttatgt ttcagcaaca | 1500 |
| ggttttttaa cgaattttaa agataaaatt tcaagtcaaa gttataataa tagcgaacca | 1560 |
| atcccaggta ttggcacttg tgatgctgat agatgttcta gagcaatcaa tcatggcaag | 1620 |
| gttgaataca aaggtgtaga acttggagca gggataagcc ctcttgataa tttaaatgta | 1680 |
| aattttgctt atacttatct tgatactgaa gttaaagaag cacaagatag aagtgtgata | 1740 |

-continued

```
ggtaaacctg aacaagatag tttaaaacac aatatcatgt taaaaaccga atacagcttc   1800
tataataaaa ttaccccttg gataaaaggc gagtggcaaa tagatcgcta tatgggtgat   1860
actaatatca atagagaata ttacaaggat atcttttag cttccatggg tgtgcgttat    1920
gatatcaaca acaatggag tatcaatgca gctatttata atcttttga caaaagcttt    1980 acaaatggct gggaatctta tgcaagtggg agtggtagca cttgggtaaa tacctataac   2040
cgtatagaag aaggaagaag aatgtatatt tctatcaatg gtaacttta a             2091
```

<210> SEQ ID NO 132
<211> LENGTH: 696
<212> TYPE: PRT
<213> ORGANISM: Campylobacter jejuni

<400> SEQUENCE: 132

```
Met Lys Lys Ile Cys Leu Ser Val Cys Ala Ile Gly Leu Leu Ser Ser
1               5                   10                  15

Asn Ala Ile Ser Gln Asn Val Glu Leu Asp Ser Ser Ile Val Ser Ala
            20                  25                  30

Ser Gly Phe Thr Gln Asp Ile Lys Glu Ala Pro Ala Thr Ile Asn Val
        35                  40                  45

Ile Thr Lys Lys Glu Leu Gln Ser Lys Pro Tyr Arg Asp Val Ala Glu
    50                  55                  60

Ala Ile Ala Asp Ile Pro Gly Val Asp Leu Tyr Ala Ser Lys Gly Lys
65                  70                  75                  80

Thr Gly Ser Tyr Asn Ile Thr Met Arg Gly Ile Thr Gly Tyr Thr Leu
                85                  90                  95

Val Leu Ile Asp Gly Arg Arg Gln Gly Ile Gly Gly Glu Val Gly Pro
            100                 105                 110

Asn Gly Phe Asn Glu Ile Ser Asn Ser Phe Leu Pro Pro Ile Ser Ser
        115                 120                 125

Ile Glu Arg Ile Glu Val Ile Lys Gly Pro Met Ser Thr Leu Tyr Gly
    130                 135                 140

Ser Glu Ala Leu Gly Gly Val Val Asn Ile Ile Thr Lys Lys Val Ser
145                 150                 155                 160

Asp Lys Trp Glu Thr Ser Val Ser Leu Asp Ala Leu Leu Asn Glu Asn
                165                 170                 175

Lys Asp Trp Gly Asn Thr Tyr Gly Thr Ser Ile Tyr Ser Ser Gly Pro
            180                 185                 190

Leu Met Asn Asp Lys Leu Gly Leu Thr Leu Arg Phe Arg Glu Phe Tyr
        195                 200                 205

Arg Gln Gln Ser Asn Val Glu Phe Thr Asn Gly Ser Gly Gln Arg Val
    210                 215                 220

Gln Gly Asp Gln Ala Gln Ser Pro Thr Lys Ala Asn Asn Phe Asn Ile
225                 230                 235                 240

Gly Thr Arg Ile Ser Tyr Leu Ala Asn Asp Tyr Asn Thr Phe Ile Phe
                245                 250                 255

Asp Ile Asp Phe Ser Arg Asn His Tyr Asp Asn Lys Gln Gly Gln Leu
            260                 265                 270

Gly Thr Ile Thr Ser Pro Gly Arg Thr Pro Gly Ser Leu Thr Gly Gly
        275                 280                 285

Tyr Ala Asp Ile Met Glu Val Asp Lys Phe Val Thr Tyr Leu Ser His
    290                 295                 300

Glu Gly Val Tyr Glu Asn Phe Ser Ile Thr Ser Gly Leu Gln Tyr Asn
305                 310                 315                 320
```

```
Arg Val Ser Asn Asp Gly Arg Glu Val Val Gly Gln Ser Thr Gln Pro
            325                 330                 335

Phe Leu Gly Glu Asn Arg Asp Ile Val Ala Glu Asp Ile Ile Leu Asp
            340                 345                 350

Thr Lys Ser Val Ile Pro Leu Gly Gln Ser His Ile Leu Ser Val Gly
            355                 360                 365

Gly Glu Tyr Arg Leu Glu Lys Met Gln Asp Lys Ile Ala Ser Pro Thr
            370                 375                 380

Asn Phe Asp Gln Tyr Leu Leu Ala Ile Phe Ala Glu Asp Glu Tyr Ser
385                 390                 395                 400

Ile Lys Asp Asp Leu Arg Leu Thr Phe Gly Ala Arg Tyr Asn His His
                405                 410                 415

Glu Ile Phe Gly Asn Asn Val Ser Pro Arg Ala Tyr Val Val Tyr Asn
            420                 425                 430

Pro Thr Asn Glu Leu Thr Leu Lys Gly Gly Val Ser Thr Gly Phe Arg
            435                 440                 445

Thr Pro Tyr Ala Asn Arg Leu Ile Asn Gly Thr Tyr Ser Tyr Ser Gly
            450                 455                 460

Gln Gly Arg Phe Pro Thr Tyr Gly Asn Pro Asp Leu Lys Glu Glu Thr
465                 470                 475                 480

Ser Leu Asn Tyr Glu Ile Ala Ala Ile Tyr Asn Asn Asp Leu Phe Tyr
                485                 490                 495

Val Ser Ala Thr Gly Phe Leu Thr Asn Phe Lys Asp Lys Ile Ser Ser
            500                 505                 510

Gln Ser Tyr Asn Asn Ser Glu Pro Ile Pro Gly Ile Gly Thr Cys Asp
            515                 520                 525

Ala Asp Arg Cys Ser Arg Ala Ile Asn His Gly Lys Val Glu Tyr Lys
            530                 535                 540

Gly Val Glu Leu Gly Ala Gly Ile Ser Pro Leu Asp Asn Leu Asn Val
545                 550                 555                 560

Asn Phe Ala Tyr Thr Tyr Leu Asp Thr Glu Val Lys Glu Ala Gln Asp
                565                 570                 575

Arg Ser Val Ile Gly Lys Pro Glu Gln Asp Ser Leu Lys His Asn Ile
            580                 585                 590

Met Leu Lys Thr Glu Tyr Ser Phe Tyr Asn Lys Ile Thr Pro Trp Ile
            595                 600                 605

Lys Gly Glu Trp Gln Ile Asp Arg Tyr Met Gly Asp Thr Asn Ile Asn
            610                 615                 620

Arg Glu Tyr Tyr Lys Asp Ile Phe Leu Ala Ser Met Gly Val Arg Tyr
625                 630                 635                 640

Asp Ile Asn Lys Gln Trp Ser Ile Asn Ala Ala Ile Tyr Asn Leu Phe
                645                 650                 655

Asp Lys Ser Phe Thr Asn Gly Trp Glu Ser Tyr Ala Ser Gly Ser Gly
            660                 665                 670

Ser Thr Trp Val Asn Thr Tyr Asn Arg Ile Glu Glu Gly Arg Arg Met
            675                 680                 685

Tyr Ile Ser Ile Asn Gly Asn Phe
    690                 695

<210> SEQ ID NO 133
<211> LENGTH: 573
<212> TYPE: DNA
<213> ORGANISM: Campylobacter jejuni
```

<400> SEQUENCE: 133

```
atgaaaaaag tttttattgag ttcattggtt gcggtgtctt tgttaagcac aggtttgttt       60
gctaaagaat atactttaga taaagcacat acagatgtag gttttaaaat caaacattta      120
caaattagca atgtaaaagg aaatttcaaa gattattctg cggtgattga ttttgatcct      180
gcgagtgctg aatttaaaaa gcttgatgta actataaaaa tcgcatctgt aaatacagaa      240
aatcaaacaa gagataatca cttacaacaa gatgattttt tcaaagcaaa aaaatatcct      300
gatatgactt ttacaatgaa aaaatatgaa aaaatcgata tgaaaaagg caaaatgaca       360
ggaactttaa ctatagctgg agtttctaaa gatatcgttt tagatgctga atcggcggt       420
gtagctaaag gcaaagatgg aaaagaaaaa ataggatttt ctttaaatgg aaaaatcaaa      480
cgctctgatt ttaaatttgc aacaagtact tcaactatta ctttaagtga tgatattaat      540
ttaaatatcg aagttgaagc gaacgaaaaa taa                                   573
```

<210> SEQ ID NO 134
<211> LENGTH: 190
<212> TYPE: PRT
<213> ORGANISM: Campylobacter jejuni

<400> SEQUENCE: 134

```
Met Lys Lys Val Leu Leu Ser Ser Leu Val Ala Val Ser Leu Leu Ser
1               5                   10                  15

Thr Gly Leu Phe Ala Lys Glu Tyr Thr Leu Asp Lys Ala His Thr Asp
            20                  25                  30

Val Gly Phe Lys Ile Lys His Leu Gln Ile Ser Asn Val Lys Gly Asn
        35                  40                  45

Phe Lys Asp Tyr Ser Ala Val Ile Asp Phe Asp Pro Ala Ser Ala Glu
    50                  55                  60

Phe Lys Lys Leu Asp Val Thr Ile Lys Ile Ala Ser Val Asn Thr Glu
65                  70                  75                  80

Asn Gln Thr Arg Asp Asn His Leu Gln Gln Asp Phe Phe Lys Ala
                85                  90                  95

Lys Lys Tyr Pro Asp Met Thr Phe Thr Met Lys Lys Tyr Glu Lys Ile
            100                 105                 110

Asp Asn Glu Lys Gly Lys Met Thr Gly Thr Leu Thr Ile Ala Gly Val
        115                 120                 125

Ser Lys Asp Ile Val Leu Asp Ala Glu Ile Gly Gly Val Ala Lys Gly
    130                 135                 140

Lys Asp Gly Lys Glu Lys Ile Gly Phe Ser Leu Asn Gly Lys Ile Lys
145                 150                 155                 160

Arg Ser Asp Phe Lys Phe Ala Thr Ser Thr Ser Thr Ile Thr Leu Ser
                165                 170                 175

Asp Asp Ile Asn Leu Asn Ile Glu Val Glu Ala Asn Glu Lys
            180                 185                 190
```

<210> SEQ ID NO 135
<211> LENGTH: 8
<212> TYPE: PRT
<213> ORGANISM: Artificial Sequence
<220> FEATURE:
<223> OTHER INFORMATION: Synthetic

<400> SEQUENCE: 135

```
Asn Lys Gly Val Ile Ser Ala Lys
1               5
```

```
<210> SEQ ID NO 136
<211> LENGTH: 65
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is R or I
<220> FEATURE:
<221> NAME/KEY: MISC_FEATURE
<222> LOCATION: (3)..(3)
<223> OTHER INFORMATION: X is F or absent
<220> FEATURE:
<221> NAME/KEY: MISC_FEATURE
<222> LOCATION: (4)..(4)
<223> OTHER INFORMATION: X is D or absent
<220> FEATURE:
<221> NAME/KEY: MISC_FEATURE
<222> LOCATION: (7)..(7)
<223> OTHER INFORMATION: X is V or I
<220> FEATURE:
<221> NAME/KEY: MISC_FEATURE
<222> LOCATION: (12)..(12)
<223> OTHER INFORMATION: X is N or D
<220> FEATURE:
<221> NAME/KEY: MISC_FEATURE
<222> LOCATION: (24)..(24)
<223> OTHER INFORMATION: X is N or S
<220> FEATURE:
<221> NAME/KEY: MISC_FEATURE
<222> LOCATION: (27)..(27)
<223> OTHER INFORMATION: X is I or V
<220> FEATURE:
<221> NAME/KEY: MISC_FEATURE
<222> LOCATION: (33)..(33)
<223> OTHER INFORMATION: X is S or N
<220> FEATURE:
<221> NAME/KEY: MISC_FEATURE
<222> LOCATION: (38)..(38)
<223> OTHER INFORMATION: X is F or C
<220> FEATURE:
<221> NAME/KEY: MISC_FEATURE
<222> LOCATION: (43)..(43)
<223> OTHER INFORMATION: X is F or L
<220> FEATURE:
<221> NAME/KEY: MISC_FEATURE
<222> LOCATION: (50)..(50)
<223> OTHER INFORMATION: X is T, A or K
<220> FEATURE:
<221> NAME/KEY: MISC_FEATURE
<222> LOCATION: (55)..(55)
<223> OTHER INFORMATION: X is P, L or S
<220> FEATURE:
<221> NAME/KEY: MISC_FEATURE
<222> LOCATION: (57)..(57)
<223> OTHER INFORMATION: X is D or E
<220> FEATURE:
<221> NAME/KEY: MISC_FEATURE
<222> LOCATION: (58)..(58)
<223> OTHER INFORMATION: X is I or V
<220> FEATURE:
<221> NAME/KEY: MISC_FEATURE
<222> LOCATION: (59)..(59)
<223> OTHER INFORMATION: X is L or Y
<220> FEATURE:
<221> NAME/KEY: MISC_FEATURE
<222> LOCATION: (61)..(61)
<223> OTHER INFORMATION: X is A, T or S
<220> FEATURE:
<221> NAME/KEY: MISC_FEATURE
<222> LOCATION: (62)..(62)
<223> OTHER INFORMATION: X is N, D or K
<220> FEATURE:
<221> NAME/KEY: MISC_FEATURE
<222> LOCATION: (63)..(63)
<223> OTHER INFORMATION: X is E or G
```

```
<220> FEATURE:
<221> NAME/KEY: MISC_FEATURE
<222> LOCATION: (65)..(65)
<223> OTHER INFORMATION: X is K or N

<400> SEQUENCE: 136

Met Xaa Xaa Xaa Phe Phe Xaa Ser Lys Arg Leu Xaa Ile Ser Arg Asn
1               5                   10                  15

Lys Ala Leu Glu Leu Ile Glu Xaa Glu Glu Xaa Leu Leu Asn Gly Lys
            20                  25                  30

Xaa Phe Lys Ala Ser Xaa Asp Val Lys Asn Xaa Leu Glu Asn Leu Lys
        35                  40                  45

Lys Xaa Gln Asp Leu Asn Xaa Glu Xaa Xaa Xaa Leu Xaa Xaa Xaa Leu
    50                  55                  60

Xaa
65

<210> SEQ ID NO 137
<211> LENGTH: 125
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is D or E
<220> FEATURE:
<221> NAME/KEY: MISC_FEATURE
<222> LOCATION: (3)..(3)
<223> OTHER INFORMATION: X is D or E
<220> FEATURE:
<221> NAME/KEY: MISC_FEATURE
<222> LOCATION: (6)..(6)
<223> OTHER INFORMATION: X is A or T
<220> FEATURE:
<221> NAME/KEY: MISC_FEATURE
<222> LOCATION: (10)..(10)
<223> OTHER INFORMATION: X is E, K or absent
<220> FEATURE:
<221> NAME/KEY: MISC_FEATURE
<222> LOCATION: (11)..(11)
<223> OTHER INFORMATION: X is T or absent
<220> FEATURE:
<221> NAME/KEY: MISC_FEATURE
<222> LOCATION: (13)..(13)
<223> OTHER INFORMATION: X is N, S or I
<220> FEATURE:
<221> NAME/KEY: MISC_FEATURE
<222> LOCATION: (16)..(16)
<223> OTHER INFORMATION: X is L or I
<220> FEATURE:
<221> NAME/KEY: MISC_FEATURE
<222> LOCATION: (37)..(37)
<223> OTHER INFORMATION: X is H or Y
<220> FEATURE:
<221> NAME/KEY: MISC_FEATURE
<222> LOCATION: (44)..(44)
<223> OTHER INFORMATION: X is V or I
<220> FEATURE:
<221> NAME/KEY: MISC_FEATURE
<222> LOCATION: (53)..(53)
<223> OTHER INFORMATION: X is R or H
<220> FEATURE:
<221> NAME/KEY: MISC_FEATURE
<222> LOCATION: (61)..(61)
<223> OTHER INFORMATION: X is K or E
<220> FEATURE:
<221> NAME/KEY: MISC_FEATURE
<222> LOCATION: (77)..(77)
<223> OTHER INFORMATION: X is A or T
```

```
<220> FEATURE:
<221> NAME/KEY: MISC_FEATURE
<222> LOCATION: (87)..(87)
<223> OTHER INFORMATION: X is A, V or T
<220> FEATURE:
<221> NAME/KEY: MISC_FEATURE
<222> LOCATION: (95)..(95)
<223> OTHER INFORMATION: X is K or E
<220> FEATURE:
<221> NAME/KEY: MISC_FEATURE
<222> LOCATION: (99)..(125)
<223> OTHER INFORMATION: Amino Acids are optionally absent
<220> FEATURE:
<221> NAME/KEY: MISC_FEATURE
<222> LOCATION: (107)..(107)
<223> OTHER INFORMATION: X is N or D
<220> FEATURE:
<221> NAME/KEY: MISC_FEATURE
<222> LOCATION: (115)..(115)
<223> OTHER INFORMATION: X is N or S
<220> FEATURE:
<221> NAME/KEY: MISC_FEATURE
<222> LOCATION: (122)..(122)
<223> OTHER INFORMATION: X is N or D
<220> FEATURE:
<221> NAME/KEY: MISC_FEATURE
<222> LOCATION: (123)..(123)
<223> OTHER INFORMATION: X is K or E

<400> SEQUENCE: 137

Xaa Lys Xaa Phe Leu Xaa Phe Leu Asn Xaa Xaa Lys Xaa Glu Asn Xaa
1               5                   10                  15

Ala Leu Ala Glu Asn Glu Phe Leu Gly Val Asp His Ile Ser Phe Leu
            20                  25                  30

Gly Phe Leu Leu Xaa Arg Trp Asn Phe Asp Asp Xaa Leu Ile Glu Ser
        35                  40                  45

Ile Cys Phe Val Xaa Thr Pro His Ala Arg Glu Xaa Val Lys Lys
    50                  55                  60

Ser Ala Tyr Ala Leu Ala Ile Thr Asp His Leu Phe Xaa Pro His Asp
65              70                  75                  80

Gly Ser Ser Pro Phe Asn Xaa Lys Ala Ala Val Ala Leu Leu Xaa Glu
            85                  90                  95

Ala Lys Thr Gln Gly Ile Asn Phe Asp Leu Xaa Asn Leu Leu Ser Lys
            100                 105                 110

Leu Pro Xaa Lys Ala Lys Glu Asn Leu Xaa Xaa Glu Asp
        115                 120                 125

<210> SEQ ID NO 138
<211> LENGTH: 102
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is D or E
<220> FEATURE:
<221> NAME/KEY: MISC_FEATURE
<222> LOCATION: (3)..(3)
<223> OTHER INFORMATION: X is D or E
<220> FEATURE:
<221> NAME/KEY: MISC_FEATURE
<222> LOCATION: (6)..(6)
<223> OTHER INFORMATION: X is A or T
<220> FEATURE:
<221> NAME/KEY: MISC_FEATURE
<222> LOCATION: (10)..(10)
<223> OTHER INFORMATION: X is E, K or absent
```

```
<220> FEATURE:
<221> NAME/KEY: MISC_FEATURE
<222> LOCATION: (11)..(11)
<223> OTHER INFORMATION: X is T or absent
<220> FEATURE:
<221> NAME/KEY: MISC_FEATURE
<222> LOCATION: (13)..(13)
<223> OTHER INFORMATION: X is N, S, or I
<220> FEATURE:
<221> NAME/KEY: MISC_FEATURE
<222> LOCATION: (16)..(16)
<223> OTHER INFORMATION: X is L or I
<220> FEATURE:
<221> NAME/KEY: MISC_FEATURE
<222> LOCATION: (37)..(37)
<223> OTHER INFORMATION: X is H or Y
<220> FEATURE:
<221> NAME/KEY: MISC_FEATURE
<222> LOCATION: (44)..(44)
<223> OTHER INFORMATION: X is V or I
<220> FEATURE:
<221> NAME/KEY: MISC_FEATURE
<222> LOCATION: (53)..(53)
<223> OTHER INFORMATION: X is R or H
<220> FEATURE:
<221> NAME/KEY: MISC_FEATURE
<222> LOCATION: (61)..(61)
<223> OTHER INFORMATION: X is K or E
<220> FEATURE:
<221> NAME/KEY: MISC_FEATURE
<222> LOCATION: (77)..(77)
<223> OTHER INFORMATION: X is A or T
<220> FEATURE:
<221> NAME/KEY: MISC_FEATURE
<222> LOCATION: (87)..(87)
<223> OTHER INFORMATION: X is A, V or T
<220> FEATURE:
<221> NAME/KEY: MISC_FEATURE
<222> LOCATION: (95)..(95)
<223> OTHER INFORMATION: X is K or E
<220> FEATURE:
<221> NAME/KEY: MISC_FEATURE
<222> LOCATION: (99)..(102)
<223> OTHER INFORMATION: Amino Acids are optionally absent

<400> SEQUENCE: 138

Xaa Lys Xaa Phe Leu Xaa Phe Leu Asn Xaa Xaa Lys Xaa Glu Asn Xaa
1               5                   10                  15

Ala Leu Ala Glu Asn Glu Phe Leu Gly Val Asp His Ile Ser Phe Leu
            20                  25                  30

Gly Phe Leu Leu Xaa Arg Trp Asn Phe Asp Asp Xaa Leu Ile Glu Ser
        35                  40                  45

Ile Cys Phe Val Xaa Thr Pro His Ala Ala Arg Glu Xaa Val Lys Lys
    50                  55                  60

Ser Ala Tyr Ala Leu Ala Ile Thr Asp His Leu Phe Xaa Pro His Asp
65                  70                  75                  80

Gly Ser Ser Pro Phe Asn Xaa Lys Ala Ala Val Ala Leu Leu Xaa Glu
                85                  90                  95

Ala Lys Asn Ser Arg Asn
            100

<210> SEQ ID NO 139
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: X is N or D
```

```
<220> FEATURE:
<221> NAME/KEY: MISC_FEATURE
<222> LOCATION: (17)..(17)
<223> OTHER INFORMATION: X is N or S
<220> FEATURE:
<221> NAME/KEY: MISC_FEATURE
<222> LOCATION: (24)..(24)
<223> OTHER INFORMATION: X is N or D
<220> FEATURE:
<221> NAME/KEY: MISC_FEATURE
<222> LOCATION: (25)..(25)
<223> OTHER INFORMATION: X is K or E

<400> SEQUENCE: 139

Thr Gln Gly Ile Asn Phe Asp Leu Xaa Asn Leu Leu Ser Lys Leu Pro
1               5                   10                  15
Xaa Lys Ala Lys Glu Asn Leu Xaa Xaa Glu Asp
            20                  25

<210> SEQ ID NO 140
<211> LENGTH: 4
<212> TYPE: PRT
<213> ORGANISM: Artificial Sequence
<220> FEATURE:
<223> OTHER INFORMATION: Synthetic

<400> SEQUENCE: 140

Asn Ser Arg Asn
1

<210> SEQ ID NO 141
<211> LENGTH: 450
<212> TYPE: DNA
<213> ORGANISM: Campylobacter jejuni

<400> SEQUENCE: 141
atgtcagtta caaaacaatt attacaaatg caagcagatg ctcatcattt atgggttaaa      60
tttcataatt atcactggaa tgtaaaaggt ttgcaatttt tttctataca cgagtacaca     120
gaaaaagctt atgaagaaat ggcagaactt tttgatagtt gtgctgaaag agttttacaa     180
cttggcgaaa aagctatcac ttgccaaaaa gtttttaatgg aaaatgcaaa aagtccaaaa    240
gttgcaaaag attgctttac tccgcttgaa gtcatagaac tgatcaaaca agattatgaa     300
tatcttttag cagaatttaa aaaactcaat gaagcagcag aaaaagaaag tgatactaca     360
acagctgctt ttgcacaaga aaatatcgca aaatatgaaa aaagtctttg gatgataggc     420
gctactttac aaggtgcttg caaaatgtaa                                      450

<210> SEQ ID NO 142
<211> LENGTH: 149
<212> TYPE: PRT
<213> ORGANISM: Campylobacter jejuni

<400> SEQUENCE: 142

Met Ser Val Thr Lys Gln Leu Leu Gln Met Gln Ala Asp Ala His His
1               5                   10                  15
Leu Trp Val Lys Phe His Asn Tyr His Trp Asn Val Lys Gly Leu Gln
            20                  25                  30
Phe Phe Ser Ile His Glu Tyr Thr Gln Lys Ala Tyr Glu Glu Met Ala
        35                  40                  45
Glu Leu Phe Asp Ser Cys Ala Glu Arg Val Leu Gln Leu Gly Glu Lys
    50                  55                  60
```

-continued

```
Ala Ile Thr Cys Gln Lys Val Leu Met Glu Asn Ala Lys Ser Pro Lys
 65              70                  75                  80

Val Ala Lys Asp Cys Phe Thr Pro Leu Glu Val Ile Glu Leu Ile Lys
                 85                  90                  95

Gln Asp Tyr Glu Tyr Leu Leu Ala Glu Phe Lys Lys Leu Asn Glu Ala
            100                 105                 110

Ala Glu Lys Glu Ser Asp Thr Thr Ala Ala Phe Ala Gln Glu Asn
        115                 120                 125

Ile Ala Lys Tyr Glu Lys Ser Leu Trp Met Ile Gly Ala Thr Leu Gln
        130                 135                 140

Gly Ala Cys Lys Met
145
```

CAMPYLOBACTER IMMUNOGENIC COMPOSITIONS AND USES THEREOF

CROSS REFERENCE

This application is a U.S. National Phase of International Application No. PCT/US2013/024332, filed Feb. 1, 2013, which claims priority to U.S. Provisional Application No. 61/689,078, filed May 29, 2012 and U.S. Provisional Application No. 61/632,888, filed Feb. 1, 2012, the disclosures of which are hereby incorporated by reference in their entireties.

STATEMENT OF GOVERNMENT SUPPORT

This invention was made with government support under grant number 127032 awarded by United States Department of Agriculture Hatch Funding. The government has certain rights in the invention.

BACKGROUND

Campylobacteriosis is primarily a food-borne disease with the handling and consumption of poultry considered to be the most significant risk factor in transmission. Infection by *Campylobacter* spp. is one of the leading causes of bacterial gastroenteritis, causing an estimated 1.3 million cases annually in the U.S. (Scallan et al, 2011), resulting in health care costs of $0.8-5.6 billion per year (Buzby et al., 1997). Serious complications such as arthritis occur in an estimated 1-5% of cases (Pope et al., 2007)) and Guillain-Barre Syndrome, a form of neuromuscular paralysis, occurs at a rate of 1.0 per 1,000 patients (Altekruse and Tollefson, 2003). Due to the emergence and persistence of antibiotic resistance coupled with increasing regulatory restrictions on the industry, control strategies such as vaccination are urgently needed. To date, there is no intervention method or vaccine available to the producer to reduce numbers of *Campylobacter* in poultry going to processing.

Beginning Jul. 1, 2011, USDA-FSIS (Food Safety and Inspection Service) has implemented new performance standards for *Campylobacter* for young chicken chilled carcasses at slaughter establishments (FSIS NOTICE, 31-11, Jun. 30, 2011). These standards will allow no more than 8 positive *Campylobacter* samples out of a 51-sample set, with plans to initially warn the companies and fines to be imposed in 2013. A large baseline study was conducted in our laboratory (funded by the USDA) to quantify *Campylobacter* levels in slaughtering plants from 2007-2009. Our studies demonstrated 21.9% (213/972) of post-chilled carcass rinse samples were positive for *Campylobacter*, which amounts to 11.17 per 51-sample set. Clearly, this is over the allowable number of *Campylobacter* from chilled carcass samples and will precipitate the issuing of fines for both the producer and processing plant unless a reduction of *Campylobacter* in poultry can be obtained. Currently, there are no available intervention methods or vaccines available for producers to use to reduce the *Campylobacter* load in poultry.

SUMMARY OF THE INVENTION

In a first aspect, the present invention provides immunogenic compositions, comprising one or more expression vectors comprising:
(a) at least one polynucleotide encoding a protein selected from the group consisting of proteins comprising an amino acid sequence at least 80 percent identical to SEQ ID NO:2 (Cj0998c protein), SEQ ID NO:4 (Cj0588 protein), and SEQ ID NO:6 (Cj0248 protein), or antigenic portions thereof; and (b) a promoter operatively linked to the polynucleotide, wherein the promoter region is capable of directing expression of the encoded protein(s).

In a second aspect, the present invention provides immunogenic compositions, comprising
(a) one or more isolated proteins selected from the group consisting of proteins comprising an amino acid sequence at least 80 percent identical to SEQ ID NO:2 (Cj0998c protein), SEQ ID NO:4 (Cj0588 protein), and SEQ ID NO:6 (Cj0248 protein), or antigenic portions thereof; and
(b) a pharmaceutically acceptable carrier.

In a third aspect, the present invention provides methods for stimulating an immune response against *Campylobacter*, comprising administering to a subject an effective amount of the immunogenic composition according to any embodiment of the invention to generate an immune response against *Campylobacter*.

In a fourth aspect, the present invention provides methods for reducing *Campylobacter* intestinal colonization in a subject, comprising administering an amount effective of the immunogenic composition according to any embodiment of the invention to reduce *Campylobacter* intestinal colonization in the subject.

DESCRIPTION OF THE FIGURES

FIG. 1 is a schematic drawing of the pYA3493 plasmid.

DETAILED DESCRIPTION OF THE INVENTION

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), Culture of Animal Cells: A Manual of Basic Technique, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides immunogenic compositions, comprising one or more expression vectors comprising:
(i) at least one polynucleotide encoding a protein selected from the group consisting of proteins comprising an amino acid sequence at least 80 percent identical to SEQ ID NO:2 (Cj0998c protein), SEQ ID NO:4 (Cj0588 protein), and SEQ ID NO:6 (Cj0248 protein), or antigenic portions thereof; and
(ii) a promoter operatively linked to the polynucleotide, wherein the promoter region is capable of directing expression of the encoded protein(s).

The inventors have identified three putative virulence genes (Cj0248, Cj0588, and Cj0998c) from *C. jejuni* encoding novel proteins from the outer-membrane of the bacterium. The inventors have further discovered that each of the Cj0998c protein, the Cj0588 protein, and the Cj0248 protein are potent immunogens for stimulating an effective immune response against *Campylobacter jejuni* ("*C. jejuni*"). For example, as disclosed in detail herein, two separate vaccination trials of chickens with a vector expressing the Cj0988c protein demonstrated reduced numbers of *C. jejuni* in birds after challenge an average of 2.5 logs CFU (geomean 3 logs) when compared to the cecal numbers of non-vaccinated control birds. Furthermore, vaccination trials demonstrated a significant reduction (1-4 logs) (1 log with heterologous strain and 4 logs with homologous strain) of *C. jejuni* in cecal contents of chickens vaccinated with vectors expressing the Cj0588 protein and challenged with *Campylobacter jejuni*. Each of the proteins was initially isolated from an outer-membrane (OMP) extraction of a *C. jejuni* biofilm.

Thus, the immunogenic compositions of the invention can be used, for example for stimulating an immune response in subjects at risk of *Campylobacter* infection and/or colonization, including but not limited to vertebrates such as chickens, turkeys, birds, cattle, sheep, pigs, dogs, cats, and humans.

In one embodiment, the one or more expression vectors encode one of the recited proteins, or antigenic fragments thereof. In another embodiment, the one or more expression vectors encode two proteins comprising an amino acid sequence at least 80 percent identical to the recited amino acid sequences (i.e.: SEQ ID NO:2 and SEQ ID NO:4; SEQ ID NO:2 and SEQ ID NO:6; or SEQ ID NO:6 and SEQ ID NO:8), or antigenic fragments thereof. In this embodiment, a single expression vector may encode both proteins, or antigenic fragments thereof, or the composition may comprise two expression vectors, with each expression vector encoding one of the recited proteins, or antigenic fragments thereof. In this embodiment, the expression vector used may be the same (other than the protein coding sequence) or different.

In a further embodiment, the one or more expression vectors encode all three of the proteins comprising an amino acid sequence at least 80 percent identical to the recited amino acid sequences (i.e.: SEQ ID NO:2, SEQ ID NO:4, and SEQ ID NO:6), or antigenic fragments thereof. In this embodiment, a single expression vector may encode all three proteins, or antigenic fragments thereof. Alternatively, the composition may comprise two expression vectors, with one expression vector encoding one of the recited proteins, or antigenic fragments thereof, and the other expression vector encoding two of the recited proteins, or antigenic fragments thereof. In a further alternative of this embodiment, the composition may comprise three expression vectors, with each expression vector encoding one of the recited proteins, or antigenic fragments thereof. In each of these alternative embodiments, the multiple expression vectors used may be the same or different. Non-limiting examples of expression vectors encoding the one or more recited proteins are provided herein. Based on the present disclosure, it is well within the level of those of skill in the art to prepare expression vectors according to all embodiments of the invention.

The Cj0998c, Cj0588, and Cj0248 proteins are present in highly conserved variants between different strains of *C. jejuni*, and thus the proteins encoded by the one or more expression vectors can be at least 80% identical or similar (residues with similar properties, i.e.: hydrophobic, hydrophilic, etc.) over the full length of the recited amino acid sequences, or antigenic fragments thereof. In various further embodiments, the proteins encoded by the one or more expression vectors are at least 81, 82, 83, 84, 85, 86, 87, 88, 89, 90, 91, 92, 93, 94, 95, 96, 97, 98, 99, or 100% percent identical over the full length of the recited amino acid sequence(s), or antigenic fragment thereof.

In one embodiment, the at least one polynucleotide encodes a protein selected from the group consisting of the following, or an antigenic fragment thereof:

```
(a) (Cj0998c genus)                    SEQ ID NO: 7
MKK(I/V/F)(L/V)(V/A/L)S(V/I)(L/F)S(S/F)CLLASALSA

VSFKEDSLK(I/V)SFEGYKTKDM(I/V)G(T/V/I/A)(K/R)GEFK

NVEY(K/N)FSK(N/S)(I/T)KD(L/F)ASYLKGAKATI(K/E)PS (N/D)AFM(G/S)EG(N/L)D(I/V)ITNNITKVFFPALLG(D/N)

(T/A)DIKVVFQD(V/A/M)I(A/V)GE-X1ITMDKKSTI(V/I)

PLTYTIKD(N/D)KFEAKGQ(L/F)DLH(T/A)FKN(G/A)SKALK

ALSD(V/A)A(A/T/P)GHGGISWPLVDISFNADL(A/T/V)E wherein X1 is absent or is
                                      (SEQ ID NO: 135)
NKGVISAK;

(b) (Cj0588 genus):                      SEQ ID NO: 8
X1-(L/M)(D/N/E)LL(S/R)EIY(V/I)SRAALKLK(K/N)

FLEEN(D/G/N)IE(I/V)(K/N)(H/Q/N)KNCLDIGSSTGGFV

QILLEN(Q/K)ALKIT(A/T)LDVG(S/N)NQLH(P/S/L)(S/N)

LR(V/A/T)NE(K/I)(I/V)IL(H/Y)EN(T/I)DLR(A/T/V)

FKSEEKFE(L/F)(V/I)TCDVSFISL(I/V)NLLYY(I/V)

(D/N)NLAL(K/R)EIILLFKPQFEVGKN(I/V)KRDKKGVLKD (D/G)(K/R)(A/V)ILKA(R/K)MDFEK(A/E)CAKL(G/S)W (L/F/I)LKNTQKS(S/C)IKGKEGNVEYFYYYIKN wherein X1 is absent or is
                                      (SEQ ID NO: 136)
M(R/I)(F/-)(D/-)FF(V/I)SKRL(N/D)ISRNKALELIE (N/S)EE(I/V)LLNGK(S/N)FKAS(F/C)DVKN(F/L)

LENLKK(T/A/K)QDLN(P/L/S)E(D/E)(I/V)(L/Y)L (A/T/S)(N/D/K)(E/G)L(K/N);
and (c) (Cj0248 genus)                     SEQ ID NO: 9
(M/-)I(G/-)DMNELLLKSVEVLPPLPDTVSKLRKYVSEANSN

IETMKV(A/V)EIISSDPLMTAKLLQLANSPYYGFTREITTI(N/S)

QVITLLG(V/I)GNIINIV(M/T)ADSI(R/K)D(N/S)FKIDVS

PYGL(N/D)T(Q/K)(N/V)FL(K/R)(T/N)CN(E/D)EATFI (A/V/T)NWLNDEDKKLSHLLVPCAMLLRLGIVIFSNFLIQN (H/Y/F)(K/R)-X1 wherein X1 is absent, or is
                              (SEQ ID NO: 137 or 138)
(D/E)K(D/E)FL(A/T)FLN(-/E/K)(-/T)K(N/S/I))EN (L/I)ALAENEFLGVDHISFLGFLL(H/Y)RWNFDD(V/I)LIESI

CFV(R/H)TPHAARE(K/E)VKKSAYALAITDHLF(A/T)PHDGSS

PFN(A/V/T)KAAVALL(K/E)EAK-X2;

and wherein X2 is absent or is selected from the
group consisting of
                                      (SEQ ID NO: 139)
TQGINFDL(N/D)NLLSKLP(N/S)KAKENL(N/D)(K/E)ED
and (SEQ ID NO: 140)
NSRN.
```

In various further embodiments, the at least one polynucleotide encodes a protein selected from the group consisting of SEQ ID NOS: 10-106, or an antigenic fragment thereof. SEQ ID NOS, 44-82 are each Cj0998c protein homologs from other *C. jejuni* strains; SEQ ID NOS, 83 to 106 are each Cj0588 protein homologs from other *C. jejuni* strains; and SEQ ID NOS, 10 to 43 are each Cj0248 protein homologs from other *C. jejuni* strains.

The expression vectors may encode "antigenic portions" of the recited protein. As used herein, and "antigenic portion" is any fragment of 10 or more contiguous amino acids in the recited amino acid sequence. In various further embodiments, the antigenic portion is any fragment of any of the embodiments of the invention is 15, 20, 25, 30, 40, 50, 75, 100, 125, 150, 175, 200, 225, 250, or 275 contiguous amino acids of the recited amino acid sequence.

The one or more isolated polynucleotides may be single or double stranded DNA, RNA, genomic DNA, or cDNA. The one or more isolated polynucleotides may be any nucleic acids encoding the recited one or more proteins, or antigenic fragments thereof. In one embodiment, the one or more isolated polynucleotides are one or more of SEQ ID NO:1 (Cj0998c gene), SEQ ID NO:3 (Cj0588 gene), and SEQ ID NO:5 (Cj0248 gene), or portions thereof encoding antigenic portions of the recited proteins. It will be apparent to those of skill in the art, based on the teachings herein, what polynucleotide sequences will encode the recited polypeptides or antigenic fragments thereof.

As used herein, "isolated polynucleotides" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, secretory signals, nuclear localization signals, and plasma membrane localization signals, as appropriate for a given use.

Any expression vector suitable for an intended use can be used in the immunogenic compositions of the present invention. Such expression vectors can be of any type known in the art, including but not limited to plasmid and viral-based expression vectors. The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors. Specifics of the expression vector will depend on the ultimate desired use. Designing appropriate expression vectors for an intended use is well within the level of those of skill in the art based on the teachings herein.

Any suitable promoter may be used that can direct expression (i.e.: is "operatively linked") of the encoded proteins. The term "promoter" includes any nucleic acid sequence sufficient to direct expression of the encoded protein(s), including inducible promoters, repressible promoters and constitutive promoters. If inducible, there are sequences present which mediate regulation of protein expression so that the polynucleotide is transcribed only when an inducer molecule is present. Such cis-active sequences for regulated expression of an associated polynucleotide in response to environmental signals are well known to the art. The expression vector may comprise any other control sequences as may be suitable for an intended use. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, enhancers, termination signals, and ribosome binding sites.

The immunogenic compositions of the present invention may further comprise any other suitable components as may be useful for a given purpose. In various non-limiting embodiments, the compositions may further comprise one or more expression vectors comprising at least one polynucleotide encoding a protein selected from the group consisting of proteins comprising an amino acid sequence at least 80 percent identical to an amino acid sequence of SEQ ID NO:142 (Cj1534c protein; encoded, for example, by SEQ ID NO:141), SEQ ID NO:108 (1656c protein; encoded, for example, by SEQ ID NO:107), SEQ ID NO:110 (0428 protein; encoded, for example, by SEQ ID NO:109), SEQ ID NO:112 (0168c protein; encoded, for example, by SEQ ID NO:111), SEQ ID NO:114 (0427 protein; encoded, for example, by SEQ ID NO:113), SEQ ID NO:116 (Cj0113 protein; encoded, for example, by SEQ ID NO:115), SEQ ID NO:118 (Cj0982c protein; encoded, for example, by SEQ ID NO:117), SEQ ID NO:120 (Cj0921c protein; encoded, for example, by SEQ ID NO:119), SEQ ID NO:122 (Cj1259 protein; encoded, for example, by SEQ ID NO:121), SEQ ID NO:124 (Cj1339c protein; encoded, for example, by SEQ ID NO:123), SEQ ID NO:126 (Cj0034c protein; encoded, for example, by SEQ ID NO:125), SEQ ID NO:128 (Cj0404 protein; encoded, for example, by SEQ ID NO:127), SEQ ID NO:130 (Cj0365c protein; encoded, for example, by SEQ ID NO:129), SEQ ID NO:132 (Cj0755 protein; encoded, for example, by SEQ ID NO:131), and SEQ ID NO:134 (Cj0420 protein; encoded, for example, by SEQ ID NO:133), or antigenic fragments thereof.

The one or more expression vectors may be the same or different one or more expression vectors that comprise the at least one polynucleotide encoding SEQ ID NO:2 (Cj0998c protein), SEQ ID NO:4 (Cj0588 protein), SEQ ID NO:6 (Cj0248 protein), or fragments thereof. All embodiments of the one or more expression vectors disclosed above apply equally for these additional components. By way of non-limiting example, the one or more expression vectors may be 1, 2, 3, or 4 additional vectors that encode SEQ ID NO:142 (Cj1534c protein), SEQ ID NO:108 (1656c protein), SEQ ID NO:110 (0428 protein), SEQ ID NO:112 (0168c protein), and SEQ ID NO:114 (0427 protein), or antigenic fragments thereof. Those of skill in the art will understand the variety of other combinations that can be employed in accordance with the methods of the invention. Based on the present disclosure, it is well within the level of those of skill in the art to prepare expression vectors according to all embodiments of the invention.

Similar to the immunogens recited above, the optional protein immunogens are present in highly conserved variants between different strains of *Campylobacter jejuni*, and thus the proteins encoded by the one or more expression vectors can be at least 80% identical over the full length of the recited amino acid sequences, or antigenic fragments thereof. In various further embodiments, the proteins encoded by the one or more expression vectors are at least 81, 82, 83, 84, 85, 86, 87, 88, 89, 90, 91, 92, 93, 94, 95, 96, 97, 98, 99, or 100% percent identical over the full length of the recited amino acid sequence(s), or antigenic fragment thereof.

The immunogenic compositions of the present invention may be used for inducing an immune response by administration as naked DNA using standard methods, such as by parenteral delivery. Alternatively, the expression vectors may comprise viral expression vectors, including but not limited to a recombinant adeno-associated virus (AAV) gene delivery vector. In this embodiment, the expression vector is bounded on the 5' and 3' end by functional AAV inverted terminal repeat (ITR) sequences. By "functional AAV ITR sequences" is meant that the ITR sequences function as intended for the rescue, replication and packaging of the AAV virion. Recombinant AAV (rAAV) virions encapsidating the expression vectors of the invention may be produced using standard methodology. In one embodiment, an AAV expression vector according to the invention is introduced into a producer cell, followed by introduction of an AAV helper construct, where the helper construct includes AAV coding regions capable of being expressed in the producer cell and which complement AAV helper functions absent in the AAV vector. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety. Any suitable method for producing viral particles for delivery can be used.

In another embodiment, the one or more expression vectors are present in a carrier cell, including but not limited to an avirulent, non-*Campylobacter* bacterial carrier cell. Live bacterial vaccine "vectors" (i.e.: bacterial cells comprising immunogenic compositions) have been used successfully to elicit effective immune responses in order to prevent infection. Recombinant attenuated bacterial cell delivered vaccines have been adapted to stably express protective antigens at high levels. They are capable of stimulating strong primary humoral, mucosal and lasting memory immune responses without significant tissue damage or other performance reducing effects. In various non-limiting embodiments, the bacterial carrier cell is an avirulent bacterial cell selected from the group consisting of attenuated *L. monocytogenes*, attenuated *Salmonella* spp., attenuated *V. cholerae*, attenuated *Shigella* spp., attenuated *M. bovis* BCG, attenuated *Y. enterocolitica*, attenuated *B. anthracis, S. gordonii, Lactobacillus* spp., and *Staphylococcus* spp. As used herein, "attenuated" means that the bacteria is reduced in causing disease symptoms in a host it is delivered to compared to a non-attenuated bacterial vector. Suitable attenuated bacteria can be any species or strain that is or can be sufficiently attenuated to allow for its non-pathological administration to humans and/or animals in live and/or dead form. In one embodiment, an attenuated *Salmonella* species is used. In exemplary embodiments, *Salmonella* that can be used include, but are not limited to *Salmonella enterica* strains selected from the group consisting of *S. Typhimurium, S. Enteriditis, S. Heidelberg, S. Gallinarum, S. Hadar, S. Agona, S. Kentucky, S. Typhi, S. Paratyphi* and *S. Infantis. S. Typhimurium* is especially useful for vaccination purposes because the genome sequence is fully characterized and many animal studies confirm its safe medical use. Recombinant attenuated *Salmonella* vaccines (RASVs) have been constructed to deliver antigens from other pathogens to induce immunity to those pathogens in vaccinated hosts; see, for example, Curtiss et al., Crit Rev Immunol. 2010; 30(3):255-70; 2010; Qiu et al., J. Virological Methods 188:108; Strugnell et al., Infect. Immunol. 1992, 60:3994; Layton et al., Clinical and Vaccine Immunology march 2011, 449-454; Al-Ojali et al., Microbial Pathogenesis 52:326 (2012); and (Wyszynska et al., 2004) Wyszyńska et al. (2004). In one embodiment, the RASV comprises attenuating mutations in the pmi (mannose-6-phosphate isomerase), fur (ferric uptake regulator) and crp (cAMP regulatory protein) genes (see, for example, (Li et al., PNAS 106:592-597 2009, Curtiss et al., 2009) and U.S. Pat. No. 8,133,493. In another embodiment, the RASV comprises the χ9992 vector disclosed in U.S. Pat. No. 8,133,493. In another embodiment, the RASV is one that is commercially available, such as Megan® Vac1 (Lohman Animal Health, US).

Attenuated bacterial cells can be transfected with the one or more expression vectors using standard techniques in the art.

In a second aspect, the present invention provides an immunogenic composition, comprising (a) one or more isolated proteins selected from the group consisting of proteins comprising an amino acid sequence at least 80 percent identical to SEQ ID NO:2 (Cj0998c protein), SEQ ID NO:4 (Cj0588 protein), and SEQ ID NO:6 (Cj0248 protein), or antigenic portions thereof; and (b) a pharmaceutically acceptable carrier.

As disclosed above for the first aspect of the invention, the immunogenic compositions of the second aspect of the invention can be used, for example for stimulating an immune response in subjects at risk of *C. jejuni* infection or colonization, including but not limited to vertebrates such as chickens, turkeys, cattle, sheep, pigs, and humans.

In one embodiment, the immunogenic composition comprises one of the recited proteins, or antigenic fragments thereof. In another embodiment, the immunogenic composition comprises two of the proteins comprising an amino acid sequence at least 80 percent identical to the recited amino acid sequences (i.e.: SEQ ID NO:2 and SEQ ID NO:4; SEQ ID NO:2 and SEQ ID NO:6; or SEQ ID NO:6 and SEQ ID NO:8), or antigenic fragments thereof. In a further embodiment, the immunogenic composition comprises all three of the proteins comprising an amino acid sequence at least 80 percent identical to the recited amino acid sequences (i.e.: (i.e.: SEQ ID NO:2, SEQ ID NO:4, and SEQ ID NO:6), or antigenic fragments thereof.

The Cj0998c, Cj0588, and Cj0248 proteins are present in highly conserved variants between different strains of *C. jejuni*, and thus the proteins can be at least 80% identical over the full length of the recited amino acid sequences, or antigenic fragments thereof. In various further embodiments, the proteins are at least 81, 82, 83, 84, 85, 86, 87, 88, 89, 90, 91, 92, 93, 94, 95, 96, 97, 98, 99, or 100% percent identical over the full length of the recited amino acid sequence(s), or antigenic fragment thereof.

In one embodiment, the at least one protein is selected from the group consisting of the following, or an antigenic fragment thereof:

(a) (Cj0998c genus)                           SEQ ID NO: 7
MKK(I/V/F)(L/V)(V/A/L)S(V/I)(L/F)S(S/F)CLLASALS

AVSFKEDSLK(I/V)SFEGYKTKDM(I/V)G(T/V/I/A)(K/R)

GEFKNVEY(K/N)FSK(N/S)(I/T)KD(L/F)ASYLKGAKATI (K/E)PS(N/D)AFM(G/S)EG(N/L)D(I/V)ITNNITKVFFPALLG (D/N)(T/A)DIKVVFQD(V/A/M)I(A/V)GE-X1ITMDKKSTI (V/I)PLTYTIKD(N/D)KFEAKGQ(L/F)DLH(T/A)FKN(G/A)

SKALKALSD(V/A)A(A/T/P)GHGGISWPLVDISFNADL(A/T/V)E wherein X1 is absent or is
                                              (SEQ ID NO: 135)
NKGVISAK;

(b) (Cj0588 genus):                           SEQ ID NO: 8:
X1-(L/M)(D/N/E)LL(S/R)EIY(V/I)SRAALKLK(K/N)

FLEEN(D/G/N)IE(I/V)(K/N)(H/Q/N)KNCLDIGSSTGGF

VQILLEN(Q/K)ALKIT(A/T)LDVG(S/N)NQLH(P/S/L)

(S/N)LR(V/A/T)NE(K/I)(I/V)IL(H/Y)EN(T/I)DLR (A/T/V)FKSEEKFE(L/F)(V/I)TCDVSFISL(I/V)NLLYY (I/V)(D/N)NLAL(K/R)EIILLFKPQFEVGKN(I/V)KRDKK

GVLKD(D/G)(K/R)(A/V)ILKA(R/K)MDFEK(A/E)CAKL (G/S)W(L/F/I)LKNTQKS(S/C)IKGKEGNVEYFYYYIKN wherein X1 is absent or is
                                              (SEQ ID NO: 136)
M(R/I)(F/-)(D/-)FF(V/I)SKRL(N/D)ISRNKALELIE (N/S)EE(I/V)LLNGK(S/N)FKAS(F/C)DVKN(F/L)LENLKK (T/A/K)QDLN(P/L/S)E(D/E)(I/V)(L/Y)L(A/T/S)

(N/D/K)(E/G)L(K/N);
and (c) (Cj0248 genus)                            SEQ ID NO: 9
(M/-)I(G/-)DMNELLLKSVEVLPPLPDTVSKLRKYVSEANSNI

ETMKV(A/V)EIISSDPLMTAKLLQLANSPYYGFTREITTI(N/S)

QVITLLG(V/I)GNIINIV(M/T)ADSI(R/K)D(N/S)

FKIDVSPYGL(N/D)T(Q/K)(NN)FL(K/R)(T/N)CN(E/D)

EATFI(A/V/T)NWLNDEDKKLSHLLVPCAMLLRLGIVIFSNF

LIQN(H/Y/F)(K/R)-X1 wherein X1 is absent, or is
                                              (SEQ ID NO: 137 or 138)
(D/E)K(D/E)FL(A/T)FLN(-/E/K)(-/T)K(N/S/I))EN (L/I)ALAENEFLGVDHISFLGFLL(H/Y)RWNFDD(V/I)

LIESICFV(R/H)TPHAARE(K/E)VKKSAYALAITDHLF(A/T)

PHDGSSPFN(A/V/T)KAAVALL(K/E)EAK-X2;

and wherein X2 is absent or is selected from the
group consisting of
                                              (SEQ ID NO: 139)
TQGINFDL(N/D)NLLSKLP(N/S)KAKENL(N/D)(K/E)ED
and
                                              (SEQ ID NO: 140)
NSRN.

In various further embodiments, the at least one polynucleotide encodes a protein selected from the group consisting of SEQ ID NOS: 10-106, or an antigenic fragment thereof. SEQ ID NOS, 44-82 are each Cj0998c protein homologs from other *C. jejuni* strains; SEQ ID NOS, 83-106 are each Cj0588 protein homologs from other *C. jejuni* strains; and SEQ ID NOS, 10-43 are each Cj0248 protein homologs from other *C. jejuni* strains.

The immunogenic composition of any embodiment of this second aspect of the invention may comprise "antigenic portions" of the recited proteins. As used herein, and "antigenic portion" is any fragment of 10 or more contiguous amino acids in the recited amino acid sequence. In various further embodiments, the antigenic portion is any fragment of 15, 20, 25, 30, 40, 50, 75, 100, 125, 150, 175, 200, 225, 250, or 275 contiguous amino acids of the recited amino acid sequence.

The immunogenic compositions of the second aspect of the invention may comprise proteins modified in any suitable way. In one embodiment, the protein component(s) of the composition are treated to extend in vivo half-life by, for example, such as by PEGylation, HESylation, PASylation, or glycosylation. The proteins may also be glycosylated as deemed appropriate, using standard techniques in the art. In another embodiment, those protein components in the immunogenic compositions that possess N-glycosylation sequences (NXS or NXT) may be glycosylated, to help further stimulate the immune response.

The immunogenic compositions of the second aspect of the invention may further comprise any other suitable components as may be useful for a given purpose. In various non-limiting embodiments, the compositions may further comprise one or more additional proteins selected from the group consisting of proteins comprising an amino acid sequence at least 80% identical to SEQ ID NO:142 (Cj1534c protein), SEQ ID NO:108 (Cj1656c protein), SEQ ID NO:110 (Cj0428 protein), SEQ ID NO:112 (Cj0168c protein), SEQ ID NO:114 (Cj0427 protein), SEQ ID NO:116 (Cj0113 protein), SEQ ID NO:118 (Cj0982c protein), SEQ ID NO:120 (Cj0921c protein), SEQ ID NO:122 (Cj1259 protein), SEQ ID NO:124 (Cj1339c protein), SEQ ID NO:126 (Cj0034c protein), SEQ ID NO:128 (Cj0404 protein), SEQ ID NO:130 (Cj0365c protein), SEQ ID NO:132 (Cj0755 protein), and SEQ ID NO:134 (Cj0420 protein), or antigenic fragments thereof. Similar to the immunogens recited above, the optional protein immunogens are present in highly conserved variants between different strains of *Campylobacter jejuni*, and thus the proteins can be at least 80% identical over the full length of the recited amino acid sequences, or antigenic fragments thereof. In various further embodiments, the proteins encoded by the one or more expression vectors are at least 81, 82, 83, 84, 85, 86, 87, 88, 89, 90, 91, 92, 93, 94, 95, 96, 97, 98, 99, or 100% percent identical over the full length of the recited amino acid sequence(s), or antigenic fragment thereof.

In another embodiment, the immunogenic compositions of the second aspect of the invention may further comprise a *C. jejuni* pilus protein as described in WO 2008/008092, incorporated by reference herein in its entirety. The pilus protein described in WO 2008/008092 was shown to stimulate an immune response against *C. jejuni*, and thus it is suitable for inclusion in the immunogenic compositions of the second aspect of the present invention. Methods for isolating the *C. jejuni* pilus protein are described in WO 2008/008092.

The immunogenic compositions of the invention may comprise any suitable amount/dosage of the composition as determined most appropriate. In one embodiment, the immunogenic composition comprises about $10^6$-$10^{10}$ avirulent bacterial cells per dose. In another embodiment where the composition comprises immunogenic proteins, the composition may comprise about 0.1 ug/kg-100 mg/kg body weight of the proteins; alternatively, it may be 0.5 ug/kg to 50 mg/kg; 1 ug/kg to 25 mg/kg, or 5 ug/kg to 10 mg/kg body weight of the proteins.

The immunogenic compositions of the present invention (i.e.: any embodiment or combination of embodiments of the first and second aspects of the invention) can be formulated by any of the means known in the art. The immunogenic compositions are typically formulated as a pharmaceutical composition, such as those disclosed above, and can be formulated for administration via any suitable route, including orally, as injectables, parentally, by inhalation spray, intranasally, rectally, mucosally, topically, or for administration by oral gavage or ad libitum feeding, for example, in drinking water, either as liquid solutions or suspension, in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Solid forms suitable for solution in, or suspension in, liquid prior to injection or other administration may also be prepared. The compositions may also, for example, be emulsified, or the encapsulated in liposomes or microparticles. The immunogenic compositions may also be present in and/or expressed by transgenic plants.

The immunogenic compositions according to the present invention may further comprise any suitable adjuvant Immunological adjuvants in general comprise substances that boost the immune response of the host in a nonspecific manner. A number of different adjuvants are known in the art. Examples of adjuvants are Freunds Complete and Incomplete adjuvant, vitamin E, non-ionic block polymers and polyamines such as dextransulphate, carbopol and pyran, oligopeptide, emulsified paraffin-Emulsigen™ (MVP Labs, Ralston, Nebr.), L80 adjuvant containing aluminum hydroxide (Reheis, N.J.), Quil A™ (Superphos); surface active substances such as Span™, Tween™, hexadecylamine, lysolecitin, methoxyhexadecylglycerol and saponins; peptides such as muramyldipeptides, dimethylglycine, and tuftsin; immune-stimulating complexes (ISCOMS), mineral oil e.g. Bayol or Markol, vegetable oils or emulsions thereof, aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-s-n-glycero-3hydroxyphosphoryloxy)-ethylamine (CGP 19835A, referred to as MTP-PE); and RIBI, which contains three components extracted from bacteria: monophosphoryl lipid A, trehalose dimycolate and cell wall skeleton (MPL+TDM+CWS) in a 2% squalene/Tween 80 emulsion. In embodiments designed for mucosal administration, the immunogenic compositions may further comprise an adjuvant, including but not limited to such as the nontoxic cholera toxin B subunit (Sigma Chemical Company, St. Louis, Mo.) and organometallopolymers including linear, branched or cross-linked silicones which are bonded at the ends or along the length of the polymers to the particle or its core. Such polysiloxanes can vary in molecular weight from about 400 up to about 1,000,000 daltons; the preferred length range is from about 700 to about 60,000 daltons. Suitable functionalized silicones include (trialkoxysilyl)alkyl-terminated polydialkylsiloxanes and trialkoxysilyl terminated polydialkylsiloxanes, for example, 3-(triethyoxysilyl)propyl terminated polydimethylsiloxane. See U.S. Pat. No. 5,571,531, incorporated by reference herein. Phosphazene poly-electrolytes can also be incorporated into immunogenic compositions for mucosal administration (See e.g., U.S. Pat. No. 5,562,909).

The immunogenic compositions according to the present invention may also comprise preservatives such as sodium azide, thimersol, gentamicin, neomycin, and polymyxin.

The immunogenic compositions may be mixed with excipients or carriers which are pharmaceutically acceptable and compatible with the protein immunogen(s) to be used. Suitable excipients include, but are not limited to, water, saline, dextrose, glycerol, ethanol, or the like and combinations thereof. Such an immunogenic composition can easily be prepared by admixing the protein with a pharmaceutically acceptable carrier. A pharmaceutically acceptable carrier is understood to be a compound that does not adversely affect the health of the animal to be vaccinated, at least not to the extent that the adverse effect is worse than the effects seen when the animal is not vaccinated. A pharmaceutically acceptable carrier can be e.g. sterile water or a sterile physiological salt solution. In a more complex form, the carrier can e.g. be a buffer.

The immunogenic composition may further comprises stabilizers, e.g. to protect degradation-prone components from being degraded, to enhance the shelf-life of the composition, or to improve freeze-drying efficiency. Useful stabilizers include, without limitation, SPGA, skimmed milk, gelatin, bovine or other serum albumin, carbohydrates e.g. sorbitol, mannitol, trehalose, starch, sucrose, dextran or glucose, proteins such as albumin or casein or degradation products thereof, and buffers, such as alkali metal phosphates. Where an albumin is used, it is desirably from the same species as the animal (or human) to which the immunogenic composition containing it will be administered. Freeze-drying is an efficient method for conservation. Freeze-dried material can be stored stable for many years. Storage temperatures for freeze-dried material may well be above zero degrees, without being detrimental to the material. Freeze-drying can be done according to all well-known standard freeze-drying procedures. However, the immunogenic compositions of the invention may be stored in any suitable manner. For example, the immunogenic compositions could be lyophilized or otherwise stabilized and stored in food or water for delivery.

In an exemplary embodiment when the immunogenic compositions are designed for administration to a non-human subject, such as chickens, turkeys, birds, sheep, pigs, cattle, dogs, or cats, the immunogenic composition is formulated for mucosal administration, such as by admixing of the composition with drinking water or food, or admixing for use as a spray, to mist over the animals to uptake the immunogenic composition during grooming behavior. However, any suitable method of administration can be used for any subject. Thus, in various embodiments the immunogenic compositions are formulated for intraocular, intranasal, or transdermal administration.

In a third aspect, the present invention provides methods for stimulating an immune response against *Campylobacter*, comprising administering to a subject an effective amount of the immunogenic composition according to any embodiment or combination of embodiments of the first or second aspects of the present invention to generate an immune response against *Campylobacter*.

In a fourth aspect, the present invention provides methods for reducing *Campylobacter* intestinal colonization in a subject, comprising administering an amount effective of the immunogenic composition according to any embodiment or combination of embodiments of the first or second aspects of the present invention to reduce *Campylobacter* intestinal colonization in the subject.

As disclosed herein, the inventors have identified three novel putative virulence genes (Cj0248, Cj0588, and Cj0998c) from *C. jejuni* encoding novel proteins from the outer-membrane of the bacterium. The inventors have further discovered that each of the Cj0998c protein, the Cj0588 protein, and the Cj0248 protein are potent immunogens for stimulating an effective immune response against *Campylobacter jejuni* ("*C. jejuni*"). For example, as disclosed in detail herein, two separate vaccination trials of chickens with a vector expressing the Cj0988c protein demonstrated reduced numbers of *C. jejuni* in birds after challenge an average of 2.5 logs CFU (geomean 3 logs) when compared to the cecal numbers of non-vaccinated control birds. Furthermore, vaccination trials demonstrated a significant reduction (1-4 logs) (1 log with heterologous strain and 4 logs with homologous strain) of *C. jejuni* in cecal contents of chickens vaccinated with vectors expressing the Cj0588 protein and challenged. Each of the proteins was initially isolated from an outer-membrane (OMP) extraction of a *C. jejuni* biofilm.

Campylobacteriosis is a food-borne disease primarily generally caused by *C. jejuni*. The major risk factor in acquiring the disease is the handling and consumption of poultry. However, the epidemiology of poultry colonization with *Campylobacter* such as *C. jejuni* is extremely complex. Birds become colonized within 14 days of hatching, spreading the infection throughout the flock by the end of the grow-out period. Strain differences, based on subtyping and/or genotyping assays, exist between and within flocks. Although some flocks remain *Campylobacter*-free, most flocks have 50-100% of the birds colonized by grow-out. Nevertheless, broilers (i.e., chickens of either gender that will be slaughtered for meat at about 5 to 8 weeks old depending on weight) become contaminated with *Campylobacter*, such as *C. jejuni* and although this microorganism acts as normal flora in the chicken, undercooked chicken is a primary vehicle for transmission of *Campylobacter*, such as *C. jejuni* to humans and remains a significant public health concern.

The methods may be used on any suitable subject at risk of *Campylobacter* infection, including but not limited to vertebrates such as chickens, turkeys, birds, cattle, sheep, pigs, dogs, cats, and humans. In one non-limiting embodiment, a human subject may be anyone that consumes chicken, beef, turkey, or pork. In another embodiment, a human subject may be one that works with animals (i.e.: farm workers, workers at slaughterhouses and meat processing plants, etc.) such as chickens, turkeys, cattle, sheep, and pigs.

In another embodiment, the subject is a feed animal such as chickens, turkeys, cattle, sheep, and pigs. In a preferred embodiment, the subject is a chicken. In these embodiments, the feed animal may be of any suitable age. Birds become colonized with *C. jejuni* within 14 days of hatching, spreading the infection throughout the flock by the end of the grow-out period. Thus, in one embodiment, the methods are initially carried out by about 14 days after hatching. It will be understood by those of skill in the art that additional booster administrations may be desirable after the initial administration; such booster administrations can be carried out at any suitable time, such as by about 21 days after hatching.

In another non-limiting embodiment where the subject is a feed animal, the methods are carried out before slaughtering. However, it will be understood that the methods can be used on chickens or turkeys at any suitable time, as appropriate for a given use.

Campylobacteriosis is currently one of the most common bacterial food-borne diseases in humans in the U.S. and is responsible for causing an estimated 1.3 million cases annually in the U.S., often accompanied by acute gastroenteritis. The infectious dose in the development of the disease is variable and ranges from 500 to $10^6$ organisms. Variation in infectious dose is thought to be due to either individual susceptibility or to the relative virulence of the organism. The incubation period is one to seven days with clinical symptoms including fever, severe abdominal cramps, and a watery diarrhea or a dysentery-like syndrome typical of shigellosis. The disease is usually self-limiting, lasting from two to seven days but occasionally is fatal (120-360 deaths per year), mainly in infants and young adults. Serious complications such as arthritis occur in an estimated 1-5% of cases and Guillain-Barre Syndrome, a form of neuromuscular paralysis occurs at a rate of 1 per 1,000 patients.

Conversely, *Campylobacter*, such as *C. jejuni*, colonizes poultry as a commensal, that is, without producing any overt signs of disease. Similarly, *Campylobacter*, such as *C. jejuni* may colonize other feed animals as a commensal as well. However, infected cattle may suffer from diarrhea, weight loss, and suffer from fever and increased heart rate.

The methods of the third and fourth aspects of the invention may be used to stimulate an immune response against or to reduce intestinal colonization of any species of *Campylobacter*. In preferred embodiments, the methods of the third and fourth aspects of the invention are used to stimulate an immune response against or to reduce intestinal colonization of varied species of *Campylobacter* including but not limited to *C. jejuni, C. coli, C. lari* and/or *C. upsaliensis*.

As used herein, methods for "stimulating an immune response" result in one or more effects (e.g., maturation, proliferation, direct- or cross-presentation of antigen, gene expression profile) on cells of either the innate or adaptive immune system. For example, the immune response may involve, effect, or be detected in innate immune cells such as, for example, dendritic cells, monocytes, macrophages, natural killer cells, and/or granulocytes (e.g., neutrophils, basophils or eosinophils). The immune response may also involve, effect, or be detected in adaptive immune cells including, for example, lymphocytes (e.g., T cells and/or B cells). The immune response may be observed by detecting such involvement or effects including, for example, the presence, absence, or altered (e.g., increased or decreased) expression or activity of one or more immunomodulators. The immune response may stimulate a de novo or previously undetected antibody response, or enhance or suppress an existing response against the immunogen by, for example, causing an increased antibody response (e.g., amount of antibody, increased affinity/avidity) or an increased cellular response (e.g., increased number of activated T cells, and/or increased affinity/avidity of T cell receptors. In certain embodiments, the immune response may be protective, meaning that the immune response may be capable of preventing initiation or continued infection of or growth within a host and/or by eliminating *C. jejuni* from the host. In some instances, elimination of an agent from the host may mean that the method is therapeutic, in that the method is used to treat a subject already infected with *C. jejuni*. When the method is therapeutic, the method may comprise treating a *C. jejuni* infection, wherein "treating" means accomplishing one or more of the following: (a) reducing the severity of the infection; (b) limiting or preventing development of symptoms characteristic of the infection; (c) inhibiting worsening of symptoms characteristic of the infection; (d) limiting or preventing recurrence of the disorder(s) in subjects that have previously had the infection;

and (e) limiting or preventing recurrence of symptoms in subjects that were previously symptomatic for the infection.

As used herein, "reducing *Campylobacter* intestinal colonization" means reducing a level of intestinal colonization that would be observed in the subject in the absence of administering the one or more immunogenic compositions of the invention. Any level of reduction is beneficial in reducing *Campylobacter* transmission, for example, from poultry to a human consuming the poultry. In one embodiment, the reduction comprises at least 10% reduction in intestinal colonization compared to intestinal colonization in the absence of treatment; in various further embodiments, the intestinal colonization is reduced by at least 20%, 25%, 50%, 75%, 80%, 85%, 90%, 95%, or more compared to intestinal colonization in the absence of treatment. Techniques for quantifying a level of *Campylobacter* intestinal colonization are well known in the art and include, but are not limited to, examining cecal or fecal levels of *Campylobacter*. Techniques for determining fecal contamination of *Campylobacter* in production to quantify the level of *Campylobacter* organisms from a carcass rinse of feed animals, such as poultry, at various points of processing, such as after chilling are also established.

In preferred embodiments of the third and fourth aspects of the invention, the one or more expression vectors are present in a carrier cell, including but not limited to a non-*Campylobacter* bacterial carrier cell. In various non-limiting embodiments, the bacterial carrier cell is an avirulent bacterial cell selected from the group consisting of attenuated *L. monocytogenes*, attenuated *Salmonella* spp., attenuated *V. cholerae*, attenuated *Shigella* spp., attenuated *M. bovis* BCG, attenuated *Y. enterocolitica*, attenuated *B. anthracis*, *S. gordonii*, *Lactobacillus* spp., and *Staphylococcus* spp. In one embodiment, an attenuated *Salmonella* species is used. In exemplary embodiments, *Salmonella* that can be used include, but are not limited to *Salmonella enterica* strains selected from the group consisting of *S. Typhimurium, S. Enteriditis, S. Heidelberg, S. Gallinarum, S. Hadar, S. Agona, S. Kentucky, S. Typhi, S. Paratyphi* and *S. Infantis*. *S. Typhimurium* is especially useful for vaccination purposes because the genome sequence is fully characterized and many animal studies confirm its safe medical use. Recombinant attenuated *Salmonella* vaccines (RASVs) have been constructed to deliver antigens from other pathogens to induce immunity to those pathogens in vaccinated hosts; see, for example, Curtiss et al., Crit. Rev Immunol. 2010; 30(3):255-70; 2010; Qiu et al., J. Virological Methods 188:108; Strugnell et al., Infect. Immunol. 1992, 60:3994; Layton et al., Clinical and Vaccine Immunology march 2011, 449-454; Al-Ojali et al., Microbial Pathogenesis 52:326 (2012); and Wyszyńska et al. (2004). In one embodiment, the RASV comprises attenuating mutations in the pmi, fur and crp genes and U.S. Pat. No. 8,133,493. In another embodiment, the RASV comprises the χ9992 vector disclosed in U.S. Pat. No. 8,133,493. In another embodiment, the RASV is one that is commercially available, such as Megan® Vac1 (Lohman Animal Health, US).

The immunogenic compositions can be administered via any suitable route, including orally, as injectables, parentally, by inhalation spray, intranasally, rectally, mucosally, topically, or for administration by oral gavage or ad libitum feeding, for example, in drinking water, either as liquid solutions or suspension, in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Solid forms suitable for solution in, or suspension in, liquid prior to injection or other administration may also be prepared. The compositions may also, for example, be emulsified, or the encapsulated in liposomes.

In an exemplary embodiment when the subject is a non-human subject, such as chickens, turkeys, birds, sheep, pigs, cattle, dogs, or cats, the immunogenic composition are administered orally or mucosally, such as by admixing of the composition with drinking water or food, or admixing for use as a spray, to mist over the animals to uptake the immunogenic composition during grooming behavior. In exemplary embodiments where the subject is a human, the immunogenic compositions are administered orally or mucosally. However, any suitable method of administration can be used for any subject.

The immunogenic compositions are administered in a manner compatible with the dosage formulation, and in such amount and manner as will be prophylactically and/or therapeutically effective, according to what is known to the art. The quantity to be administered depends on the subject to be treated, the functional capacity of the subject's immune system, the degree of protection desired, and other factors. Precise amounts of the active ingredient required to be administered may depend on the judgment of the individual administering the immunogenic compositions and may be peculiar to each individual, but such a determination is within the level of those of skill in the art based on the teachings herein. In one embodiment, about $10^6$-$10^{10}$ avirulent bacterial cells per dose can be administered. In another embodiment where immunogenic proteins are administered, a suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight.

The immunogenic compositions may be administered in a single dose or in multiple dosages as determined most appropriate, such as a two dose schedule, for example two to eight weeks apart; or a multiple dose schedule or in combination with other vaccines. A multiple dose schedule is one in which a primary course of vaccination may include 1 to 10 or more separate doses, followed by other doses administered at subsequent time intervals as required to maintain and/or reinforce the immune response, e.g., at 1 to 4 months for a second dose, and if needed, a subsequent dose(s) after several months.

EXAMPLE 1

Immunogenic Compositions Based on Cj0988c

The DNA and protein sequence of Cj0988c are provided in SEQ ID NO:1 and SEQ ID NO:2, respectively.

*Salmonella Typhimurium* vector χ9992:

The vector used was a *Salmonella Typhimurium* vector χ9992 (Curtiss et al., 2009) which contains eight mutations, with three of the mutations attenuating: the pmi, fur, and crp genes.

1) Δpmi-2426—Eliminates phosphomannose isomerase which ceases LPS-O antigen synthesis in the absence of mannose;

2) Δgmd-fcl—Reduces biofilm formation and prevents the formation of colonic acid which aids in the survival of asdA mutants;

3) ΔasdA27—Deletion of a gene encoding an enzyme necessary for diaminopimelic acid (DAP). Strain requires supplemental DAP until the introduction of the plasmid. Eliminates need for antibiotic resistance markers;

4) $\Delta P_{fur77}$::TT araC $P_{BAD}$fur::TT araC $P_{BAD}$c2 $\Delta$Pcrp527::TT araC $P_{BAD}$ crp—Allows fur and crp gene expression only in the presence of arabinose, producing pYA3493 (FIG. 1), a strain which is maximally invasive prior to display of attenuated phenotype following cell division;

5) $\Delta$relA198::araCP$_{BAD}$lacITT—eliminates relA gene to uncouple growth from protein synthesis and provides arabinose-dependent synthesis of the LacI repressor to confer regulated delayed in vivo synthesis of recombinant proteins, and 6) $\Delta$araE25 $\Delta$araBAD23—Eliminates the ability of *Salmonella* to metabolize arabinose. Allows retention of arabinose in the cytoplasm without use.

The vector plasmid pYA3493 contains the asd gene to compliment the chromosomal $\Delta$asdA27 mutation and ensure that the plasmid will not be lost in vivo. The plasmid also fuses the expressed product to a β-lactamase signal sequence for periplasmic secretion of the protein. Finally, the plasmid has a strong promoter (–35 region of trp promoter/−10 lac) in $P_{trc}$ (FIG. 1). Use of this plasmid does not confer antibiotic resistance to the *Salmonella* vaccine.

The vector that we used for the amplification of the plasmid with the inserted *C. jejuni* gene is *E. coli* χ6212. This strain is Asd-allowing amplification of the plasmid, which is then extracted and electroporated into *Salmonella* χ9992.

Gene Cj0998c expresses a hypothetical protein that is part of the outer membrane of the bacterium. Gene Cj0998c was cloned individually into plasmid pYA3493 and expressed from the *Salmonella* vector χ9992.

A. Cloning of the Cj0998c Gene into the *Salmonella* Vector

The *Salmonella* strain (χ9992) used as the vector has three different mutations which results in its attenuation. The strain is safe and immunogenic and acts as a phenotypically wild-type strain at the time of immunization but becomes attenuated after colonization of host tissues. The plasmid contains the asd gene which provides a marker for laboratory differentiation using media not containing DAP to grow plasmid-containing strains. Since this gene is required for the survival of the vector without DAP, the plasmid is maintained in the vector during in vivo colonization. Gene Cj0998c was cloned into *Salmonella* χ9992. Essentially, primers to each gene were designed and the gene amplified using PCR. Each gene product was inserted into plasmid pYA3493 (asd+), cloned into *E. coli* χ6212 (asd−) and cultured for amplification. Following growth, the plasmid was extracted from the *E. coli* strain, cloned into the *Salmonella Typhimurium* vector, and the transformants plated on LB media minus DAP, cultured at 37° C. on LB agar, harvested, and stored frozen at −80° C. Confirmation that the gene was present in the vector was accomplished through a plasmid extraction and sequence analysis of genes following PCR and gel electrophoresis.

B. *Salmonella* Growth In Vitro

The *Salmonella* vector expressing the Cj0998c protein and the *Salmonella* empty vector were grown in Luria Bertani (LB) broth supplemented with 0.1% glucose, 0.05% mannose, and 0.1% arabinose for 24 h at 37° C. with shaking. Following incubation, the overnight cultures were pelleted and re-suspended in PBS to a final concentration of $1\times10^{10}$ CFU/ml.

C. Vaccination of Poultry

Vaccination of chickens, twice, with the vector expressing the Cj0988c protein reduced cecal numbers of *C. jejuni* in birds an average of 2.5 logs CFU (geomean of 3.0 logs CFU) when compared to the cecal numbers of non-vaccinated control birds (Table 1). One outlier of 1.00 E+07 (highlighted cell, Table 3) was present in 31 birds examined Cornish X Rock chickens were obtained from McMurray Hatchery (IA) and randomly assigned to isolated groups. The chickens were screened for the fecal presence of *C. jejuni* and/or *Salmonella*. The chickens were vaccinated orally, at days 10 and 16, with 1 ml of the *Salmonella* vector expressing the Cj0988 protein (~$10^{10}$ CFU/ml) or the *Salmonella* empty vector and challenged with $10^5$ CFU/ml of *C. jejuni* strain NCTC11168 10 days after the second vaccination. Prior to vaccination and challenge, chickens were fasted for 8 hours. Food was returned one hour post vaccination/challenge. Aside from this period, food and water were available ad libitum. The chickens were necropsied 10 days after challenge infection. Cecal contents were ten-fold diluted and direct plated onto modified Campy Cefex agar plates incubated for 48 h at 10% $CO_2$ microaerophilic conditions for enumeration of *Campylobacter*.

TABLE 1

Combined data of *C. jejuni* vaccination trials 1 & 2
*C. jejuni* NCTC11168 Challenge-Trials 1&2

| | Cj0998c | Control-EV | Controls |
|---|---|---|---|
| Average | 6.11E+05 | 6.75E+07 | 1.15E+08 |
| Geomean | 2.60E+04 | 4.41E+07 | 4.83E+07 |

TABLE 2

Vaccination Trial 1 - Ten day old chickens vaccinated twice with the vector expressing gene Cj0998c, or the *Salmonella* empty vector only (Control-EV), or non-vaccinated controls
*C. jejuni* NCTC11168 Challenge - Trial 1

| | Cj0998c | Control-EV | Controls |
|---|---|---|---|
| | 1.0E+03 | 1.0E+07 | 3.0E+08 |
| | 7.0E+04 | 1.2E+07 | 6.0E+07 |
| | 7.4E+04 | 1.0E+08 | 1.0E+07 |
| | 8.2E+04 | 2.0E+08 | 1.0E+07 |
| | 1.0E+04 | 7.0E+07 | 2.0E+08 |
| | 2.0E+04 | 9.0E+07 | 2.0E+07 |
| | 3.0E+04 | 1.0E+08 | 4.0E+08 |
| | 2.0E+03 | 1.0E+08 | 1.2E+08 |
| | 6.0E+04 | 2.0E+07 | 1.0E+07 |
| | 3.0E+04 | 1.0E+07 | 2.0E+07 |
| Average | 3.79E+04 | 7.12E+07 | 1.15E+08 |
| Geomean | 1.98E+04 | 4.45E+07 | 4.83E+07 |

TABLE 3

Vaccination Trial 2-Ten day old chickens vaccinated twice with the vector expressing gene Cj0998c (two groups), or the *Salmonella* empty vector only (Control-EV)

| C. jejuni NCTC11168 Challenge-Trial 2 | | |
|---|---|---|
| Cj0998c | Cj0998c | Control-EV |
| 1.40E+04 | 2.00E+05 | 5.00E+07 |
| 3.20E+03 | 1.70E+05 | 3.00E+07 |
| 7.00E+04 | 3.00E+04 | 2.00E+07 |
| 1.00E+02 | 2.70E+05 | 1.70E+08 |
| 7.00E+04 | 3.00E+05 | 3.00E+07 |
| 9.00E+03 | 2.40E+04 | |
| 1.05E+04 | 1.50E+04 | |
| 1.00E+00 | 5.00E+06 | |
| 6.00E+03 | 2.30E+06 | |
| 3.00E+03 | 1.00E+07 | |
| 6.00E+04 | | |
| Average 2.23E+04 | 1.83E+06 | 6.00E+07 |
| Geomean 3.78E+03 | 2.84E+05 | 4.33E+07 |

EXAMPLE 2

Immunogenic Compositions Based on Cj0588 and Cj0248

1. The DNA and protein sequence of Cj0588 are provided in SEQ ID NO:3 and SEQ ID NO:4, respectively.
2. The DNA and protein sequence of Cj0248 are provided in SEQ ID NO:5 and SEQ ID NO:6, respectively.
3. Mutation of *C. jejuni* Genes Genes Cj0588 and Cj0248 were cloned and mutated in *C. jejuni* by insertion of a chloramphenicol cassette in the center of each gene. Essentially, two sets of primers were designed for each gene to yield fragments consisting of the initial and terminal 15 bases of the gene and their associated flanking regions. These fragments were cloned into a suicide vector and positioned around the chloramphenicol acetyltransferase (CAT) gene, such that the antibiotic cassette was between the initial and terminal regions of the gene, taking up ~255 bases of each gene. The vector containing the CAT gene and the flanking bases of each gene was then introduced by electroporation into *C. jejuni* strain M129 (Cj0588) or strain NCTC11168 (Cj0248), and the mutation transferred into the genome via a double crossover. Following electroporation the mutant strain was plated on Mueller Hinton agar containing chloramphenicol. Colonies that grew on the selective media were then confirmed by PCR to contain the cassette in the chromosome in the proper direction. Colonies were then harvested and stored at −78° C.

4. Effects of the Cj0588 Mutation on Broiler Colonization.

The ΔCj0588 mutant and M129 *C. jejuni* parent strain were each examined for colonization traits in poultry. Four separate studies were conducted. The detection limit is less than 10 organisms. There was a significant reduction in the colonization of birds inoculated with the M129::tlyA mutant, demonstrating that the *C. jejuni* Cj0588 gene is important in the colonization of poultry.

Study 1:

Chickens were obtained and housed as above. At 12 days, chickens were orally inoculated with 1.0 ml of approximately $1.0 \times 10^5$ per ml of viable *C. jejuni* M129 and the M129::tlyA mutant. At day 22 the birds were necropsied, and *Campylobacter* was enumerated as above. There was a significant reduction in the colonization of birds inoculated with the M129::tlyA mutant.

TABLE 4

Colonization of chickens with a *C. jejuni* parent M129 and M129::tlyA strain.

| M129::tlyA | M129::tlyA | M129 | M129 |
|---|---|---|---|
| 52 | ND | 73 | 1.00E+02 |
| 53 | ND | 74 | ND |
| 54 | ND | 75 | 2.00E+02 |
| 55 | ND | 76 | ND |
| 56 | ND | 77 | 4.20E+03 |
| 57 | ND | 78 | ND |
| 58 | ND | 79 | ND |
| 59 | ND | 80 | ND |
| 60 | ND | 81 | 1.20E+04 |
| 61 | ND | 82 | 1.00E+04 |
| TOTAL | ND | Average | 5.30E+03 |

Study 2:

Chickens were obtained and housed as above. At 14 days, birds were orally inoculated with 1.0 ml of approximately $1.0 \times 10^6$ per ml of viable *C. jejuni* M129 and the M129::tlyA mutant. At day 28, the birds were necropsied, and *Campylobacter* was enumerated as above. There was a significant reduction in the colonization of birds inoculated with the M129::tlyA mutant.

TABLE 5

Colonization of chickens with a *C. jejuni* parent M129 and M129::tlyA strain.

| M129::tlyA | M129::tlyA | M129 | M129 |
|---|---|---|---|
| 1 | ND | 1 | 2.30E+05 |
| 2 | ND | 2 | 1.40E+05 |
| 3 | ND | 3 | 1.50E+03 |
| 4 | ND | 4 | ND |
| 5 | ND | 5 | ND |
| 6 | ND | 6 | 1.30E+06 |
| 7 | ND | 7 | ND |
| 8 | ND | 8 | 1.90E+03 |
| 9 | ND | 9 | 1.80E+03 |
| 10 | ND | 10 | ND |
| 11 | ND | 11 | 8.70E+03 |
| 12 | ND | 12 | ND |
| 13 | ND | 13 | 1.70E+03 |
| 14 | ND | 14 | 1.70E+03 |
| 15 | ND | 15 | ND |
| 16 | ND | 16 | 3.60E+03 |
| 17 | ND | 17 | 3.10E+03 |
| TOTAL | ND | Average | 1.54E+05 |

Study 3:

Chickens were obtained and housed as above. At 14 days, birds were orally inoculated with 1.0 ml of approximately $1.0 \times 10^8$ per ml of viable *C. jejuni* M129 and the M129::tlyA mutant. At day 28, the birds were necropsied, and *Campylobacter* was enumerated as above. There was a significant reduction in the colonization of birds inoculated with the M129::tlyA mutant.

TABLE 6

Colonization of chickens with a *C. jejuni* parent M129 and M129::tlyA strain.

| M129::tlyA | M129::tlyA | M129 | M129 |
|---|---|---|---|
| 1 | ND | 1 | 9.40E+04 |
| 2 | ND | 2 | 2.10E+03 |
| 3 | ND | 3 | 2.10E+03 |
| 4 | ND | 4 | 1.00E+02 |
| 5 | ND | 5 | 4.70E+03 |
| 6 | ND | 6 | 2.60E+07 |
| 7 | ND | 7 | 3.70E+03 |
| 8 | ND | 8 | 1.10E+03 |
| 9 | ND | 9 | 4.00E+03 |
| 10 | ND | 10 | 2.70E+03 |
| 11 | ND | 11 | 2.80E+03 |
| 12 | ND | 12 | 1.50E+04 |
| 13 | ND | 13 | 2.10E+03 |
| 14 | ND | 14 | 1.10E+03 |
| 15 | ND | 15 | 1.50E+05 |
| 16 | ND | 16 | 5.10E+03 |
|  |  | 17 | 2.00E+02 |
| TOTAL | ND | Average | 1.55E+06 |

Study 4

Chickens were obtained and housed as above. At 14 days, birds were orally inoculated with 1.0 ml of approximately $1.0 \times 10^8$ per ml of viable *C. jejuni* M129 and the M129::tlyA mutant. At day 28, the birds were necropsied, and *Campylobacter* was enumerated as above. There was a significant reduction in the colonization of birds inoculated with the M129::tlyA mutant.

TABLE 7

Colonization of chickens with a *C. jejuni* parent M129 and M129::tlyA strain.

| M129::tlyA | M129::tlyA | M129 | M129 |
|---|---|---|---|
| 1 | ND | 1 | 1.10E+03 |
| 2 | ND | 2 | 2.00E+04 |
| 3 | ND | 3 | ND |
| 4 | ND | 4 | 1.00E+02 |
| 5 | ND | 5 | 4.30E+03 |
| 6 | ND | 6 | 2.30E+03 |
| 7 | ND | 7 | 1.00E+02 |
| 8 | ND | 8 | 3.00E+02 |
| 9 | ND | 9 | 1.00E+02 |
| 10 | ND | 10 | ND |
| 11 | ND | 11 | 2.30E+03 |
| 12 | ND | 12 | 2.80E+03 |
| 13 | ND | 13 | 1.70E+06 |
| 14 | ND | 14 | 1.10E+03 |
| 15 | ND | 15 | 1.50E+03 |
| 16 | ND | 16 | 2.80E+03 |
| 17 | ND | 17 | 1.10E+04 |
| 18 | ND | 18 | 1.10E+03 |
| 19 | ND | 19 | 7.00E+02 |
| 20 | ND | 20 | 2.50E+05 |
| 21 | ND | 21 | 1.10E+06 |
| 22 | ND | 22 | ND |
| 23 | ND | 23 | 4.80E+03 |
| TOTAL | ND | Average | 1.35E+05 |

5. Effects of the ΔCj0248 Mutation on Broiler Colonization.

The ΔCj0248 mutant and NCTC11168 *C. jejuni* parent strain were examined for colonization traits in poultry. Chickens were obtained and housed as above. At day 14, the birds were orally inoculated with 0.5 ml of approximately $1.0 \times 10^5$ per ml of viable *C. jejuni* strain NCTC11168 (n=31), the ΔCj0248 mutant strain (n=30), or served as negative controls. At day 24, the birds were necropsied, and *Campylobacter* was enumerated as above. There was a significant reduction in the colonization of birds inoculated with the ΔCj0248 mutant strain. All the birds inoculated with the wild-type strain NCTC11168 were colonized at an average of 7.42 E+07 CFU/g, whereas, 3 of 30 birds (<10 CFUs) were colonized at an average of 7.33 E+01 CFU/g with the *C. jejuni* mutant strain ΔCj0248 (Table 8).

TABLE 8

Colonization of Broilers with *C. jejuni* NCTC11168 Wild-type and Mutant

| Controls | NCTC11168 Wild Type | | | NCTC11168 Mutant Cj0248 | | |
|---|---|---|---|---|---|---|
|  | Group 1 | Group 2 | Group 3 | Group 1 | Group 2 | Group 3 |
| ND | 3.30E+07 | 2.30E+08 | 4.60E+05 | ND | ND | 2.00E+02 |
| ND | 4.10E+08 | 3.20E+07 | 8.00E+03 | ND | ND | ND |
| ND | 1.60E+07 | 4.20E+05 | 1.00E+04 | ND | 1.90E+03 | ND |
| ND | 2.40E+07 | 7.10E+07 | 1.20E+04 | ND | ND | ND |
| ND | 9.30E+05 | 8.20E+04 | 3.40E+07 | ND | ND | 1.00E+02 |
| ND | 2.00E+06 | 9.50E+07 | 3.30E+05 | ND | ND | ND |
| ND | 1.40E+07 | 5.00E+06 | 3.10E+07 | ND | ND | ND |
| ND | 9.50E+08 | 5.30E+07 | 1.50E+06 | ND | ND | ND |
| ND | 5.90E+07 | 8.30E+07 | 1.00E+02 | ND | ND | ND |
| ND | 2.40E+07 | 2.30E+04 | 3.10E+03 | ND | ND | ND |
| — |  | 1.30E+08 |  | ND |  |  |
| Average | 1.51E+08 | 5.70E+07 | 6.73E+06 | ND | 1.90E+02 | 3.33E+01 |

Average: Wild type = 7.42E+07; Mutant = 7.33E+01; ND = not detected, <10 CFU

6. *Salmonella Typhimurium* Vector χ9992:

The vector used is a *Salmonella Typhimurium* vector χ9992, as described above.

7. Cloning and Expressing *C. jejuni* Genes into the *Salmonella* Vector.

Both genes Cj0588 and Cj0248 were cloned into the vector plasmid pYA3493 and expressed from the attenuated *Salmonella Typhimurium* vector χ9992, as described above.

8. Vaccination of Chickens with the Attenuated *Salmonella* Vector Expressing Cj0588 from Plasmid pYA3493.

Chickens were obtained, housed, and vaccinated as above. Trial 1 chickens were orally challenged with 1.0 ml of the homologous *C. jejuni* strain M129 (~$1 \times 10^7$ CFU/ml) and trial 2 chickens were orally challenged with 1.0 ml of a heterologous strain *C. jejuni* NCTC11168 (~1×10$^5$ CFU/ml) at 10 days after the final vaccination. Ten days post challenge, the chickens were necropsied, and *Campylobacter* enumerated as above.

In trial 1, a 4-log reduction of *C. jejuni* in cecal contents of chickens vaccinated with the vector expressing Cj0588 protein following challenge with the homologous M129 strain was observed, as compared to chickens receiving the empty vector (EV) vaccine. A 2-log reduction in *C. jejuni* was observed when the Cj0588 vaccinates were compared to the normal controls. In trial 2, an overall 1-log reduction of *C. jejuni* in cecal contents of chickens vaccinated with the Cj0588 protein was observed following challenge with a heterologous strain NCTC11168, as compared to chickens receiving the EV vaccine. These trials demonstrated a significant reduction of *C. jejuni* in cecal contents of chickens vaccinated with the vector expressing the Cj0588 protein and challenged with the homologous strain. In addition, a 1-log reduction was seen in chickens challenged with a heterologous strain. A greater reduction would have occurred in trial 2 if not for three outliers (shaded boxes) (Table 9).

*Campylobacter* colonization, while colonization was reduced by ~1 log in the other group, as compared to empty vector and positive control groups.

EXAMPLE 4

Water Vaccination Using Cj0998c

Chickens were obtained and housed as above, with the exception that no fasting period was observed prior to vaccination and that water was removed for two hours prior to vaccination. On days 10 and 16, ~1×10$^{10}$ cfu of *Salmonella* expressing Cj0998c (prepared as above) was added to ~2 L of water in commercially available fountain waterers. Water was returned when all vaccine had been consumed (8-12 hours). Controls received ~1×10^10 cfu empty vector *Salmonella* or no vaccine orally. Chickens were orally challenged with 1.0 ml of the homologous *C. jejuni* strain NCTC11168 (~1×10$^5$ CFU/ml) at 10 days after the final vaccination. At day 36, the chickens were necropsied and *Campylobacter* enumerated as above. *Campylobacter* colonization was reduced in vaccinate groups by approximately 2.5 logs as compared to empty vector and positive control groups.

TABLE 9

Cecal numbers of *C. jejuni* in vaccinated (Cj0588) and control chickens

| | C. jejuni M129 Challenge-Trial 1 | | | | C. jejuni NCTC11168 Challenge-Trial 2 | | | |
|---|---|---|---|---|---|---|---|---|
| | Cj0588 | Control-EV | Controls | | Cj0588 | Cj0588 | Cj0588 | Control-EV |
| | 6.00E+03 | 1.00E+04 | 2.00E+04 | | 1.10E+03 | 5.00E+03 | 1.20E+05 | 5.00E+07 |
| | 7.00E+02 | 2.00E+04 | 7.00E+04 | | 1.50E+03 | 9.00E+04 | 1.00E+00 | 3.00E+07 |
| | 7.00E+03 | 1.00E+04 | 1.00E+05 | | 1.00E+02 | 3.00E+03 | 1.20E+04 | 2.00E+07 |
| | 3.30E+03 | 1.00E+05 | 3.00E+04 | | 1.00E+02 | 1.00E+00 | 6.00E+04 | 1.70E+08 |
| | 2.00E+02 | 3.00E+04 | 3.00E+04 | | 5.00E+03 | 4.00E+01 | 1.00E+02 | 3.00E+07 |
| | 7.00E+02 | 3.00E+04 | 7.00E+04 | | 1.00E+03 | 3.00E+07 | 4.00E+07 | |
| | 8.00E+03 | 1.00E+04 | 1.00E+04 | | 2.00E+03 | 5.00E+01 | 2.70E+04 | |
| | 3.00E+03 | 3.00E+04 | 1.00E+06 | | 7.00E+02 | 1.70E+04 | 6.00E+02 | |
| | 3.00E+03 | 3.00E+04 | 1.00E+04 | | 2.00E+01 | 5.00E+07 | 7.00E+04 | |
| | 3.20E+03 | 5.00E+04 | 1.00E+04 | | 5.00E+04 | 2.00E+02 | 1.20E+05 | |
| | 1.00E+03 | 2.30E+04 | 3.50E+05 | | 7.00E+01 | 1.00E+00 | 2.00E+04 | |
| | 4.00E+03 | 1.00E+04 | 7.00E+04 | | 5.60E+03 | 1.00E+00 | 2.00E+04 | |
| | 6.80E+03 | 1.00E+04 | 2.10E+06 | Average | 5.60E+03 | 6.68E+06 | 3.37E+06 | 6.00E+07 |
| | 2.30E+03 | 3.00E+08 | 7.00E+04 | Geomean | 7.73E+02 | 1.24E+03 | 1.28E+04 | 4.33E+07 |
| | 1.40E+03 | 1.00E+04 | 3.00E+05 | Combined Trial 2 data | | | | |
| | 7.00E+03 | | 6.00E+05 | | Cj0588 | | | Control-EV |
| Average | 3.60E+03 | 2.00E+07 | 3.03E+05 | Average | 3.35E+06 | | | 6.00E+07 |
| Geomean | 2.47E+03 | 3.83E+04 | 8.36E+04 | Geomean | 2.31E+03 | | | 4.33E+07 |

EXAMPLE 3

Dual Vaccination Using Cj0998c and Cj0588

Chickens were obtained, housed, and vaccinated as above, with the exception that each chicken received 2 ml of vaccine, 1 ml per antigen, at each vaccination. Chickens were orally challenged with 1.0 ml of the homologous *C. jejuni* strain NCTC11168 (~1×10$^5$ CFU/ml) at 10 days after the final vaccination. Ten days post challenge the chickens were necropsied, and *Campylobacter* enumerated as above. One vaccinate group showed a near total ~7 log reduction in

REFERENCES

Kong, Q., Six, D. A., Roland, K. L., Liu, Q., Gu, L., Reynolds, C. M., Wang, X., Raetz, C. R., Curtiss, R., 3rd, 2011. *Salmonella* synthesizing 1-dephosphorylated [corrected] lipopolysaccharide exhibits low endotoxic activity while retaining its immunogenicity. J Immunol 187, 412-423.

Wyszynska, A., Raczko, A., L is, M., Jagusztyn-Krynicka, E. K., 2004. Oral immunization of chickens with avirulent *Salmonella* vaccine strain carrying *C. jejuni* 72 Dz/92 cjaA gene elicits specific humoral immune response associated with protection against challenge with wild-type *Campylobacter*. Vaccine 22, 1379-1389.

Scallan E, Hoekstra R M, Angulo F J, Tauxe R V, Widdowson M A, Roy S L, et al. Foodborne illness acquired in the United States—major pathogens. Emerging infectious diseases. 2011; 17(1):7-15. Epub 2011, Jan. 5. doi: 10.3201/eid/1701.091101p1. PubMed PMID: 21192848.

Buzby J C, Allos B M, Roberts T. The economic burden of *Campylobacter*-associated Guillain-Barre syndrome. Journal of Infectious Diseases. 1997; 176:S192-S7. PubMed PMID: ISI:A1997YH50600023.

Pope J E, Krizova A, Garg A X, Thiessen-Philbrook H, Ouimet J M. *Campylobacter* reactive arthritis: a systematic review. Semin Arthritis Rheum. 2007; 37(1):48-55. Epub 2007 Mar. 16. doi: 50049-0172(07)00005-4 [pii]

Li, Y., Wang, S., Scarpellini, G., Gunn, B., Xin, W., Wanda, S. Y., Roland, K. L., Curtiss, R., 3rd, 2009, Evaluation of new generation *Salmonella enterica* serovar Typhimurium vaccines with regulated delayed attenuation to induce immune responses against PspA. Proceedings of the National Academy of Sciences of the United States of America 106, 593-598.

Curtiss III, R., S—Y. Wanda, B. M. Gunn, X. Zhang, S. A. Tinge, V. Ananthnarayan, H. Mo, S. Wang, and W. Kong. 2009. *Salmonella* strains with regulated delayed attenuation in vivo. Infect. Immun. 77:1071-1082.

We claim:

1. An immunogenic composition, comprising one or more expression vectors comprising:
   (a) one or more polynucleotide encoding two or more proteins including
      (i) a protein comprising an amino acid sequence at least 80 percent identical to SEQ ID NO:2 (Cj0998c protein), or antigenic portions thereof, and
      (ii) at least one protein comprising an amino acid sequence at least 80 percent identical to SEQ ID NO:4 (Cj0588 protein), and/or SEQ ID NO:6 (Cj0248 protein), or antigenic portions thereof; and
   (b) a promoter operatively linked to the one or more polynucleotide, wherein the promoter region is capable of directing expression of the encoded protein(s).

2. The immunogenic composition of claim 1, wherein the composition comprises one or more polynucleotide encoding all three of the recited proteins, or antigenic portions thereof.

3. The immunogenic composition of claim 1, wherein the one or more polynucleotide encodes a protein comprising the amino acid sequence of SEQ ID NO:7, or an antigenic portion thereof, and one or more proteins comprising an amino acid sequence selected from the group consisting of SEQ ID NO:8, and SEQ ID NO:9, or antigenic portions thereof.

4. The immunogenic composition of claim 1, wherein the at least one polynucleotide encodes two or more proteins comprising an amino acid sequence selected from the group consisting of SEQ ID NO: 10-106.

5. The immunogenic composition of claim 1, wherein the one or more polynucleotide encodes a protein comprising the amino acid sequence of SEQ ID NO:2 (Cj0998c protein), and one or more proteins selected from the group consisting of SEQ ID NO:4 (Cj0588 protein), and SEQ ID NO:6 (Cj0248 protein).

6. An immunogenic composition, comprising one or more expression vectors comprising:
   (a) at least one polynucleotide encoding two or more proteins selected from the group consisting of proteins comprising an amino acid sequence at least 80 percent identical to SEQ ID NO:10-106, wherein one protein comprises an amino acid sequence at least 80 percent identical to a protein selected from the group consisting of SEQ ID NOS: 44-82, and at least one other protein comprises an amino acid sequence at least 80 percent identical to a protein selected from the group consisting of SEQ ID NOS:10-43 and 83-106; and
   (b) a promoter operatively linked to the at least one polynucleotide, wherein the promoter region is capable of directing expression of the encoded protein(s).

7. The immunogenic composition of claim 1, wherein the immunogenic composition is present in an avirulent, non-*Campylobacter* bacterial carrier cell.

8. The immunogenic composition of claim 7, wherein the avirulent, non-*Campylobacter* bacterial carrier cell is selected from the group consisting of attenuated *L. monocytogenes*, attenuated *Salmonella*, attenuated *V. cholerae*, attenuated *Shigella* spp., attenuated *M. bovis* BCG, attenuated *Y. enterocolitica*, attenuated *B. anthracis*, *S. gordonii*, *Lactobacillus* spp., and *Staphylococcus* spp.

9. The immunogenic composition of claim 7, wherein the avirulent, non-*Campylobacter* bacterial carrier cell is an attenuated *Salmonella*.

10. The immunogenic composition of claim 1, further comprising one or more expression vectors comprising at least one polynucleotide operatively linked to a promoter and encoding one or more proteins selected from the group consisting of proteins comprising an amino acid sequence at least 80 percent identical to the amino acid sequence of a protein selected from the group consisting of SEQ ID NO:142 (Cj1534c protein), SEQ ID NO:108 (Cj 1656c protein), SEQ ID NO:110 (Cj0428 protein), SEQ ID NO:112 (Cj0168c protein), SEQ ID NO:114 (Cj0427 protein), SEQ ID NO:116 (Cj0113 protein), SEQ ID NO:118 (Cj0982c protein), SEQ ID NO:120 (Cj0921c protein), SEQ ID NO:122 (Cj1259 protein), SEQ ID NO:124 (Cj1339c protein), SEQ ID NO:126 (Cj0034c protein), SEQ ID NO:128 (Cj0404 protein), SEQ ID NO:130 (Cj0365c protein), SEQ ID NO:132 (Cj0755 protein), and SEQ ID NO:134 (Cj0420 protein), or antigenic fragments thereof.

11. The immunogenic composition of claim 1, further comprising one or more expression vectors comprising at least one polynucleotide operatively linked to a promoter and encoding one or more proteins having the amino acid sequence of a protein selected from the group consisting of SEQ ID NO:142 (Cj1534c protein), SEQ ID NO:108 Cj 1656c protein), SEQ ID NO:110 (Cj0428 protein), SEQ ID NO:112 (Cj0168c protein), SEQ ID NO:114 (Cj0427 protein), SEQ ID NO:116 (Cj0113 protein), SEQ ID NO:118 (Cj0982c protein), SEQ ID NO:120 (Cj0921c protein), SEQ ID NO:122 (Cj 1259 protein), SEQ ID NO:124 (Cj 1339c protein), SEQ ID NO:126 (Cj0034c protein), SEQ ID NO:128 (Cj0404 protein), SEQ ID NO:130 (Cj0365c protein), SEQ ID NO:132 (Cj0755 protein), and SEQ ID NO:134 (Cj0420 protein).

12. The immunogenic composition of claim 5, further comprising one or more expression vectors comprising at least one polynucleotide operatively linked to a promoter and encoding one or more proteins selected from the group consisting of proteins comprising an amino acid sequence at least 80 percent identical to the amino acid sequence of a protein selected from the group consisting of SEQ ID NO:142 (Cj1534c protein), SEQ ID NO:108 (Cj 1656c protein), SEQ ID NO:110 (Cj0428 protein), SEQ ID NO:112 (Cj0168c protein), SEQ ID NO:114 (Cj0427 protein), SEQ ID NO:116 (Cj0113 protein),SEQ ID NO:118 (Cj0982c protein), SEQ ID NO:120 (Cj0921c protein), SEQ ID NO:122 (Cj1259 protein), SEQ ID NO:124 (Cj1339c protein), SEQ ID NO:126 (Cj0034c protein), SEQ ID NO:128 (Cj0404 protein), SEQ ID NO:130 (Cj0365c protein), SEQ ID NO:132 (Cj0755 protein), and SEQ ID NO:134 (Cj0420 protein), or antigenic fragments thereof.

13. The immunogenic composition of claim 5, further comprising one or more expression vectors comprising at least one polynucleotide operatively linked to a promoter and encoding one or more proteins having the amino acid sequence of a protein selected from the group consisting of SEQ ID NO:142 (Cj1534c protein), SEQ ID NO:108 Cj 1656c protein), SEQ ID NO:110 (Cj0428 protein), SEQ ID NO:112 (Cj0168c protein), SEQ ID NO:114 (Cj0427 protein), SEQ ID NO:116 (Cj0113 protein),SEQ ID NO:118 (Cj0982c protein), SEQ ID NO:120 (Cj0921c protein), SEQ ID NO:122 (Cj 1259 protein), SEQ ID NO:124 (Cj 1339c protein), SEQ ID NO:126 (Cj0034c protein), SEQ ID NO:128 (Cj0404 protein), SEQ ID NO:130 (Cj0365c protein), SEQ ID NO:132 (Cj0755 protein), and SEQ ID NO:134 (Cj0420 protein).

14. The immunogenic composition of claim 5, wherein the immunogenic composition is present in an avirulent, non-Campylobacter bacterial carrier cell.

15. The immunogenic composition of claim 12, wherein the immunogenic composition is present in an avirulent, non-Campylobacter bacterial carrier cell.

16. The immunogenic composition of claim 13, wherein the immunogenic composition is present in an avirulent, non-Campylobacter bacterial carrier cell.

17. The immunogenic composition of claim 14, wherein the immunogenic composition is present in an avirulent, non-Campylobacter bacterial carrier cell.

18. The immunogenic composition of claim 15, wherein the avirulent, non-Campylobacter bacterial carrier cell is an attenuated Salmonella.

19. The immunogenic composition of claim 16, wherein the avirulent, non-Campylobacter bacterial carrier cell is an attenuated Salmonella.

20. The immunogenic composition of claim 17, wherein the avirulent, non-Campylobacter bacterial carrier cell is an attenuated Salmonella.

\* \* \* \* \*